US008273706B2

(12) United States Patent
Pappin et al.

(10) Patent No.: US 8,273,706 B2
(45) Date of Patent: Sep. 25, 2012

(54) ISOBARICALLY LABELED ANALYTES AND FRAGMENT IONS DERIVED THEREFROM

(75) Inventors: Darryl J. C. Pappin, Boxborough, MA (US); Subhasish Purkayastha, Acton, MA (US); James M. Coull, Westford, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 155 days.

(21) Appl. No.: 12/561,074

(22) Filed: Sep. 16, 2009

(65) Prior Publication Data
US 2010/0129842 A1 May 27, 2010

Related U.S. Application Data

(63) Continuation of application No. 10/852,730, filed on May 24, 2004, now abandoned, which is a continuation-in-part of application No. 10/822,639, filed on Apr. 12, 2004, now abandoned, which is a continuation-in-part of application No. 10/751,353, filed on Jan. 5, 2004, now abandoned.

(51) Int. Cl.
*A61K 38/00* (2006.01)
*C12Q 1/34* (2006.01)
(52) U.S. Cl. .......................................... 514/1.1; 435/18
(58) Field of Classification Search .................... None
See application file for complete search history.

(56) References Cited

U.S. PATENT DOCUMENTS

| | | | |
|---|---|---|---|
| 5,087,815 A | 2/1992 | Schultz et al. | |
| 5,705,610 A | 1/1998 | Zuckermann et al. | |
| 5,800,992 A | 9/1998 | Fodor et al. | |
| 6,270,976 B1 | 8/2001 | Schmidt et al. | |
| 6,287,780 B1 | 9/2001 | Schmidt et al. | |
| 6,383,754 B1 | 5/2002 | Kaufman et al. | |
| 6,395,474 B1 | 5/2002 | Buchardt et al. | |
| 6,475,807 B1 | 11/2002 | Geysen et al. | |
| 6,824,981 B2 | 11/2004 | Chait et al. | |
| 7,045,296 B2 | 5/2006 | Parker et al. | |
| 7,132,295 B2 * | 11/2006 | Lerchen et al. | 436/173 |
| 7,799,576 B2 * | 9/2010 | Pappin et al. | 436/173 |
| 7,906,341 B2 * | 3/2011 | Purkayastha et al. | 436/173 |
| 2004/0033625 A1 | 2/2004 | Aebersold | |
| 2004/0219686 A1 * | 11/2004 | Pappin et al. | 436/173 |
| 2005/0049406 A1 | 3/2005 | Lerchen et al. | |
| 2005/0147985 A1 * | 7/2005 | Pappin et al. | 435/6 |
| 2005/0148087 A1 * | 7/2005 | Pappin et al. | 436/86 |
| 2005/0153456 A1 * | 7/2005 | Pappin | 436/166 |
| 2010/0129842 A1 * | 5/2010 | Pappin et al. | 435/18 |

FOREIGN PATENT DOCUMENTS

| | | |
|---|---|---|
| EP | 0209763 | 7/1986 |
| EP | 0990047 B1 | 2/1999 |
| EP | 1701945 | 9/2006 |
| JP | 01125357 A2 | 5/1989 |
| WO | WO98/15652 | 4/1998 |
| WO | WO98/26095 | 6/1998 |
| WO | WO 98/31830 A | 7/1998 |
| WO | WO99/02728 | 1/1999 |
| WO | WO99/13103 | 3/1999 |
| WO | WO99/14362 | 3/1999 |
| WO | WO00/20112 | 4/2000 |
| WO | WO01/68664 A2 | 9/2001 |
| WO | WO02/46770 | 6/2002 |
| WO | WO03/056343 | 7/2003 |
| WO | WO03/078584 | 9/2003 |
| WO | WO03/102220 | 12/2003 |
| WO | WO 2004/019000 A | 3/2004 |
| WO | 2004/070352 A2 | 8/2004 |
| WO | WO2004/070352 A | 8/2004 |
| WO | WO2004/086050 | 10/2004 |
| WO | WO2005/068446 A | 7/2005 |

OTHER PUBLICATIONS

European Search Report dated Sep. 30, 2010 with Communication (extended European search report dated Oct. 16, 2010) transmitting the same, 7 pages.
Golding et al., "Chemistry of Nitrogen Mustard [2-chloro-N-(2-chloroethyl)-N-methyleth anamine] studed by nuclear magnetic resonance spectroscopy" J. Chem. Soc., Perkin Transactions 2, Chem. Soc., Letchworth, GB (1987) pp. 705-713.
Bottari P et al: "Design and Synthesis of Visible Isotope-Coded Affinity Tags for The Absolute Quantification of Specific proteins in Complex Mixtures" Bioconjugate Chemistry, ACS, Washington, D.C., U.S. vol. 15, No. 2, Feb. 21, 2004, pp. 380-388.
Brenner, S. et al. "Encoded Combinatorial Chemistry". Proc. Natl. Acad. Sci. USA 89, 5831-5383 (1992).
Chakraborty A., et al. "Global internal standard technology for comparative proteomics" Journal of Chromatography A, Elsevier, Amsterdam NL, vol. 949, No. 1-2, Mar. 8, 2002, pp. 173-184.
Duffield, A. et al., "Mass Spectrometry in Structural and Stereochemical Problems LVIII. A Study of the Fragmentation Processes of Some Lactams", Contribution from the Department of Chemistry of Stanford University, Stanford, CA, Aug. 5, 1964, pp. 5536-5541.
Gallop, M. et al. "Applications of Combinatorial Technologies to Drug Discovery. 1. Background And Peptide Combinatorial Libraries". Journal of Medicinal Chemistry 9, 1233-1251 (1994).
Gan Chee Sian et al, "Technical experimental, and biological variations in isobaric tags for relative and absolute quantitation (iTRAQ)", Journal of Proteome Research, vol. 6, No. 2, 2007, pp. 821-827.
Gatlin, C et al, Carboxylate and Amine Terminus Directed Fragmentations in Gaseous Dipeptide Complexes with Copper (II) and Diimine Ligands Formed by Electrospray, Anal. Chem. 1996, 68, 263-270.
Gatlin, C et al, "Copper(II) Amino Acid Complexes in the Bas Phase", J. Am. Chem. Soc. 1995, 117, 3637-3638.
Geysen, H. et al. "Strategies For Epitope Analysis Using Peptide Synthesis". Journal of Immunological Methods 102, 259-274 (1987).
Gorden, E. et al. "Applications of Combinatorial Technologies to Drug Discovery. 2. Combinatorial Organic Synthesis, Library Screening Strategies, and Future Directions". Journal of Medicinal Chemistry 10, 1385-1401.

(Continued)

*Primary Examiner* — Marcela M Cordero Garcia

(57) ABSTRACT

This invention pertains to isobarically labeled analytes and fragment ions thereof.

7 Claims, 35 Drawing Sheets

OTHER PUBLICATIONS

Gygi, Stephen et al. "Quantitative analysis of complex protein mixtures using isotope-coded affinity tags", Database Biosis (online) Biosciences Information Service, Philadelphia, PA, US: Oct. 1999, Database accession No. PREV199900527242, abstract; figure 1 & Nature Biotechnology, vol. 17, No. 10, Oct. 1999, pp. 994-999.

Haralambidou, E., et al., "Effect of Distal Positional Isomerism on Peptide Fragmentation. A Comparison of Dimethylaminobenzylidene and Benzoyl Derivatives", Organic Mass Spectrometry, 10: 683-697 (1975).

Kerr, J. et al. "Encoded Combinatorial Peptide Libraries Containing Non-Natural Amino Acids". J. Am. Chem. Soc. 115, 2529-2531 (1993).

Kurth, M. et al."Library-Based Lead Compound Discovery: Antoxidants By An Analogous Synthesis/Deconvolutive Assay Strategy". J. Org. Chem. 59, 5862-5864 (1994).

Lunazzi L., et al. "The effect of exocyclic conjugation on the inversion of a saturated six-membered ring. A dynamic NMR study of N-substituted morpholines" Tetrahedron 1991 United Kingdom, vol. 47, No. 35, 1991, pp. 7465-7470.

Modzihradszky, Katalin et al, "Peptide Sequence Determination by Matrix-Assisted Laser Desorption Ionization Employing a Tandem Double Focusing Magnetic-Orthogonal Acceleration Time-of-Flight Mass Spectrometer", American Society for Mass Spectrometry. 1996, 7, 1-10.

Moran E. J. et al."Radio Frequency Tag Encoded Combinatorial Library Method For The Discovery of Tripeptide-Substituted Cinnamic Acid Inhibitors of The Protein Tyrosine Phosphates PTP1B". J. Am. Chem. Soc. 117, 10787-10788 (1995).

Nielsen, J. et al. "Synthetic Methods For The Implementation of Encoded Combinatorial Chemistry". J. Am. Chem. Soc. 115, 9812-9813 (1993).

Peng, Junmin et al, "Proteomics: the move to mixtures", Journal of Mass Spectrometry, 2001: 36, 1083-1091.

Ross, P et al, "Multiplexed protein quantitation in *Saccharomyces cerevisiae* using amine-reactive isobaric tagging reagents" Molecular & Cellular Proteomics, ASBBM, Birmingham, AL, US, vol. 3, No. 12 Dec. 2004.

Spengler, R et al, "Peptide Sequencing of Charged Derivatives by Postsource Decay MALDI Mass Spectrometry", International Journal of Mass Spectrometry and Ion Processes, 169/170 (1997) 127-140.

SuBmuth, R., et al, "Impact of Mass Spectrometry on Combinatorial Chemistry", Journal of Chromatography B, 725 (1999) 49-65.

Supplementary European Search Report, EP 04 70 5571, Apr. 4, 2007.

Zhu, Xuegong et al, "Peptide Quantification by Tandem Mass Spectrometry", Mass Spectrometry Reviews, 1996, 15, 213-240.

Munchbach M et al: "Quantitation and Facilitated De Novo Sequencing of Proteins by Isotopic N-Terminal Labeling of Peptides with a Fragmentation-Directing Moeity", Analytical Chemistry, vol. 72, No. 17, Sep. 1, 2000, pp. 4047-4057.

Ross, Philip et al, "Multiplexed protein quantitation in *Saccharomyces cerevisiae* using amine-reactive isobaric tagging reagents", Molecular & Cellular Proteomics, Dec. 2004, vol. 3, No. 12, pp. 1154-1169.

PCT International Search Report and Written Opinion mailed Aug. 10, 2006.

Bartlett Jones, M., et al., "Peptide Ladder Sequencing by Mass Spectrometry Using a Novel, Volatile Degradation Reagent", Rapid Communications in Mass Spectrometry, vol. 8, 737-742 (1994).

Day, Richard et al, "N-Terminal Groups in Mass Spectrometry of Peptides. A Study Including Some New and Useful Derivatives", J. Org. Chem., vol. 38, No. 4, 1975 782-788.

Huang, Yulin et al, "A Method for High Efficiency peptide Sequencing Using Combined Enzymatic Digestion and Chemical Derivatization on MALDI MSMS", Applied Biosystems Poster No. 1159.

Ross, Philip et al, "'Investigation of Chemical Derivatization for Peptide CID Using LC-MALDI TOF MS/MS", Applied Biosystems Poster No. ThPF 250.

Roth, Kenneth et al, "Charge Derivatization of Peptides for Analysis by Mass Spectrometry", Mass Spectrometry Reviews, 1998, 17, 255-274.

Sherman, Nicholas et al, "A Novel N-Terminal Derivative Designed to Simplify Peptide Fragmentation", Proceedipgs of the 43$^{rd}$ ASMS Conference on Mass Spectrometry and Allied Topics, Atlanta, Georgia, May 21-26, 1995, pp. 626-627.

Applied Biosystems iTRAQ Reagents. Amine-Modifying Labeling Reagents for Multiplexed Relative and Absolute Protein Quantification. Chemistry Reference Guide. Part No. 4351918 Rev. A (May 2004).

Zieske et al. (Aug. 2004) Protein and Biomarker Quantitation Using iTRAQ Reagents; Poster presented during the 2D Electrophoresis meeting; Aug. 29-Sep. 2, 2004; Sienna, Italy.

Applied Biosystems (May 2004) Applications Note. Multiplex Protein Quantitation in *Saccharomyces cerevisae* using iTRAQ Reagents with the QSTAR XL System and the 4700 Proteomics Discovery System.

Shetty, Umesha H. et al, "Piperazine Ring Cleavage in the Electron Impact Induced Fragmentation of Piperazine Type Phenothiazine Antipsychotic Agents", Biomedical Mass Spectrometry, vol. 10, No. 11, 1983, pp. 601-607.

Golding, B.T. et al, "Chemistry of Nitrogen Mustard [2-Chloro-N-(2-chloroethyl)-N-methylethanamine] studied by Nuclear Magnetic Resonance Spectroscopy", Journal of the Chemical Society, Perkin Transactions 2, Chemical Society, Letchworth, GB, 1987, pp. 705-713.

PCT/US2005/000223 International Search Report Apr. 19, 2005.

* cited by examiner

Mass Of Compounds X-XIII = 131.144

Mass Of Compounds XV and XVI = 129.151

Mass Of Compounds XVII and XVIII = 129.138

Note: The Mass Stated Is Only For The Reporter/Linker Combination

Scheme For The Synthesis Of N-Methyl Piperazine

Scheme A For The Synthesis Of N-Methyl Piperazine Acetic Acids

Scheme B For The Synthesis Of N-Methyl Piperazine Acetic Acids

Scheme C For The Synthesis Of N-Methyl Piperazine Acetic Acids

Scheme A For The Synthesis Of $^{18}$O Labeled N-Methyl Piperazine Acetic Acids

Scheme B For The Synthesis Of $^{18}$O Labeled N-Methyl Piperazine Acetic Acids

Scheme A For The Synthesis Of Various Active Esters Of N-Methyl Piperazine
Via Imidazolide Formation Scheme B For The Synthesis Of Various Active Esters Of N-Methyl Piperazine Via Oxallyl Chloride Scheme C For The Synthesis Of Various Active Esters Of N-Methyl Piperazine Via Trifluroacetate Ester Scheme For The Synthesis Of Various Active Esters Of N-Methyl Piperazine Via Trifluoroacetate Esters Isotopic Pathway For Prepared N-Methyl Piperazine Acetic Acids Fragmentation of the Isobaric Label Set Possible Fragment Ion Structures Signature Ion 114 or

Signature Ion 115 or

Signature Ion 116 or

Signature Ion 117

General Fragmentation Properties Of The Set Of Isobaric Labeling Reagents

General Features of
Solid Phase Reagent

Cys- Capture Reagent

ISOBARICALLY LABELED ANALYTES AND FRAGMENT IONS DERIVED THEREFROM

CROSS REFERENCE TO RELATED APPLICATIONS

This application is a continuation and claims the right of priority under 35 U.S.C. §120 to U.S. patent application Ser. No. 10/852,730, filed May 24, 2004, incorporated herein by reference, which is a continuation-in-part of U.S. patent application Ser. No. 10/822,639, filed on Apr. 12, 2004, incorporated herein by reference, which is a continuation-in-part of U.S. patent application Ser. No. 10/751,353, filed on Jan. 5, 2004, incorporated herein by reference.

FIELD OF THE INVENTION

This invention pertains to mixtures of isobarically labeled analytes and fragment ions thereof.

INTRODUCTION

This invention pertains the determination of an analyte or analytes by mass analysis. An analyte can be any molecule of interest. Non-limiting examples of analytes include, but are not limited to, proteins, peptides, nucleic acids, carbohydrates, lipids, steroids and small molecules of less than 1500 daltons.

Analytes can be labeled by reaction of the analyte with a labeling reagent of the formula: RP-X-LK-Y-RG, a salt or salts thereof and/or a hydrate thereof, wherein RG is a reactive group that reacts with the analyte and RP, X, LK and Y are described in more detail below. A labeled analyte therefore can have the general formula: RP-X-LK-Y-Analyte. Sets of isomeric or isobaric labeling reagents can be used to label the analytes of two or more different samples wherein the labeling reagent can be different for each different sample and wherein the labeling reagent can comprise a unique reporter, "RP", that can be associated with the sample from which the labeled analyte originated. Hence, information, such as the presence and/or amount of the reporter, can be correlated with the presence and/or amount (often expressed as a concentration and/or quantity) of the analyte in a sample even from the analysis of a complex mixture of labeled analytes derived by mixing the products of the labeling of different samples. Analysis of such complex sample mixtures can be performed in a manner that allows for the determination of one or a plurality of analytes from the same or from multiple samples in a multiplex mariner. Thus, embodiments of this invention are particularly well suited for the multiplex analysis of complex sample mixtures. For example, embodiments of this invention can be used in proteomic analysis and/or genomic analysis as well as for correlation studies related to genomic and proteomic analysis.

For example, isotopically enriched N-substituted piperazines and N-substituted piperazine acetic acids can be used as intermediates in the synthesis of active esters of N-substituted piperazine acetic acid. Active esters are well known in peptide synthesis and refer to certain esters that are easily reacted with an amine of an amino acid under conditions commonly used in peptide synthesis (For a discussion of active esters please see: Innovation And Perspectives In Solid Phase Synthesis, Editor: Roger Epton, SPCC (UK) Ltd, Birmingham, 1990). A commonly used form of an active ester is the N-hydroxysuccinimidyl (NHS) ester.

The active esters of N-substituted piperazine acetic acid can be used as labeling reagents. In some embodiments, a set of isobaric (or isomeric) labeling reagents can be prepared. The set of isobaric labeling reagents can be used to label analytes, such as peptides, proteins, amino acids, oligonucleotides, DNA, RNA, lipids, carbohydrates, steroids, small molecules and the like. The labeled analytes can be mixed together and analyzed simultaneously in a mass spectrometer.

Because the heavy atom isotope distribution in each of the isobaric labeling reagents can be designed to result in the generation of a unique "signature ion" when analyzed in a mass spectrometer (MS), labeled components of the mixture associated with each of the labeling reagents, and by implication components of each labeling reaction used to produce the mixture, can be deconvoluted. Deconvolution can include determining the relative and/or absolute amount (often expressed in concentration or quantity) of one or more labeled components in each of the individual samples that were labeled and combined to form the mixture. The active esters of N-substituted piperazine acetic acid described herein therefore can be powerful tools for analyte analysis. Experimental analysis for which the isomeric and/or isobaric reagents can be used includes, but is not limited to, time course studies, biomarker analysis, multiplex proteomic analysis, mudpit experiments, affinity pull-downs, determination of post-translational modifications (PTMs) and multiple control experiments.

DEFINITIONS

Figure 1A:
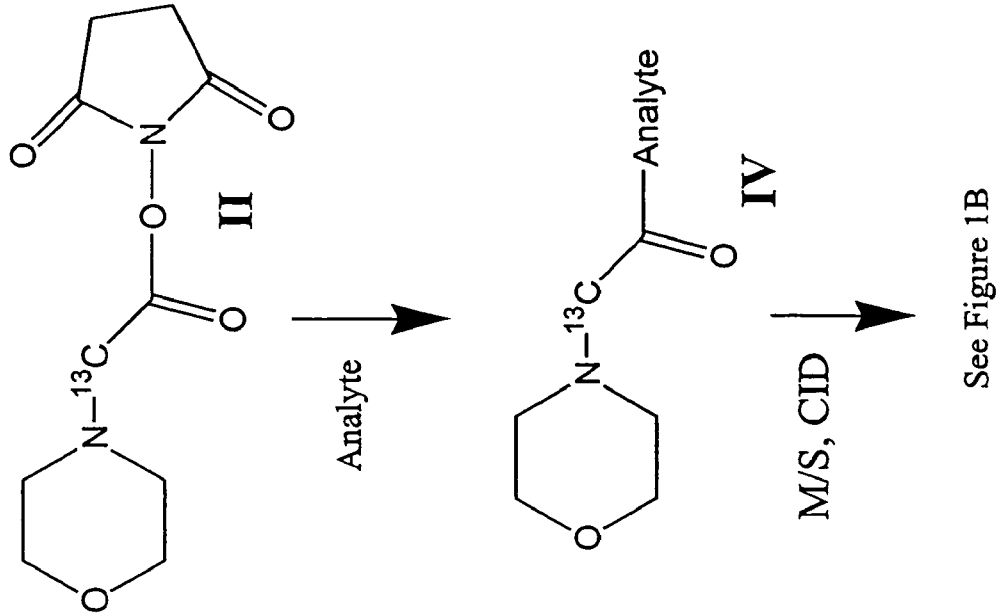
FIG. 1A illustrates the reaction of an analyte with two different isobaric labeling reagents (e.g. compounds I and II).

For the purposes of interpreting of this specification, the following definitions will apply and whenever appropriate, terms used in the singular will also include the plural and vice versa:

a.) As used herein, "analyte" refers to a molecule of interest that may be determined. Non-limiting examples of analytes include, but are not limited to, proteins, peptides, nucleic acids (both DNA or RNA), carbohydrates, lipids, steroids and other small molecules with a molecular weight of less than 1500 Daltons (Da). The source of the analyte, or the sample comprising the analyte, is not a limitation as it can come from any source. The analyte or analytes can be natural or synthetic. Non-limiting examples of sources for the analyte, or the sample comprising the analyte, include cells or tissues, or cultures (or subcultures) thereof. Non-limiting examples of analyte sources include, but are not limited to, crude or processed cell lysates, body fluids, tissue extracts, cell extracts or fractions (or portions) from a separations process such as a chromatographic separation, a 1D electrophoretic separation, a 2D electrophoretic separation or a capillary electrophoretic separation. Body fluids include, but are not limited to, blood, urine, feces, spinal fluid, cerebral fluid, amniotic fluid, lymph fluid or a fluid from a glandular secretion. By processed cell lysate we mean that the cell lysate is treated, in addition to the treatments needed to lyse the cell, to thereby perform additional processing of the collected material. For example, the sample can be a cell lysate comprising one or more analytes that are peptides formed by treatment of the cell lysate with a proteolytic enzyme to thereby digest precursor peptides and/or proteins.

b.) As used herein with respect to a compound, "light" refers to the compound as not being enriched with a heavy atom isotope. As used herein with respect to a compound "heavy" refers to the compound as being enriched with at least one heavy atom isotope.

c.) Except as when clearly not intended based upon the context in which it is being used (e.g. when made in reference to a structure that dictates otherwise), "ester" refers to both an ester and/or a thioester.

d.) It is well accepted that the mass of an atom or molecule can be approximated, often to the nearest whole number atomic mass unit or the nearest tenth or hundredth of an atomic mass unit. As used herein, "gross mass" refers to the absolute mass as well as to the approximate mass within a range where the use of isotopes of different atom types are so close in mass that they are the functional equivalent for the purpose of balancing the mass of the reporter and/or linker moieties (so that the gross mass of the reporter/linker combination is the same within a set or kit of isobaric or isomeric labeling reagents) whether or not the very small difference in mass of the different isotopes types used can be detected.

For example, the common isotopes of oxygen have a gross mass of 16.0 (actual mass 15.9949) and 18.0 (actual mass 17.9992), the common isotopes of carbon have a gross mass of 12.0 (actual mass 12.00000) and 13.0 (actual mass 13.00336) and the common isotopes of nitrogen have a gross mass of 14.0 (actual mass 14.0031) and 15.0 (actual mass 15.0001). Whilst these values are approximate, one of skill in the art will appreciate that if one uses the $^{18}$O isotope in one reporter of a set, the additional 2 mass units (over the isotope of oxygen having a gross mass of 16.0) can, for example, be compensated for in a different reporter of the set comprising $^{16}$O by incorporating, elsewhere in the reporter, two carbon $^{13}$C atoms, instead of two $^{12}$C atoms, two $^{15}$N atoms, instead of two $^{14}$N atoms or even one $^{13}$C atom and one $^{15}$N atom, instead of a $^{12}$C and a $^{14}$N, to compensate for the $^{18}$O. In this way the two different reporters of the set are the functional mass equivalent (i.e. have the same gross mass) since the very small actual differences in mass between the use of two $^{13}$C atoms (instead of two $^{12}$C atoms), two $^{15}$N atoms (instead of two $^{14}$N atoms), one $^{13}$C and one $^{15}$N (instead of a $^{12}$C and $^{14}$N) or one $^{18}$O atom (instead of one $^{16}$O atom), to thereby achieve an increase in mass of two Daltons, in all of the labels of the set or kit, is not an impediment to the nature of the analysis.

Figure 8:
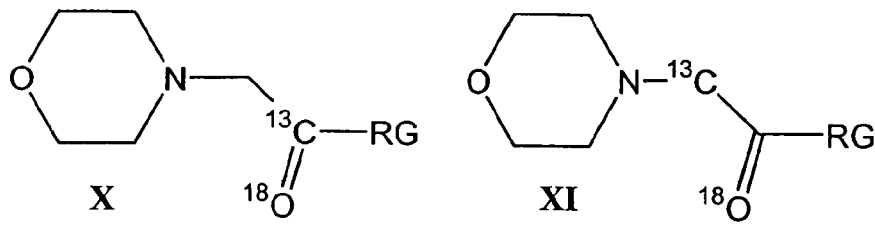
FIG. 8 is an illustration of two sets of isobaric labeling reagents wherein the same isotopes (compounds X-XIII) and different isotopes (compounds XV-XVIII) are used within the set to thereby achieve reporter/linker moieties of the same gross mass but each with a reporter moiety of a different gross mass within the set.
Figure 8:
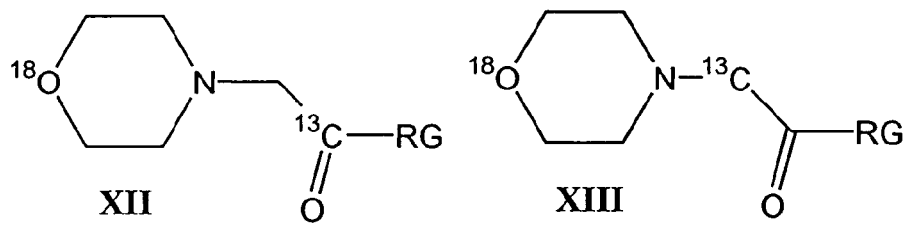
Figure 8:
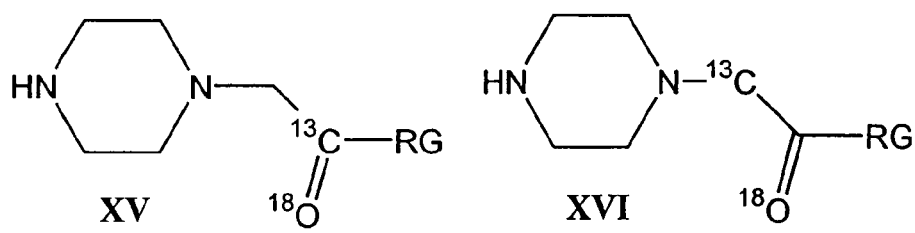
Figure 8:
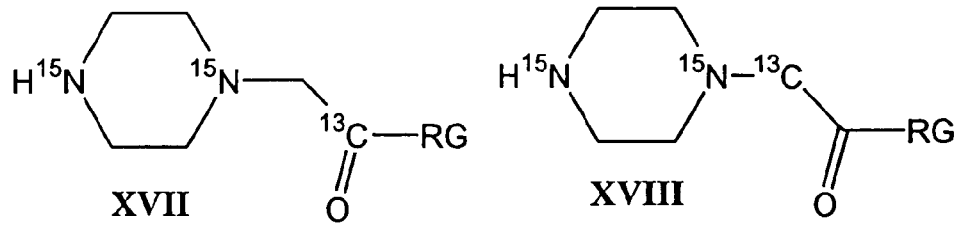

This can be illustrated with reference to FIG. 8. In FIG. 8, the reporter/linker combination of compound XVII (FIG. 8; chemical formula: $C_5{}^{13}CH_{10}{}^{15}N_2O$) has two $^{15}$N atoms and one $^{13}$C atom and a total theoretical mass of 129.138. By comparison, isobar XV (FIG. 8; chemical formula $C_5{}^{13}CH_{10}N_2{}^{18}O$) has one $^{18}$O atom and one $^{13}$C atom and a total theoretical mass of 129.151. Compounds XVII and XV are isobars that are structurally and chemically indistinguishable, except for heavy atom isotope content, although there is a slight absolute mass difference (mass 129.138 vs. mass 129.151 respectively). However, the gross mass of compounds XVII and XV is 129.1 for the purposes of this invention since this is not an impediment to the analysis whether or not the mass spectrometer is sensitive enough to measure the small difference between the absolute mass of isobars XVII and XV.

From FIG. 8, it is clear that the distribution of the same heavy atom isotopes within a structure is not the only consideration for the creation of sets of isomeric and/or isobaric labeling reagents. It is possible to mix heavy atom isotope types to achieve isomers or isobars of a desired gross mass. In this way, both the selection (combination) of heavy atom isotopes as well as their distribution is available for consideration in the production of the isomeric and/or isobaric labeling reagents useful for embodiments of this invention.

e.) As used herein, "fragmentation" refers to the breaking of a covalent bond.

f.) As used herein, "fragment" refers to a product of fragmentation (noun) or the operation of causing fragmentation (verb).

g.) As used herein with respect to a compound, "isotopically enriched" means that the compound (e.g. labeling reagent) has been enriched synthetically with one or more heavy atom isotopes (e.g. stable isotopes such as Deuterium, $^{13}$C, $^{15}$N, $^{18}$O, $^{37}$Cl or $^{81}$Br). By "enriched" we mean that the amount of heavy atom isotope exceeds that normally found in naturally formed compositions. Because isotopic enrichment is not 100% effective, there can be impurities of the compound that are of lesser states of enrichment and these will have a lower mass. Likewise, because of over-enrichment (undesired enrichment) and because of natural isotopic abundance, there can be impurities of greater mass.

h.) As used herein, "labeling reagent" refers to a moiety suitable to mark an analyte for determination. The term label is synonymous with the terms tag and mark and other equivalent terms and phrases. For example, a labeled analyte can be referred to as a tagged analyte or a marked analyte.

i.) As used herein, "natural isotopic abundance" refers to the level (or distribution) of one or more isotopes found in a compound based upon the natural prevalence of an isotope or isotopes in nature. For example, a natural compound obtained from living plant matter will typically contain about 0.6% $^{13}$C.

j.) As used herein, isobars are structurally and chemically indistinguishable compounds (except for isotopic content and/or distribution) of the same nominal gross mass. By comparison, isomers are structurally and/or chemically distinguishable compounds of the same nominal gross mass.

k.) As used herein, "support", "solid support", "solid carrier" or "solid phase" refers to any solid phase material upon which a labeling reagent can be immobilized. Immobilization can, for example, be used to label analytes or be used to prepare a labeling reagent, whether or not the labeling occurs on the support. Support encompasses terms such as "resin", "synthesis support", "solid phase", "surface" "membrane" and/or "support". A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled-pore-glass (CPG), or reverse-phase silica. The configuration of a solid support can be in the form of beads, spheres, particles, granules, a gel, a membrane or a surface. Surfaces can be planar, substantially planar, or non-planar. Supports can be porous or non-porous, and can have swelling or non-swelling characteristics. A support can be configured in the form of a well, depression or other container, vessel, feature or location. A plurality of supports can be configured in an array at various locations, addressable for robotic delivery of reagents, or by detection methods and/or instruments.

DESCRIPTION OF VARIOUS EMBODIMENTS OF THE INVENTION

I. General

The Reactive Group:

The reactive group "RG" of the labeling reagent or reagents used in the method, mixture, kit and/or composition embodiments can be either an electrophile or a nucleophile that is capable of reacting with one or more reactive analytes of a sample. The reactive group can be preexisting or it can be prepared in-situ. In-situ preparation of the reactive group can proceed in the absence of the reactive analyte or it can proceed in the presence of the reactive analyte. For example, a carboxylic acid group can be modified in-situ with water-soluble carbodiimide (e.g. 1-(3-dimethylaminopropyl)-3-ethylcarbodiimide hydrochloride; EDC) to thereby prepare an electrophilic group that can be reacted with a nucleophile such as an alkyl or aryl amine group. In some embodiments, activation of the carboxylic acid group of a labeling reagent with EDC can be performed in the presence of an amine (nucleophile) containing analyte. In some embodiments, the amine (nucleophile) containing analyte can also be added after the initial reaction with EDC is performed. In other embodiments, the reactive group can be generated in-situ by the in-situ removal of a protecting group. Consequently, any existing or newly created reagent or reagents that can effect the derivatization of analytes by the reaction of nucleophiles and/or electrophiles are contemplated by the method, mixture, kit and/or composition embodiments of this invention.

Where the reactive group of the labeling reagent is an electrophile, it can react with a suitable nucleophilic group of the analyte or analytes. Where the reactive group of the labeling reagent is a nucleophile, it can react with a suitable electrophilic group of the analyte or analytes. Numerous pairs of suitable nucleophilic groups and electrophilic groups are known and often used in the chemical and biochemical arts. Non-limiting examples of reagents comprising suitable nucleophilic or electrophilic groups that can be coupled to analytes (e.g. such as proteins, peptides, nucleic acids, carbohydrates, lipids, steroids or other small molecules of less that 1500 daltons) to effect their derivatization, are described in the Pierce Life Science & Analytical Research Products Catalog & Handbook (a Perstorp Biotec Company), Rockford, Ill. 61105, USA. Other suitable reagents are well known in the art and are commercially available from numerous other vendors such as Sigma-Aldrich.

The reactive group of a labeling reagent can be an amine reactive group. For example the amine reactive group can be an active ester. Active esters are well known in peptide synthesis and refer to certain esters that are easily reacted with the N-α amine of an amino acid under conditions commonly used in peptide synthesis. The amine reactive active ester can be an N-hydroxysuccinimidyl ester (NHS), a N-hydroxysulfosuccinimidyl ester, a pentafluorophenyl ester (Pfp), a 2-nitrophenyl ester, a 4-nitrophenyl ester, a 2,4-dinitrophenylester or a 2,4-dihalophenyl ester. For example, the alcohol or thiol group of an active ester can have the formula:

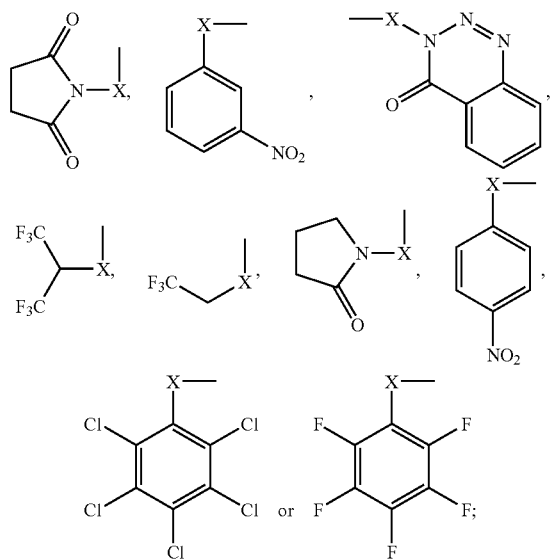

wherein X is O or S, but preferably O. All of the foregoing being alcohol or thiol groups known to form active esters in the field of peptide chemistry wherein said alcohol or thiol group is displaced by the reaction of the N-α-amine of the amino acid with the carbonyl carbon of the ester. It should be apparent that the active ester (e.g. N-hydroxysuccinimidyl ester) of any suitable labelling/tagging reagent described herein could be prepared using well-known procedures (See: Greg T. Hermanson (1996). "The Chemistry of Reactive Group" in "Bioconjugate Techniques" Chapter 2 pages 137-165, Academic Press, (New York); also see: Innovation And Perspectives In Solid Phase Synthesis, Editor: Roger Epton, SPCC (UK) Ltd, Birmingham, 1990). Methods for the formation of active esters of N-substituted piperazine acetic acids compounds that are representative examples of labeling reagents of the general formula: RP-X-LK-Y-RG, are described in detail below.

In another embodiment, the reactive group of the labeling reagent can be a mixed anhydride since mixed anhydrides are known to efficiently react with amine groups to thereby produce amide bonds.

The reactive group of a labeling reagent can be a thiol reactive group. For example, the thiol reactive group can be a malemide, an alkyl halide, an aryl halide of an α-halo-acyl, and α-halo thione or and α-halo imine. By halide or halo we mean atoms of fluorine, chlorine, bromine or iodine.

The reactive group of a labeling reagent can be a hydroxyl reactive group. For example, the hydroxyl reactive group can be a trityl-halide or a silyl-halide reactive moiety. The trityl-halide reactive moieties can be substituted (e.g. Y-methoxytrityl, Y-dimethoxytrityl, Y-trimethoxytrityl, etc) or unsubstituted wherein Y is defined below. The silyl reactive moieties can be alkyl substituted silyl halides, such as Y-dimethylsilyl, Y-ditriethylsilyl, Y-dipropylsilyl, Y-diisopropylsilyl, etc.) wherein Y is defined below.

The reactive group of the labeling reagent can be a nucleophile such as an amine group, a hydroxyl group or a thiol group.

The Reporter Moiety:

The reporter moiety of the labeling reagent or reagents used in embodiments of this invention can be a group that has a unique mass (or mass to charge ratio) that can be determined. Accordingly, each reporter of a set can have a unique gross mass. Different reporters can comprise one or more heavy atom isotopes to achieve their unique mass. For example, isotopes of carbon ($^{12}C$, $^{13}C$ and $^{14}C$), nitrogen ($^{14}N$ and $^{15}N$), oxygen ($^{16}O$ and $^{18}O$) or hydrogen (hydrogen, deuterium and tritium) exist and can be used in the preparation of a diverse group of reporter moieties. Examples of stable heavy atom isotopes include $^{13}C$, $^{15}N$, $^{18}O$ and deuterium. These are not limiting as other light and heavy atom isotopes can also be used in the reporter. Basic starting materials suitable for preparing reporters comprising light and heavy atom isotopes are available from various commercial sources such as Cambridge Isotope Laboratories, Andover, Mass. (See: list or "basic starting materials" at www.isotope.com) and Isotec (a division of Sigma-Aldrich). Cambridge Isotope Laboratories and Isotec will also prepare desired compounds under custom synthesis contracts. Id.

A unique reporter can be associated with a sample of interest thereby labeling one or multiple analytes of that sample with the reporter. In this way information about the reporter can be associated with information about one or all of the analytes of the sample. However, the reporter need not be physically linked to an analyte when the reporter is determined. Rather, the unique gross mass of the reporter can, for example, be determined in a second mass analysis of a tandem mass analyzer, after ions of the labeled analyte are fragmented to thereby produce daughter fragment ions and detectable reporters. The determined reporter can be used to identify the sample from which a determined analyte originated. Further, the amount of the unique reporter, either relative to the amount of other reporters or relative to a calibration standard (e.g. an analyte labeled with a specific reporter), can be used to determine the relative or absolute amount (often expressed as a concentration and/or quantity) of analyte in the sample or samples. Therefore information, such as the amount of one or more analytes in a particular sample, can be associated with the reporter moiety that is used to label each particular sample. Where the identity of the analyte or analytes is also determined, that information can be correlated with information pertaining to the different reporters to thereby facilitate the determination of the identity and amount of each labeled analyte in one or a plurality of samples.

The reporter can either comprises a fixed charge or can be capable of becoming ionized. Because the reporter can either comprises a fixed charge or can be capable of being ionized, the labeling reagent might be isolated or used to label the reactive analyte in a salt (or a mixture of salts) or zwitterionic form. Ionization of the reporter facilitates its determination in a mass spectrometer. Accordingly, the reporter can be determined as an ion, sometimes referred to as a signature ion. When ionized, the reporter can comprise one or more net positive or negative charges. Thus, the reporter can comprise one or more acidic groups or basic groups since such groups can be easily ionized in a mass spectrometer. For example, the reporter can comprise one or more basic nitrogen atoms (positive charge) or one or more ionizable acidic groups such as a carboxylic acid group, sulfonic acid group or phosphoric acid group (negative charge). Non-limiting examples of reporters comprising a basic nitrogen include, substituted or unsubstituted, morpholines, piperidines or piperazines.

The reporter can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocylic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

The reporter can be selected so that it does not substantially sub-fragment under conditions typical for the analysis of the analyte. The reporter can be chosen so that it does not substantially sub-fragment under conditions of dissociative energy applied to cause fragmentation of both bonds X and Y of at least a portion of selected ions of a labeled analyte in a mass spectrometer. By "does not substantially sub-fragment" we mean that fragments of the reporter are difficult or impossible to detect above background noise when applied to the successful analysis of the analyte of interest. The gross mass of a reporter can be intentionally selected to be different as compared with the mass of the analyte sought to be determined or any of the expected fragments of the analyte. For example, where proteins or peptides are the analytes, the reporter's gross mass can be chosen to be different as compared with any naturally occurring amino acid or peptide, or expected fragments thereof. This can facilitate analyte determination since, depending on the analyte, the lack of any possible components of the sample having the same coincident mass can add confidence to the result of any analysis. Examples of mass ranges where little background can be expected for peptides can be found in Table 1.

TABLE 1

Possible "Quiet Zones" For Selection Of Label Fragment Ion m/z
M/z start-end

| 10-14 |
| 19-22 |
| 24-26 |
| 31-38 |

TABLE 1-continued

Possible "Quiet Zones" For Selection Of Label Fragment Ion m/z
M/z start-end

| 40-40 |
| 46-50 |
| 52-52 |
| 58-58 |
| 61-69 |
| 71-71 |
| 74-83 |
| 89-97 |
| 103-109 |
| 113-119 |
| 121-125 |
| 128-128 |
| 131-135 |
| 137-147 |
| 149-154 |
| 156-156 |
| 160-174 |
| 177-182 |
| 184-184 |
| 188-189 |
| 191-191 |
| 202-207 |
| 210-210 |
| 216-222 |
| 224-226 |

Figure 6:
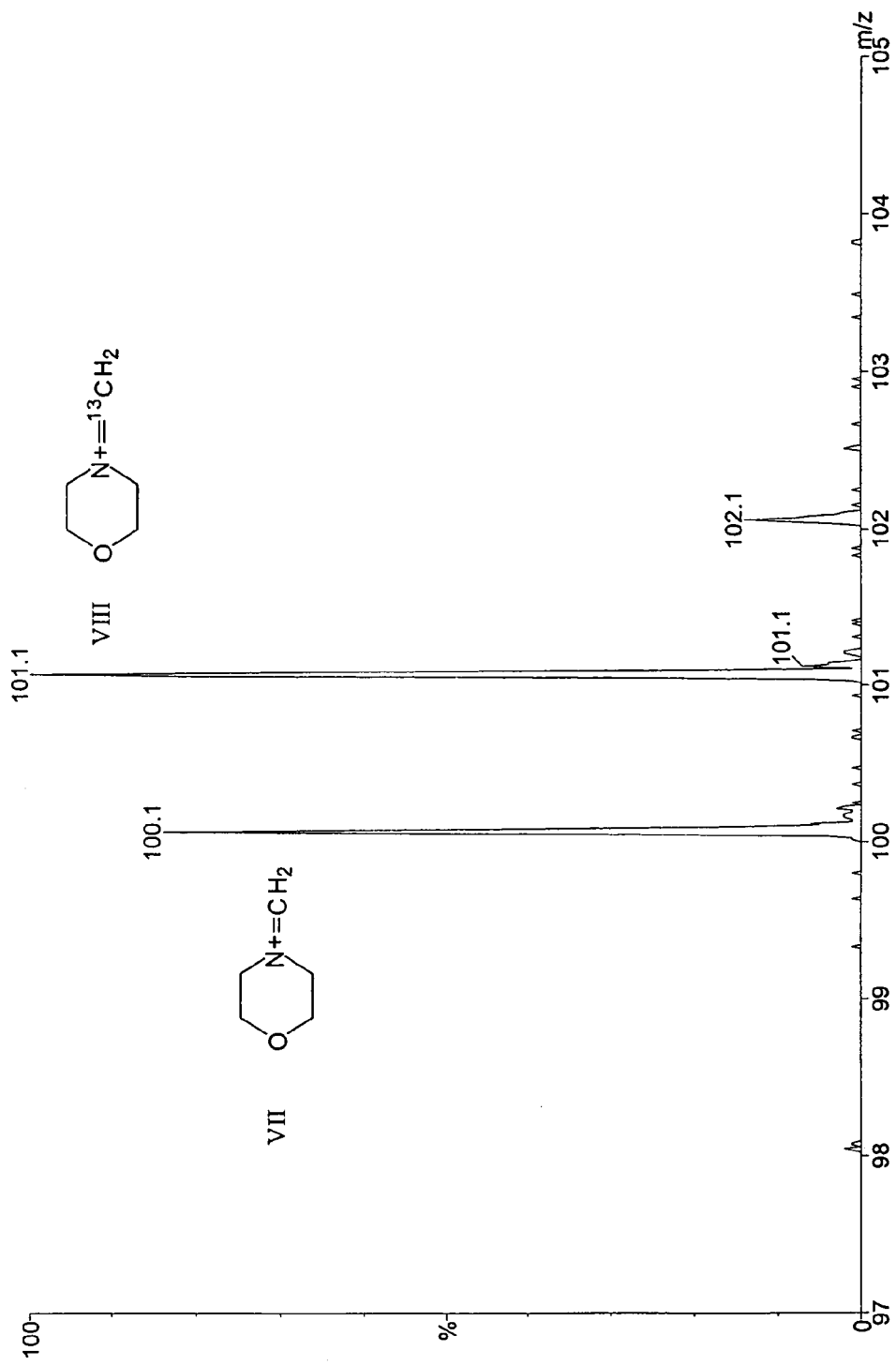
FIG. 6 is an expansion plot of a mass spectrum of two reporters (i.e. signature ions) as determined in the second mass analysis.

The reporter can be a small molecule that is non-polymeric. The reporter does not have to be a biopolymer (e.g. a peptide, a protein or a nucleic acid) or a component of a biopolymer (e.g. an amino acid, a nucleoside or a nucleotide). The gross mass of a reporter can be less than 250 Daltons. Such a small molecule can be easily determined in the second mass analysis, free from other components of the sample having the same coincident mass in the first mass analysis. In this context, the second mass analysis can be performed, typically in a tandem mass spectrometer, on selected ions that are determined in the first mass analysis. Because ions of a particular mass to charge ratio can be specifically selected out of the first mass analysis for possible fragmentation and further mass analysis, the non-selected ions from the first mass analysis are not carried forward to the second mass analysis and therefore do not contaminate the spectrum of the second mass analysis. Furthermore, the sensitivity of a mass spectrometer and the linearity of the detector (for purposes of quantitation) can be quite robust in this low mass range. Additionally, the present state of mass spectrometer technology can allow for baseline mass resolution of less than one Dalton in this mass range (See for example: FIG. 6). These factors may prove to be useful advancements to the state of the art.

The Linker Moiety:

The linker moiety of the labeling reagent or reagents used with embodiments of this invention links the reporter to the analyte or the reporter to the reactive group depending on whether or not a reaction with the analyte has occurred. The linker can be selected to produce a neutral species when both bonds X and Y are fragmented (i.e. undergoes neutral loss upon fragmentation of both bonds X and Y). The linker can be a very small moiety such as a carbonyl or thiocarbonyl group. For example, the linker can comprise at least one heavy atom isotope and comprise the formula:

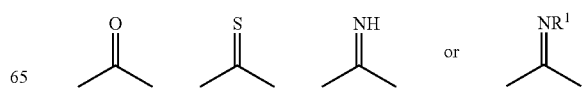

wherein $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms. The linker can be a larger moiety. The linker can be a polymer or a biopolymer. The linker can be designed to sub-fragment when subjected to dissociative energy levels; including sub-fragmentation to thereby produce only neutral fragments of the linker.

The linker moiety can comprise one or more heavy atom isotopes such that its mass compensates for the difference in gross mass between the reporters for each labeled analyte of a mixture or for the reagents of set and/or kit. Moreover, the aggregate gross mass (i.e. the gross mass taken as a whole) of the reporter/linker combination can be the same for each labeled analyte of a mixture or for the reagents of set and/or kit. More specifically, the linker moiety can compensate for the difference in gross mass between reporters of labeled analytes from different samples wherein the unique gross mass of the reporter correlates with the sample from which the labeled analyte originated and the aggregate gross mass of the reporter/linker combination is the same for each labeled analyte of a sample mixture regardless of the sample from which it originated. In this way, the gross mass of identical analytes in two or more different samples can have the same gross mass when labeled and then mixed to produce a sample mixture.

For example, the labeled analytes, or the reagents of a set and/or kit for labeling the analytes, can be isomers or isobars. Thus, if ions of a particular mass to charge ratio (taken from the sample mixture) are selected (i.e. selected ions) in a mass spectrometer from an initial mass analysis of the sample mixture, identical analytes from the different samples that make up the sample mixture are represented in the selected ions in proportion to their respective concentration and/or quantity in the sample mixture. Accordingly, the linker not only links the reporter to the analyte, it also can serve to compensate for the differing masses of the unique reporter moieties to thereby harmonize the gross mass of the reporter/linker combination in the labeled analytes of the various samples.

Because the linker can act as a mass balance for the reporter in the labeling reagents, such that the aggregate gross mass of the reporter/linker combination is the same for all reagents of a set or kit, the greater the number of atoms in the linker, the greater the possible number of different isomeric/isobaric labeling reagents of a set and/or kit. Stated differently, generally the greater the number of atoms that a linker comprises, the greater number of potential reporter/linker combinations exist since isotopes can be substituted at most any position in the linker to thereby produce isomers or isobars of the linker portion wherein the linker portion is used to offset the differing masses of the reporter portion and thereby create a set of reporter/linker isomers or isobars. Such diverse sets of labeling reagents are particularly well suited for multiplex analysis of analytes in the same and/or different samples.

The total number of labeling reagents of a set and/or kit can be two, three, four, five, six, seven, eight, nine, ten, eleven, twelve, thirteen, fourteen, fifteen, sixteen or more. The diversity of the labeling reagents of a set or kit is limited only by the number of atoms of the reporter and linker moieties, the heavy atom isotopes available to substitute for the light isotopes and the various synthetic configurations in which the isotopes can be synthetically placed. As suggested above however, numerous isotopically enriched basic starting materials are readily available from manufacturers such as Cambridge Isotope Laboratories and Isotec. Such isotopically enriched basic starting materials can be used in the synthetic processes used to produce sets of isobaric and isomeric labeling reagents or be used to produce the isotopically enriched starting materials that can be used in the synthetic processes used to produce sets of isobaric and isomeric labeling reagents. Some examples of the preparation of isobaric labeling reagents suitable for use in a set of labeling reagents are discussed in more detail below.

The Reporter/Linker Combination:

The labeling reagents described herein comprise reporters and linkers that are linked through the bond X. As described above, the reporter/linker combination can be identical in gross mass for each member of a set and/or kit of labeling reagents. Moreover, bond X of the reporter/linker combination of the labeling reagents can be designed to fragment, in at least a portion of the selected ions, when subjected to dissociative energy levels thereby releasing the reporter from the linker and/or analyte. Accordingly, the gross mass of the reporter (as a m/s ratio) and its intensity can be observed directly in MS/MS analysis.

The reporter/linker combination can comprise various combinations of the same or different heavy atom isotopes amongst the various labeling reagents of a set or kit. In the scientific literature this has sometimes been referred to as coding or isotope coding. For example, Abersold et al. has disclosed the isotope coded affinity tag (ICAT; see WO00/11208). In one respect, the reagents of Abersold et al. differ from the labeling reagents of this invention in that Abersold does not teach two or more same mass labeling reagents such as isomeric or isobaric labeling reagents.

Mass Spectrometers/Mass Spectrometry (MS):

The methods of this invention can be practiced using tandem mass spectrometers and other mass spectrometers that have the ability to select and fragment molecular ions. Tandem mass spectrometers (and to a lesser degree single-stage mass spectrometers) have the ability to select and fragment molecular ions according to their mass-to-charge (m/z) ratio, and then record the resulting fragment (daughter) ion spectra. More specifically, daughter fragment ion spectra can be generated by subjecting selected ions to dissociative energy levels (e.g. collision-induced dissociation (CID)). For example, ions corresponding to labeled peptides of a particular m/z ratio can be selected from a first mass analysis, fragmented and reanalyzed in a second mass analysis. Representative instruments that can perform such tandem mass analysis include, but are not limited to, magnetic four-sector, tandem time-of-flight, triple quadrupole, ion-trap, and hybrid quadrupole time-of-flight (Q-TOF) mass spectrometers.

These types of mass spectrometers may be used in conjunction with a variety of ionization sources, including, but not limited to, electrospray ionization (ESI) and matrix-assisted laser desorption ionization (MALDI). Ionization sources can be used to generate charged species for the first mass analysis where the analytes do not already possess a fixed charge. Additional mass spectrometry instruments and fragmentation methods include post-source decay in MALDI-MS instruments and high-energy CID using MALDI-TOF (time of flight)-TOF MS. For a recent review of tandem mass spectrometers please see: R. Aebersold and D. Goodlett, *Mass Spectrometry in Proteomics. Chem. Rev.* 101: 269-295 (2001). Also see U.S. Pat. No. 6,319,476, herein incorporated by reference, for a discussion of TOF-TOF mass analysis techniques.

Fragmentation by Dissociative Energy Levels:

It is well accepted that bonds can fragment as a result of the processes occurring in a mass spectrometer. Moreover, bond fragmentation can be induced in a mass spectrometer by subjecting ions to dissociative energy levels. For example, the dissociative energy levels can be produced in a mass spectrometer by collision-induced dissociation (CID). Those of ordinary skill in the art of mass spectrometry will appreciate that other exemplary techniques for imposing dissociative energy levels that cause fragmentation include, but are not limited to, photo dissociation, electron capture and surface induced dissociation.

The process of fragmenting bonds by collision-induced dissociation involves increasing the kinetic energy state of selected ions, through collision with an inert gas, to a point where bond fragmentation occurs. For example, kinetic energy can be transferred by collision with an inert gas (such as nitrogen, helium or argon) in a collision cell. The amount of kinetic energy that can be transferred to the ions is proportional to the number of gas molecules that are allowed to enter the collision cell. When more gas molecules are present, a greater amount of kinetic energy can be transferred to the selected ions, and less kinetic energy is transferred when there are fewer gas molecules present.

It is therefore clear that the dissociative energy level in a mass spectrometer can be controlled. It is also well accepted that certain bonds are more labile than other bonds. The lability of the bonds in an analyte or the reporter/linker moiety depends upon the nature of the analyte or the reporter/linker moiety. Accordingly, the dissociative energy levels can be adjusted so that the analytes and/or the labels (e.g. the reporter/linker combinations) can be fragmented in a manner that is determinable. One of skill in the art will appreciate how to make such routine adjustments to the components of a mass spectrometer to thereby achieve the appropriate level of dissociative energy to thereby fragment at least a portion of ions of labeled analytes into ionized reporter moieties and daughter fragment ions.

For example, dissociative energy can be applied to ions that are selected/isolated from the first mass analysis. In a tandem mass spectrometer, the extracted ions can be subjected to dissociative energy levels and then transferred to a second mass analyzer. The selected ions can have a selected mass to charge ratio. The mass to charge ratio can be within a range of mass to charge ratios depending upon the characteristics of the mass spectrometer. When collision induced dissociation is used, the ions can be transferred from the first to the second mass analyzer by passing them through a collision cell where the dissociative energy can be applied to thereby produce fragment ions. For example the ions sent to the second mass analyzer for analysis can include some, or a portion, of the remaining (unfragmented) selected ions, as well as reporter ions (signature ions) and daughter fragment ions of the labeled analyte.

Analyte Determination by Computer Assisted Database Analysis:

In some embodiments, analytes can be determined based upon daughter-ion fragmentation patterns that are analyzed by computer-assisted comparison with the spectra of known or "theoretical" analytes. For example, the daughter fragment ion spectrum of a peptide ion fragmented under conditions of low energy CID can be considered the sum of many discrete fragmentation events. The common nomenclature differentiates daughter fragment ions according to the amide bond that breaks and the peptide fragment that retains charge following bond fission. Charge-retention on the N-terminal side of the fissile amide bond results in the formation of a b-type ion. If the charge remains on the C-terminal side of the broken amide bond, then the fragment ion is referred to as a y-type ion. In addition to b- and y-type ions, the CID mass spectrum may contain other diagnostic fragment ions (daughter fragment ions). These include ions generated by neutral loss of ammonia (−17 amu) from glutamine, lysine and arginine or the loss of water (−18 amu) from hydroxyl-containing amino acids such as serine and threonine. Certain amino acids have been observed to fragment more readily under conditions of low-energy CID than others. This is particularly apparent for peptides containing proline or aspartic acid residues, and even more so at aspartyl-proline bonds (Mak, M. et al., *Rapid Commun. Mass Spectrom.*, 12: 837-842) (1998). Accordingly, the peptide bond of a Z-pro dimer or Z-asp dimer, wherein Z is any natural amino acid, pro is proline and asp is aspartic acid, will tend to be more labile as compared with the peptide bond between all other amino acid dimer combinations.

For peptide and protein samples therefore, low-energy CID spectra contain redundant sequence-specific information in overlapping b- and y-series ions, internal fragment ions from the same peptide, and immonium and other neutral-loss ions. Interpreting such CID spectra to assemble the amino acid sequence of the parent peptide de novo is challenging and time-consuming. The most significant advances in identifying peptide sequences have been the development of computer algorithms that correlate peptide CID spectra with peptide sequences that already exist in protein and DNA sequence databases. Such approaches are exemplified by programs such as SEQUEST (Eng, J. et al. *J. Am. Soc. Mass Spectrom.*, 5: 976-989 (1994)) and MASCOT (Perkins, D. et al. *Electrophoresis*, 20: 3551-3567 (1999)).

In brief, experimental peptide CID spectra (MS/MS spectra) are matched or correlated with 'theoretical' daughter fragment ion spectra computationally generated from peptide sequences obtained from protein or genome sequence databases. The match or correlation is based upon the similarities between the expected mass and the observed mass of the daughter fragment ions in MS/MS mode. The potential match or correlation is scored according to how well the experimental and 'theoretical' fragment patterns coincide. The constraints on databases searching for a given peptide amino acid sequence are so discriminating that a single peptide CID spectrum can be adequate for identifying any given protein in a whole-genome or expressed sequence tag (EST) database. For other reviews please see: Yates, J. R. Trends, *Genetics*, 16: 5-8 (2000) and Yates, J. R., *Electrophoresis* 19: 893-900 (1998).

Accordingly, daughter fragment ion analysis of MS/MS spectra can be used not only to determine the analyte of a labeled analyte, it can also be used to determine analytes from which the determined analyte originated. For example, identification of a peptide in the MS/MS analysis can be can be used to determine the protein from which the peptide was cleaved as a consequence of an enzymatic digestion of the protein. It is envisioned that such analysis can be applied to other analytes, such as nucleic acids.

Bonds X and Y:

X is a bond between an atom of the reporter and an atom of the linker. Y is a bond between an atom of the linker and an atom of either the reactive group or, if the labeling reagent has been reacted with a reactive analyte, the analyte. Bonds X and Y of the various labeling reagents (i.e. RP-X-LK-Y-RG) that can be used in the embodiments of this invention can fragment, in at least a portion of selected ions, when subjected to dissociative energy levels. Therefore, the dissociative energy level can be adjusted in a mass spectrometer so that both bonds X and Y fragment in at least a portion of the selected ions of the labeled analytes (i.e. RP-X-LK-Y-Analyte). Fragmentation of bond X releases the reporter from the analyte so that the reporter can be determined independently from the analyte. Fragmentation of bond Y releases the reporter/linker combination from the analyte, or the linker from the analyte, depending on whether or not bond X has already been fragmented. Bond Y can be more labile than bond X. Bond X can be more labile than bond Y. Bonds X and Y can be of the same relative lability.

When the analyte of interest is a protein or peptide, the relative lability of bonds X and Y can be adjusted with regard to an amide (peptide) bond. Bond X, bond Y or both bonds X and Y can be more, equal or less labile as compared with a typical amide (peptide) bond. For example, under conditions of dissociative energy, bond X and/or bond Y can be less prone to fragmentation as compared with the peptide bond of a Z-pro dimer or Z-asp dimer, wherein Z is any natural amino acid, pro is proline and asp is aspartic acid. In some embodiments, bonds X and Y will fragment with approximately the same level of dissociative energy as a typical amide bond. In some embodiments, bonds X and Y will fragment at a greater level of dissociative energy as compared with a typical amide bond.

Bonds X and Y can also exist such that fragmentation of bond Y results in the fragmentation of bond X, and vice versa. In this way, both bonds X and Y can fragment essentially simultaneously such that no substantial amount of analyte, or daughter fragment ion thereof, comprises a partial label in the second mass analysis. By "substantial amount of analyte" we mean that less than 25%, and preferably less than 10%, partially labeled analyte can be determined in the MS/MS spectrum.

Because there can be a clear demarcation between labeled and unlabeled fragments of the analyte in the spectra of the second mass analysis (MS/MS), this feature can simplify the identification of the analytes from computer assisted analysis of the daughter fragment ion spectra. Moreover, because the fragment ions of analytes can, in some embodiments, be either fully labeled or unlabeled (but not partially labeled) with the reporter/linker moiety, there can be little or no scatter in the masses of the daughter fragment ions caused by isotopic distribution across fractured bonds such as would be the case where isotopes were present on each side of a single labile bond of a partially labeled analyte routinely determined in the second mass analysis.

The Labeling of Analytes:

Analytes can be labeled by reacting a functional group of the analyte with the reactive group (RG) of the labeling reagent. As discussed previously, the functional group on the analyte can be one of an electrophile or a nucleophile and the functional group (i.e. the RG or reactive group) of the labeling reagent can be the other of the electrophile or a nucleophile. The electrophile and nucleophile can react to form a covalent link between the analyte and the labeling reagent.

The labeling reaction can take place in solution. In some embodiments, one of the analyte or the labeling reagent can be support bound. The labeling reaction can sometimes be performed in aqueous conditions. Aqueous conditions can be selected for the labeling of biomolecules such as proteins, peptides and nucleic acids. The labeling reaction can sometimes be performed in organic solvent or a mixture of organic solvents. Organic solvents can be selected for analytes that are small molecules. Mixtures of water and organic solvent or organic solvents can be used across a broad range. For example, a solution of water and from about 60 percent to about 95 percent organic solvent or solvents (v/v) can be prepared and used for labeling the analyte. In some embodiments, a solution of water and from about 65 percent to about 80 percent organic solvent or solvents (v/v) can be prepared and used for labeling the analyte. Non-limiting examples of organic solvents include N,N'-dimethylformamide (DMF), acetonitrile (ACN), and alcohol such as methanol, ethanol, propanol and/or butanol.

When performing a labeling reaction, the pH can be modulated. The pH can be in the range of 4-10. The pH can be outside this range. Generally, the basicity of non-aqueous reactions can be modulated by the addition of non-nucleophilic organic bases. Non-limiting examples of suitable bases include N-methylmorpholine, triethylamine and N,N-diisopropylethylamine. Alternatively, the pH of water containing solvents can be modulated using biological buffers such as (N-[2-hydroxyethyl]piperazine-N'[2-ethanesulfonic acid) (HEPES) or 4-morpholineethane-sulfonic acid (MES) or inorganic buffers such as sodium carbonate and/or sodium bicarbonate. Because at least one of the reactive groups can be electrophilic, it can be desirable to select the buffer to not contain any nucleophilic groups. Those of skill in the are will appreciate other buffers that can be used to modulate the pH of a labeling reaction, with the application of ordinary experimentation, so as to facilitate the labeling of an analyte with a labeling reagent.

Sample Processing:

In certain embodiments of this invention, a sample can be processed prior to, as well as after, labeling of the analytes. The processing can facilitate the labeling of the analytes. The processing can facilitate the analysis of the sample components. The processing can simplify the handling of the samples. The processing can facilitate two or more of the foregoing.

For example, a sample can be treated with an enzyme. The enzyme can be a protease (to degrade proteins and peptides), a nuclease (to degrade nucleic acids) or some other enzyme. The enzyme can be chosen to have a very predictable degradation pattern. Two or more proteases and/or two or more nuclease enzymes may also be used together, or with other enzymes, to thereby degrade sample components.

For example, the proteolytic enzyme trypsin is a serine protease that cleaves peptide bonds between lysine or arginine and an unspecific amino acid to thereby produce peptides that comprise an amine terminus (N-terminus) and lysine or arginine carboxyl terminal amino acid (C-terminus). In this way the peptides from the cleavage of the protein are predictable and their presence and/or quantity, in a sample from a trypsin digest, can be indicative of the presence and/or quantity of the protein of their origin. Moreover, the free amine termini of a peptide can be a good nucleophile that facilitates its labeling. Other exemplary proteolytic enzymes include papain, pepsin, ArgC, LysC, V8 protease, AspN, pronase, chymotrypsin and carboxypeptidease C.

For example, a protein (e.g. protein Z) might produce three peptides (e.g. peptides B, C and D) when digested with a protease such as trypsin. Accordingly, a sample that has been digested with a proteolytic enzyme, such as trypsin, and that when analyzed is confirmed to contain peptides B, C and D, can be said to have originally comprised the protein Z. The quantity of peptides B, C and D will also correlate with the quantity of protein Z in the sample that was digested. In this way, any determination of the identity and/or quantify of one or more of peptides B, C and D in a sample (or a fraction thereof), can be used to identify and/or quantify protein Z in the original sample (or a fraction thereof).

Because activity of the enzymes is predictable, the sequence of peptides that are produced from degradation of a protein of known sequence can be predicted. With this information, "theoretical" peptide information can be generated. A determination of the 'theoretical" peptide fragments in computer assisted analysis of daughter fragment ions (as described above) from mass spectrometry analysis of an actual sample can therefore be used to determine one or more peptides or proteins in one or more unknown samples.

In some cases, sample processing can include treatment of precursors to the analyte or analytes to be labeled. For example, if the analyte or analytes to be labeled are peptides derived from a digested protein and the labeling reagent is, for this example, selected to react with amine groups (e.g. N-α-amine groups and N-ε-amine group of lysine) of the peptide or peptide analytes, the protein (the analyte precursor molecule) of the sample may be processed in a manner that facilitates the labeling reaction. In this example, the protein can be reduced with a reducing agent (e.g. tris[2-carboxyethyl]phosphine (TCEP)) and the thiol groups then blocked by reaction with a blocking reagent (e.g. methyl methanethiosulfonate (MMTS)). In this way the thiol groups of the protein are blocked and therefore do not interfere with the labeling reaction between the amines of the analytes and labeling reagent.

Those of skill in the art will appreciate that treatment of certain other precursor molecules can be performed using readily available reagents and protocols that can be adapted with the aid of routing experimentation. The precise choices or reagents and conditions can be selected depending on the nature of the analyte to be labeled and the labeling reagent.

In some embodiments, sample processing can include the immobilization of the analytes or analyte precursors to a solid support, whether labeled with a labeling reagent or not. In some embodiments, immobilization can facilitate reducing sample complexity. In some embodiments, immobilization can facilitate analyte labeling. In some embodiments, immobilization can facilitate analyte precursor labeling. In some embodiments, immobilization can facilitate selective labeling of a fraction of sample components comprising a certain property (e.g. they comprise or lack cysteine moieties). The immobilization can facilitate two or more of the foregoing.

Separation Including Separation of the Sample Mixture:

In some embodiments, the processing of a sample or sample mixture of labeled analytes can involve separation. One or more separations can be performed on the labeled or unlabeled analytes, labeled or unlabeled analyte precursors, or fractions thereof. One or more separations can be performed on one or more fractions obtained from a solid phase capture. Separations can be preformed on two or more of the foregoing.

For example, a sample mixture comprising differentially labeled analytes from different samples can be prepared. By differentially labeled we mean that each of the labels comprises a unique property that can be identified (e.g. comprises a unique reporter moiety that produces a unique "signature ion" in MS/MS analysis). In order to analyze the sample mixture, components of the sample mixture can be separated and mass analysis performed on only a fraction of the sample mixture. In this way, the complexity of the analysis can be substantially reduced since separated analytes can be individually analyzed for mass thereby increasing the sensitivity of the analysis process. Of course the analysis can be repeated one or more time on one or more additional fractions of the sample mixture to thereby allow for the analysis of all fractions of the sample mixture.

Separation conditions under which identical analytes that are differentially labeled co-elute at a concentration, or in a quantity, that is in proportion to their abundance in the sample mixture can be used to determine the amount of each labeled analyte in each of the samples that comprise the sample mixture provided that the amount of each sample added to the sample mixture is known. Accordingly, in some embodiments, separation of the sample mixture can simplify the analysis whilst maintaining the correlation between signals determined in the mass analysis (e.g. MS/MS analysis) with the amount of the differently labeled analytes in the sample mixture.

The separation can be performed by chromatography. For example, liquid chromatography/mass spectrometry (LC/MS) can be used to effect such a sample separation and mass analysis. Moreover, any chromatographic separation process suitable to separate the analytes of interest can be used. For example, the chromatographic separation can be normal phase chromatography, reversed-phase chromatography, ion-exchange chromatography, size exclusion chromatography or affinity chromatography.

The separation can be performed electrophoretically. Non-limiting examples of electrophoretic separations techniques that can be used include, but are not limited to, 1D electrophoretic separation, 2D electrophoretic separation and/or capillary electrophoretic separation.

An isobaric labeling reagent or a set of reagents can be used to label the analytes of a sample. Isobaric labeling reagents are particularly useful when a separation step is performed because the isobaric labels of a set of labeling reagents are structurally and chemically indistinguishable (and can be indistinguishable by gross mass until fragmentation removes the reporter from the analyte). Thus, all analytes of identical composition that are labeled with different isobaric labels can chromatograph in exactly the same manner (i.e. co-elute). Because they are structurally and chemically indistinguishable, the eluent from the separation process can comprise an amount of each isobarically labeled analyte that is in proportion to the amount of that labeled analyte in the sample mixture. Furthermore, from the knowledge of how the sample mixture was prepared (portions of samples, an other optional components (e.g. calibration standards) added to prepare the sample mixture), it is possible to relate the amount of labeled analyte in the sample mixture back to the amount of that labeled analyte in the sample from which it originated.

The labeling reagents can also be isomeric. Although isomers can sometimes be chromatographically separated, there are circumstances, that are condition dependent, where the separation process can be operated to co-elute all of the identical analytes that are differentially labeled wherein the amount of all of the labeled analytes exist in the eluent in proportion to their concentration and/or quantity in the sample mixture.

As used herein, isobars differ from isomers in that isobars are structurally and chemically indistinguishable compounds (except for isotopic content and/or distribution) of the same nominal gross mass (See for example, FIG. 1) whereas isomers are structurally and/or chemically distinguishable compounds of the same nominal gross mass.

Relative and Absolute Quantitation of Analytes:

In some embodiments, the relative quantitation of differentially labeled identical analytes of a sample mixture is possible. Relative quantitation of differentially labeled identical analytes is possible by comparison of the relative amounts (e.g. area or height of the peak reported) of reporter (e.g. signature ion) that are determined in the second mass analysis for a selected, labeled analyte observed in a first mass analysis. Put differently, where each reporter can be correlated with information for a particular sample used to produce a sample mixture, the relative amount of that reporter, with respect to other reporters observed in the second mass analysis, is the relative amount of that analyte in the sample mixture. Where components combined to form the sample mixture is known, the relative amount of the analyte in each sample used to prepare the sample mixture can be back calculated based upon the relative amounts of reporter observed for the ions of the labeled analyte selected from the first mass analysis. This process can be repeated for all of the different labeled analytes observed in the first mass analysis. In this way, the relative amount (often expressed in concentration and/or quantity) of each reactive analyte, in each of the different samples used to produce the sample mixture, can be determined.

In other embodiments, absolute quantitation of analytes can be determined. For these embodiments, a known amount of one or more differentially labeled analytes (the calibration standard or calibration standards) can be added to the sample mixture. The calibration standard can be an expected analyte that is labeled with an isomeric or isobaric label of the set of labels used to label the analytes of the sample mixture provided that the reporter for the calibration standard is unique as compared with any of the samples used to form the sample mixture. Once the relative amount of reporter for the calibration standard, or standards, is determined with relation to the relative amounts of the reporter for the differentially labeled analytes of the sample mixture, it is possible to calculate the absolute amount (often expressed in concentration and/or quantity) of all of the differentially labeled analytes in the sample mixture. In this way, the absolute amount of each differentially labeled analyte (for which there is a calibration standard in the sample from which the analyte originated) can also be determined based upon the knowledge of how the sample mixture was prepared.

Notwithstanding the foregoing, corrections to the intensity of the reporters (signature ions) can be made, as appropriate, for any naturally occurring, or artificially created, isotopic abundance within the reporters. There are numerous ways to correct for isotopic abundance of impurities in the signature ions of reporters. An example of such a correction can be found in Example 3. A more sophisticated example of these types of corrections can also be found in copending and co-owned U.S. Provisional Patent Application Ser. No. 60/524,844, entitled: "Method and Apparatus For De-Convoluting A Convoluted Spectrum", filed on Nov. 26, 2003, incorporated herein by reference. The more care taken to accurately quantify the intensity of each reporter (e.g. signature ion), the more accurate will be the relative and absolute quantification of the analytes in the original samples.

Proteomic Analysis:

Embodiments of this invention can be used for complex analysis because samples can be multiplexed, analyzed and reanalyzed in a rapid and repetitive manner using mass analysis techniques. For example, sample mixtures can be analyzed for the amount of individual analytes in one or more samples. The amount (often expressed in concentration and/or quantity) of those analytes can be determined for the samples from which the sample mixture was comprised. Because the sample processing and mass analyses can be performed rapidly, these methods can be repeated numerous times so that the amount of many differentially labeled analytes of the sample mixture can be determined with regard to their relative and/or absolute amounts in the sample from which the analyte originated.

One application where such a rapid multiplex analysis is useful is in the area of proteomic analysis. Proteomics can be viewed as an experimental approach to describe the information encoded in genomic sequences in terms of structure, function and regulation of biological processes. This may be achieved by systematic analysis of the total protein component expressed by a cell or tissue. Mass spectrometry, used in combination with the method, mixture, kit and/or composition embodiments of this invention is one possible tool for such global protein analysis.

For example, with a set of four isobaric labeling reagents, it is possible to obtain four time points in an experiment to determine up or down regulation of protein expression, for example, based upon response of growing cells to a particular stimulant. It is also possible to perform fewer time points but to incorporate one or two controls. It is also possible to do duplicates or triplicates in the same multiplex experiment. In all cases, up or down regulation of the protein expression, optionally with respect to the controls, can be determined in a single multiplex experiment. Moreover, because processing of the sample mixture is performed in parallel, the results are directly comparable since there is no risk that slight variations in protocol or experimental conditions may have affected the results. Accordingly, experimental analysis for which these isobaric labeling reagents can be used includes, but is not limited to, time course experiments, biomarker analysis, multiplex proteomic analysis, mudpit experiments, affinity pull-downs, determination of post-translational modifications (PTMs) and multiple control experiments.

II. Methods

According to the methods of this invention, the analyte to be determined is labeled. The labeled analyte, the analyte itself, one or more fragments of the analyte and/or fragments of the label, can be determined by mass analysis. In some embodiments, methods of this invention can be used for the analysis of different analytes in the same sample as well as for the multiplex analysis of the same and/or different analytes in two or more different samples. The two or more samples can be mixed to form a sample mixture. In the multiplex analysis, labeling reagents can be used to determine from which sample of a sample mixture an analyte originated. The absolute and/or relative (with respect to the same analyte in different samples) amount (often expressed in concentration or quantity) of the analyte, in each of two or more of the samples combined to form the sample mixture, can be determined. Moreover, the mass analysis of fragments of the analyte (e.g. daughter fragment ions) can be used to identify the analyte and/or the precursor to the analyte; such as where the precursor molecule to the analyte was degraded.

One distinction of the described approach lies in the fact that analytes from different samples can be differentially isotopically labeled (i.e. isotopically coded) with unique labels that are chemically isomeric or isobaric (have equal mass) and that identify the sample from which the analyte originated. The differentially labeled analytes are not distinguished in MS mode of a mass spectrometer because they all have identical (gross) mass to charge ratios. However, when subjected to dissociative energy levels, such as through collision induced dissociation (CID), the labels can fragment to yield unique reporters that can be resolved by mass (mass to charge ratio) in a mass spectrometer. The relative amount of reporter observed in the mass spectrum can correlate with the relative amount of a labeled analyte in the sample mixture and, by implication, the amount of that analyte in a sample from which it originated. Thus, the relative intensities of the reporters (i.e. signature ions) can be used to measure the relative amount of an analyte or analytes in two or more different samples that were combined to form a sample mixture. From the reporter information, absolute amounts (often expressed as concentration and/or quantity) of an analyte or analytes in two or more samples can be derived if calibration standards for the each analyte, for which absolute quantification is desired, are incorporated into the sample mixture.

For example, the analyte might be a peptide that resulted from the degradation of a protein using an enzymatic digestion reaction to process the sample. Protein degradation can be accomplished by treatment of the sample with a proteolytic enzyme (e.g. trypsin, papain, pepsin, ArgC, LysC, V8 protease, AspN, pronase, chymotrypsin or carboxypeptidase C). By determination of the identity and amount of a peptide in a sample mixture and identifying the sample from which it originated, optionally coupled with the determination of other peptides from that sample, the precursor protein to the degraded peptide can be identified and/or quantified with respect to the sample from which it originated. Because this method allows for the multiplex determination of a protein, or proteins, in more than one sample (i.e. from a sample mixture), it is a multiplex method.

In some embodiments, this invention pertains to a method comprising reacting each of two or more samples, each sample containing one or more reactive analytes, with a different labeling reagent of a set of labeling reagents wherein the different labeling reagents of the set each comprise the formula: RP-X-LK-Y-RG. Consequently, one or more analytes of each sample are labeled with the moiety "RP-X-LK-Y-" by reaction of a nucleophile or electrophile of the analyte with the electrophilic or nucleophilic reactive group (RG), respectively, of the different labeling reagents. The labeling process can produce two or more differentially labeled samples each comprising one or more labeled analytes. The labeling reagents of the set can be isomeric or isobaric. The reporter of each labeling reagent can be identified with, and therefore used to identify, the sample from which each labeled analyte originated.

RG is a reactive group the characteristics of which have been previously described. RP is a reporter moiety the characteristics of which have been previously described. The gross mass of each reporter can be different for each reagent of the set. LK is a linker moiety the characteristics of which have been previously described. The gross mass of the linker can compensate for the difference in gross mass between the reporters for the different labeling reagents such that the aggregate gross mass of the reporter/linker combination is the same for each reagent of the set. X is a bond between an atom of the reporter and an atom of the linker. Y is a bond between an atom of the linker and an atom of the reactive group (or after reaction with an analyte, Y is a bond between the an atom of the linker and an atom of the analyte). Bonds X and Y can fragment in at least a portion of the labeled analytes when subjected to dissociative energy levels in a mass spectrometer. The characteristics of bonds X and Y have been previously described.

Once the analytes of each sample are labeled with the labeling reagent that is unique to that sample, the two or more differentially labeled samples, or a portion thereof, can be mixed to produce a sample mixture. Where quantitation is desired, the volume and/or quantity of each sample combined to produce the sample mixture can be recorded. The volume and/or quantity of each sample, relative to the total sample volume and/or quantity of the sample mixture, can be used to determine the ratio necessary for determining the amount (often expressed in concentration and/or quantity) of an identified analyte in each sample from the analysis of the sample mixture. The sample mixture can therefore comprise a complex mixture wherein relative amounts of the same and/or different analytes can be identified and/or quantitated, either by relative quantitation of the amounts of analyte in each of the two or more samples or absolutely where a calibration standard is also added to the sample mixture.

The mixture can then be subjected to spectrometry techniques wherein a first mass analysis can be performed on the sample mixture, or fraction thereof, using a first mass analyzer. Ions of a particular mass to charge ratio from the first mass analysis can then be selected. The selected ions can then be subjected to dissociative energy levels (e.g. collision-induced dissociation (CID)) to thereby induce fragmentation of the selected ions. By subjecting the selected ions, of a particular mass to charge ratio, of the labeled analytes to dissociative energy levels, both bonds X and Y can be fragmented in at least a portion of the selected ions. Fragmentation of both bonds X and Y can cause fragmentation of the reporter/linker moiety as well as cause release the charged or ionized reporter from the analyte. Ions subjected to dissociative energy levels can also cause fragmentation of the analyte to thereby produce daughter fragment ions of the analyte. The ions (remaining selected ions, daughter fragment ions and charged or ionized reporters), or a fraction thereof, can then be directed to a second mass analyzer.

In the second mass analyzer, a second mass analysis can be performed on the selected ions, and the fragments thereof. The second mass analysis can determine the gross mass (or m/z) and relative amount of each unique reporter that is present at the selected mass to charge ratio as well as the gross mass of the daughter fragment ions of at least one reactive analyte of the sample mixture. For each analyte present at the selected mass to charge ratio, the daughter fragment ions can be used to identify the analyte or analytes present at the selected mass to charge ratio. For example, this analysis can be done as previously described in the section entitled: "Analyte Determination By Computer Assisted Database Analysis".

In some embodiments, certain steps of the process can be repeated one or more times. For example, in some embodiments, ions of a selected mass to charge ratio from the first mass spectrometric analysis, different from any previously selected mass to charge ratio, can be treated to dissociative energy levels to thereby form ionized reporter moieties and ionized daughter fragment ions of at least some of the selected ions, as previously described. A second mass analysis of the selected ions, the ionized reporter moieties and the daughter fragment ions, or a fraction thereof, can be performed. The gross mass and relative amount of each reporter moiety in the second mass analysis and the gross mass of the daughter fragment ions can also be determined. In this way, the information can be made available for identifying and quantifying one or more additional analytes from the first mass analysis.

In some embodiments, the whole process can be repeated one or more times. For example, it may be useful to repeat the process one or more times where the sample mixture has been fractionated (e.g. separated by chromatography or electrophoresis). By repeating the process on each fraction, it is possible to analyze all the entire sample mixture. It is contemplated that in some embodiments, the whole process will be repeated one or more times and within each of these repeats, certain steps will also be repeated one or more times such as described above. In this way, the contents of sample mixture can be interrogated and determined to the fullest possible extent.

Those of ordinary skill in the art of mass spectrometry will appreciate that the first and second mass analysis can be performed in a tandem mass spectrometer. Instruments suitable for performing tandem mass analysis have been previously described herein. Although tandem mass spectrometers are preferred, single-stage mass spectrometers may be used. For example, analyte fragmentation may be induced by cone-voltage fragmentation, followed by mass analysis of the resulting fragments using a single-stage quadrupole or time-of-flight mass spectrometer. In other examples, analytes may be subjected to dissociative energy levels using a laser source and the resulting fragments recorded following post-source decay in time-of-flight or tandem time-of-flight (TOF-TOF) mass spectrometers.

According to the preceding disclosed multiplex methods, in some embodiments, bond X can be more or less prone to, or substantially equal to, fragmentation as compared with fragmentation of bonds of the analyte (e.g. an amide (peptide) bond in a peptide backbone). In some embodiments, bond Y can be more or less prone to fragmentation as compared with fragmentation of bonds of the analyte (e.g. an amide (peptide) bond in a peptide backbone). In some embodiments, the linker for each reagent of the set is neutral in charge after the fragmentation of bonds X and Y (i.e. the linker fragments to produce a neutral loss of mass and is therefore not observed in the MS/MS spectrum). In still some other embodiments, the position of bonds X and Y does not vary within the labeling reagents of a set, within the labeled analytes of a mixture or within the labeling reagents of a kit. In yet some other embodiments, the reporter for each reagent of the set does not substantially sub-fragment under conditions that are used to fragment the analyte (e.g. an amide (peptide) bond of a peptide backbone). In yet some other embodiments, bond X is less prone to fragmentation as compared with bond Y. In still some other embodiments, bond Y is less prone to fragmentation as compared with bond X. In still some other embodiments, bonds X and Y are of approximately the same lability or otherwise are selected such that fragmentation of one of bonds X or Y results in the fragmentation of the other of bonds X or Y. Other characteristics of the groups that for the RP-X-LK-Y- moiety of labeled analytes have previously been described.

In some embodiments, the label of each isobarically labeled analyte can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label can comprise one or more heavy atom isotopes. The heterocyclic ring can be substituted or unsubstituted. The heterocyclic ring can be aliphatic or aromatic. Possible substituents of the heterocyclic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

In some embodiments, labeled analytes in the sample mixture can be isobars and each comprise the general formula:

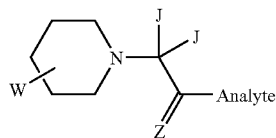

wherein: Z is O, S, NH or $NR^1$; each J is the same or different and is H, deuterium (D), $R^1$, $OR^1$, $SR^1$, $NHR^1$, $N(R^1)_2$, fluorine, chlorine, bromine or iodine; W is an atom or group that is located ortho, meta or para to the ring nitrogen and is NH, $N—R^1$, $N—R^2$, $P—R^1$, $P—R^2$, O or S; each carbon of the heterocyclic ring has the formula $CJ_2$; each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and $R^2$ is an amino alkyl, hydroxy alkyl, thio alkyl group or a cleavable linker that cleavably links the reagent to a solid support wherein the amino alkyl, hydroxy alkyl or thio alkyl group comprises one to eight carbon atoms, which may optionally contain a heteroatom or a substituted or unsubstituted aryl group, and wherein the carbon atoms of the alkyl and aryl groups independently comprise linked hydrogen, deuterium and/or fluorine atoms.

For example, the sample mixture can comprise one or more isobarically labeled analytes of the general formula:

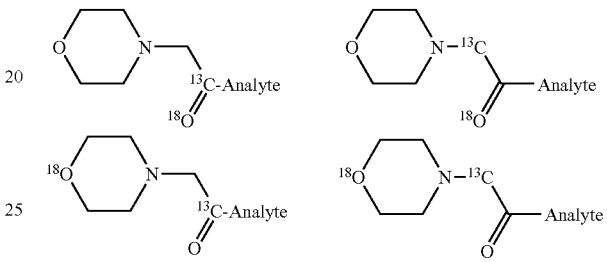

wherein isotopes of carbon 13 and oxygen 18 are used to balance the gross mass between the morpholine reporter and the carbonyl linker of the different labeling reagents.

Morpholine labeling reagents suitable to produce labeled analytes of this general structure can be prepared by numerous synthetic routes. For example, isotopically labeled or non-isotopically morpholine compounds can be reacted with isotopically labeled or non-isotopically labeled bromoacetic acid compounds as described in Example 1. It should likewise be apparent that a ring-substituted morpholine and/or substituted bromoacetic acid starting materials can also be selected and used by one of skill in the art without the exercise of undue experimentation (with little or no change to the above described procedure or other procedures well-known in the art) to thereby produce various different morpholine based labeling reagents, of differing heavy atom isotope content (i.e. isotopically coded), that can be used in the sets or kits of this invention.

Instead of morpholine, it is possible to choose a substituted or unsubstituted piperidine of desired isotopic distribution. When piperidine is chosen, the isotopes D (deuterium) $^{13}C$ or $^{15}N$ can be substituted for H, $^{12}C$ and $^{14}N$, respectively, and used to alter the gross mass of the reagents of a set of labeling reagents in a manner similar to that illustrated for morpholine except that in the case of piperidine, $^{18}O$ is not used in the ring atoms. An exemplary synthesis of a piperidine, optionally using isotopically enriched starting materials, is described in Example 6.

The sample mixture can comprise one or more isobarically labeled analytes of the formula:

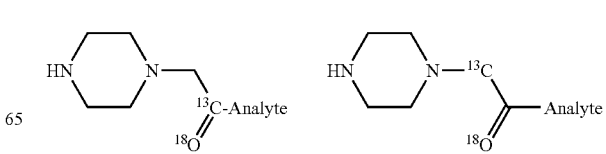

Figure 9A:
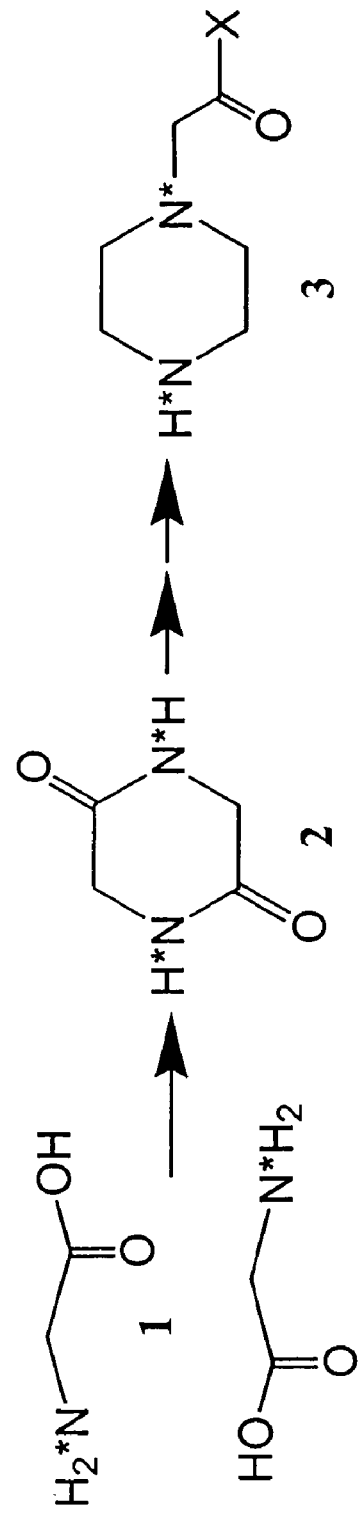
FIGS. 9A and 9B are an illustration of synthetic routes to isotopically labeled piperazine labeling reagents from basic starting materials. The route can also be used to prepare non-isotopically labeled piperazine reagents wherein non-isotopically labeled starting materials are used.
Figure 9B:
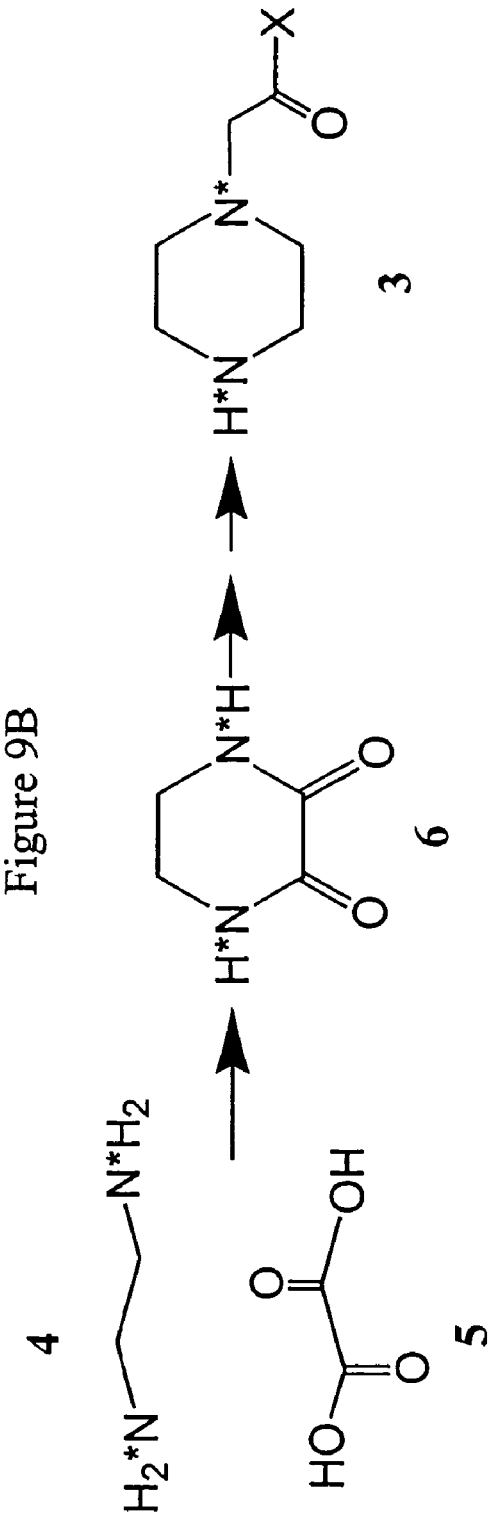

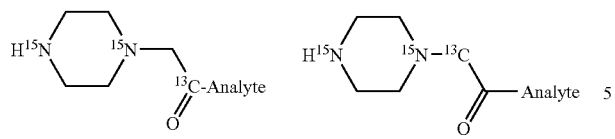

wherein isotopes of carbon 13, oxygen 18 and nitrogen 15 are used to balance the gross mass between the reporter and the carbonyl linker of the different labeling reagents. Piperazine labeling reagents suitable to produce labeled analytes of this general structure can be prepared by numerous synthetic routes. For example, heavy or light piperazine compounds can be reacted with heavy or light labeled bromoacetic acid compounds as described in Example 7. With reference to FIGS. 9A and 9B, a general schematic is shown for two different synthetic routes to isotopically enriched piperazines using readily available heavy or light starting materials.

Specifically with reference to FIG. 9A, two equivalents of $^{15}$N-labeled glycine 1 can be condensed to form the bis-isotopically labeled di-ketopiperazine 2 (the isotopic label is represented by the * in the Figure). The di-ketopiperazine can then be reduced to an isotopically labeled piperazine. The isotopically labeled piperazine can then be reacted with bromoacetic acid and converted to an active ester 3 as described in Example 7.

Specifically with reference to FIG. 9B, ethylenediamine 4 can be condensed with oxalic acid 5 to for the bis-isotopically labeled di-ketopiperazine 6 (the isotopic label is represented by the * in the Figure). The di-ketopiperazine can then be reduced to an isotopically labeled piperazine. The isotopically labeled piperazine can then be reacted with bromoacetic acid and converted to an active ester 3 as described in Example 7.

It should likewise be apparent that a ring-substituted piperazine can be made using the above-described methods by merely choosing appropriately substituted starting materials. Where appropriate, a substituted bromoacetic acid (either heavy or light) can likewise be used. By heavy we mean that the compound is isotopically enriched with one or more heave atom isotopes). By light we mean that it is not isotopically enriched. Accordingly, appropriately substituted starting materials can be selected to thereby produce various different piperazine based labeling reagents that can be used in the sets of this invention.

For example, the sample mixture can comprise one or more isobarically labeled analytes of the formula:

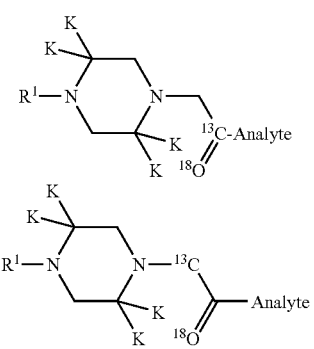

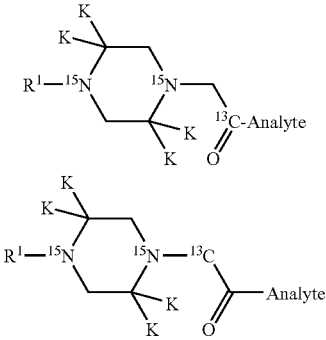

wherein: isotopes of carbon 13, oxygen 18 and nitrogen 15 are used to balance the gross mass between the reporter and the carbonyl linker of the different labeling reagents and wherein; 1) each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and 2) each K is independently selected as hydrogen or an amino acid side chain. Substituted piperazine labeling reagents suitable to produce labeled analytes of this general structure can be prepared by numerous synthetic routes.

Figure 10:
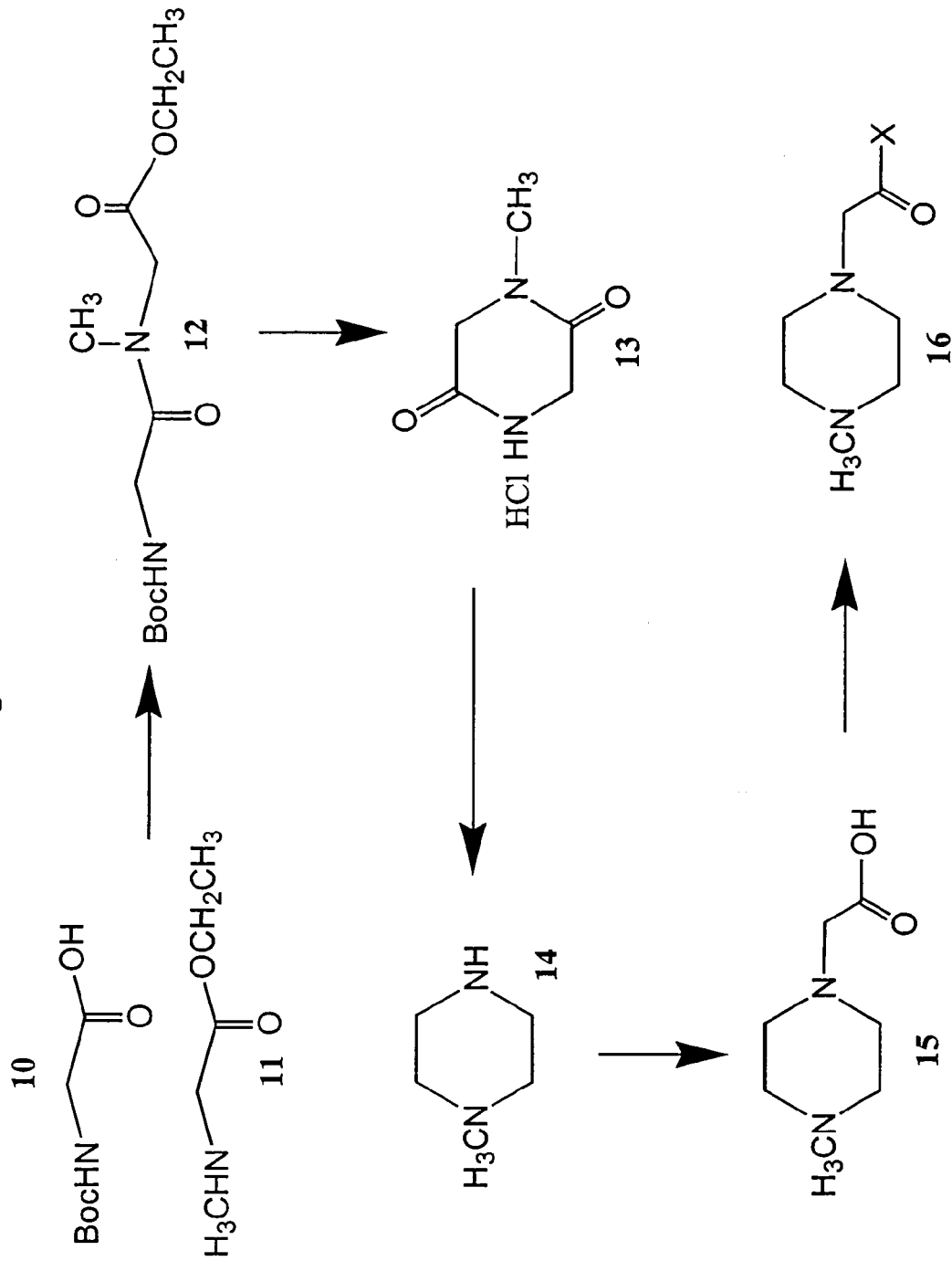
FIG. 10 is an illustration of a synthetic route to isotopically labeled and non-isotopically labeled N-alkyl piperazine labeling reagents from basic starting material's.

For example, with reference to FIG. 10, N-alkyl substituted piperazine reagents can be prepared in accordance with the illustrated procedure. The tert-butyloxycarbonyl (t-boc) protected glycine 10 can be condensed with the ester (e.g. ethyl ester) of N-methyl-glycine 11 to thereby form the ester of the t-boc protected glycine-N-methyl-glycine dimer 12. The gly-gly dimer 12 can then be cyclized by removal of the t-boc protecting group followed by condensation to thereby form the acid salt of the N-methyl-di-ketopiperazine 13. The acid salt of 13 can be neutralized and reduced to form the N-methyl-piperazine 14. The N-methyl-piperazine 14, can then be reacted with bromoacetic acid 15 (or substituted versions thereof) and converted to an active ester 16 as described in Example 7.

It should be apparent that a ring-substituted piperazine can be made using the above-described method by merely choosing an amino acid or N-methyl amino acid (or ester thereof) other than glycine (e.g. alanine, phenylalanine, leucine, isoleucine, valine, asparagine, aspartic acid, etc). It should likewise be apparent that the amino acids can be isotopically labeled in a manner suitable for preparing ring substituted piperazines having the desired distribution of isotopes necessary to prepare sets of isobaric labeling reagents.

Figure 11:
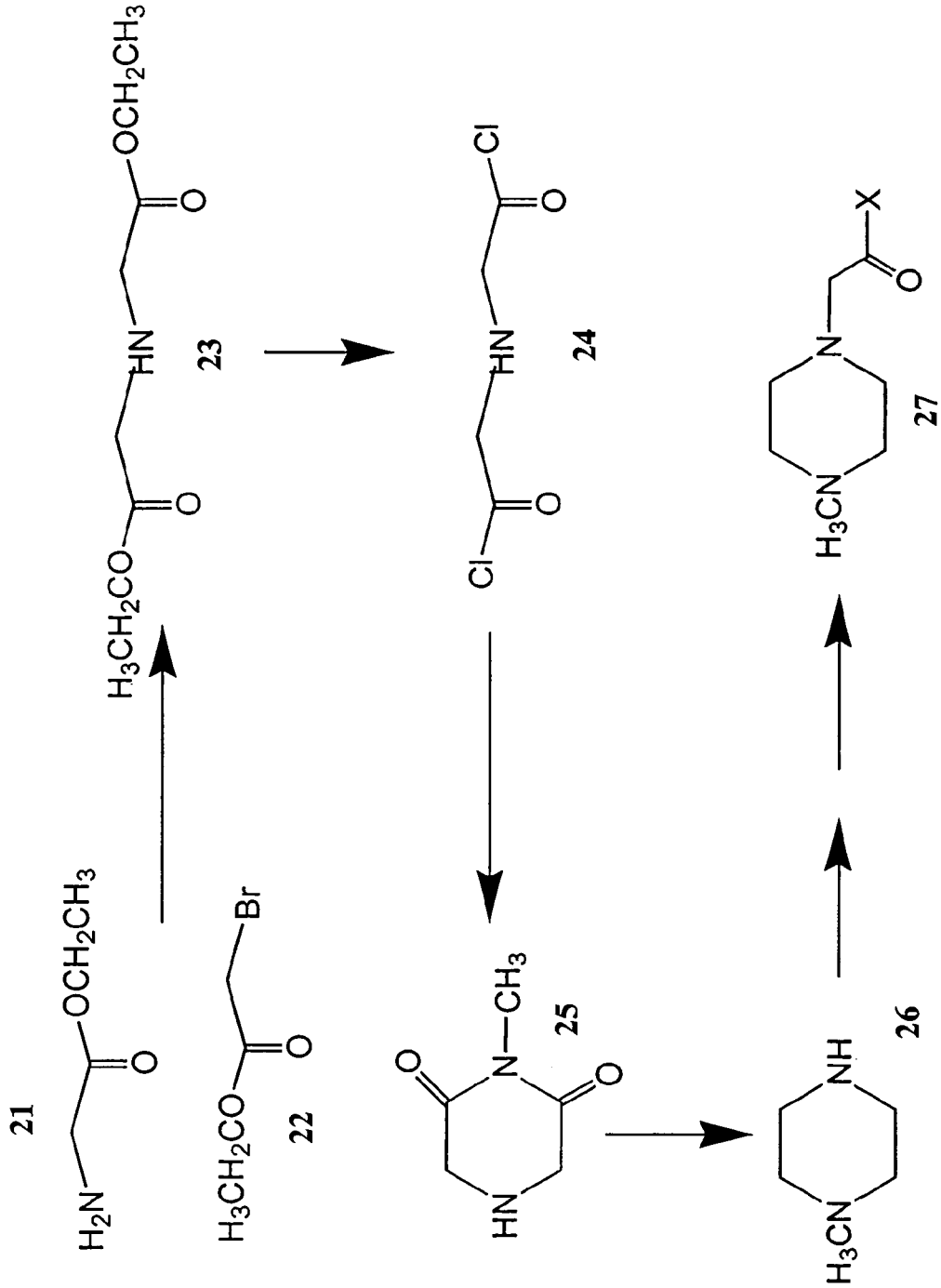
FIG. 11 is an illustration of a synthetic route to isotopically labeled and non-isotopically labeled N-alkyl piperazine labeling reagents from basic starting materials.
Figure 12:
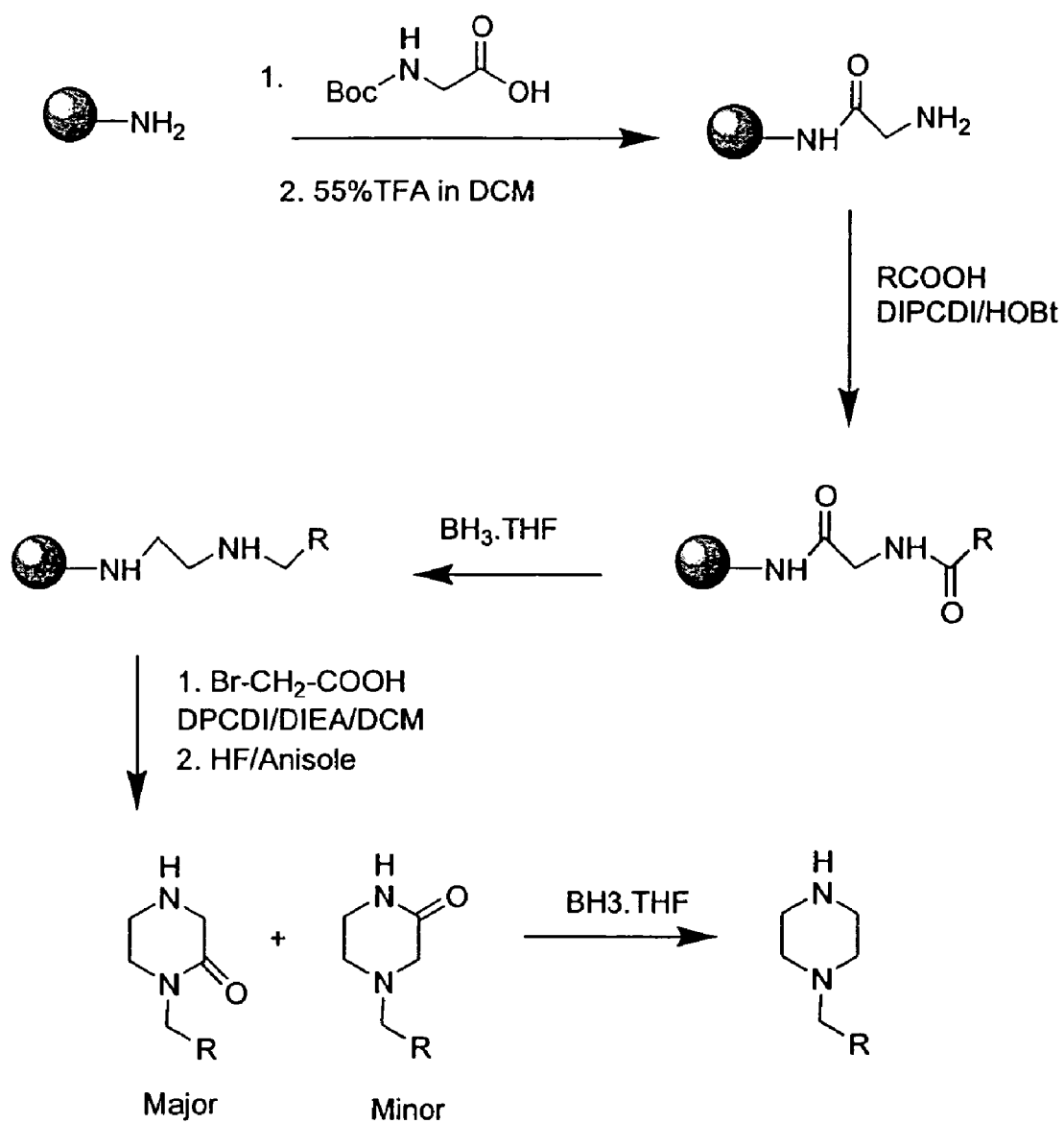
FIG. 12 is an illustration of a solid phase based synthetic route to isotopically labeled and non-isotopically labeled piperazine labeling reagents from basic starting materials.

N-alkyl substituted piperazine reagents can be prepared in accordance by still another illustrated procedure. With reference to FIG. 11, glycine methyl ester 21 can be reacted with the ethyl ester of bromoacetic acid 22 to form the diethyl iminodiacetate 23. The diester of the diethyl iminodiacetate 23 can be converted to a di-acid chloride 24 by treatment with an appropriate reagent (e.g. thionyl chloride). The di-acid chloride 24 can then be reacted with, for example, an alkyl amine (e.g. methyl amine) to form an N-alkyl-di-ketopiperazine 25. The N-alkyl-di-ketopiperazine 25 can then be reduced to form the N-alkyl-piperazine 26. The N-alkyl-piperazine can then be reacted with bromoacetic acid and converted to an active ester 27 as described in Example 7.

It should be apparent that a ring-substituted piperazine can be made using the above-described method by merely choosing an ester of an amino acid other than glycine (e.g. alanine, phenylalanine, leucine, isoleucine, valine, asparagine, aspartic acid, etc) or a substituted version of bromoacetic acid. It should likewise be apparent that the amino acids and bromoacetic acid (and its substituted derivatives) can be isotopically labeled in a manner suitable for preparing ring substituted piperazines having the desired distribution of isotopes necessary to prepare sets of isobaric labeling reagents. It should be further apparent that choosing an alkyl diamine, hydroxyalkyl amine or thioalkylamine, or isotopically labeled version thereof, instead of an alkyl amine can be used to produce the support bound labeling reagents as described in more detail below.

In yet some other embodiments of the method, labeled analytes in the sample mixture are isobars and each comprise the formula:

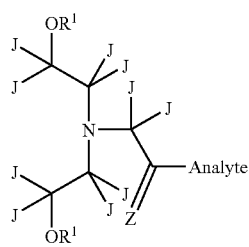

wherein: Z is O, S, NH or $NR^1$; each J is the same or different and is selected from the group consisting of: H, deuterium (D), $R^1$, $OR^1$, $SR^1$, $NHR^1$, $N(R^1)_2$, fluorine, chlorine, bromine and iodine; each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms.

For example, the sample mixture can comprise two or more isobarically labeled analytes of the formula:

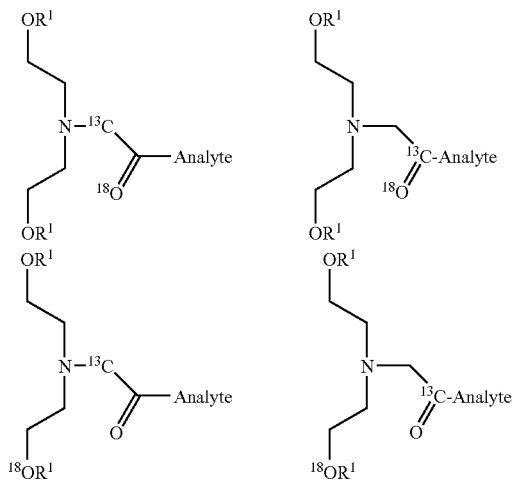

wherein isotopes of carbon 13 and oxygen 18 are used to balance the gross mass between the reporter and the carbonyl linker of the different labeling reagents. Substituted labeling reagents suitable to produce labeled analytes of this general structure can be prepared by the general process described in Example 8.

In still some other embodiments of this invention, each different labeling reagent of a set or kit of labeling reagents can be linked to a support through a cleavable linker such that each different sample can be reacted with a support carrying a different labeling reagent. In some embodiments, the supports can themselves be used for the labeling of reactive analytes. In some embodiments, the labeling reagents can be removed from the supports and then used, in some cases after subsequent processing (e.g. protection of reactive groups), for the labeling of reactive analytes.

According to some embodiments, the analytes from a sample can be reacted with the solid support (each sample being reacted with a different solid support and therefore a different reporter) and the resin bound components of the sample that do not react with the reactive group can be optionally washed away. The labeled analyte or analytes can then be removed from each solid support by treating the support under conditions that cleave the cleavable linker and thereby release the reporter/linker/analyte complex from the support. Each support can be similarly treated under conditions that cleave the cleavable linker to thereby obtain two or more different samples, each sample comprising one or more labeled analytes wherein the labeled analytes associated with a particular sample can be identified and/or quantified by the unique reporter linked thereto. The collected samples can then be mixed to form a sample mixture, as previously described.

For example, each different labeling reagent of the set used in the previously described method can be a solid support of the formula: E-F-RP-X-LK-Y-RG, wherein; RG, X, Y, RP and LK have been described previously. E is a solid support and F is a cleavable linker linked to the solid support and cleavably linked to the reporter. Supports of this general formula can be prepared as described in Example 9.

In some embodiments, a set of support bound labeling reagents can be based on labeled N-(aminoalkyl), N-(thioalkyl) or N-(hydroxyalkyl)-piperazine derivatives. Both heavy and light piperazine derivatives can be prepared. The labeled N-(aminoalkyl), N-(thioalkyl) or N-(hydroxyalkyl)-piperazine derivatives can be formed, for example, by using the procedure illustrated in FIG. 11 starting with an alkyl diamine, thioalkyl amine or hydroxyalkyl amine as the N-alkyl amine (see the discussion of FIG. 11, above). The alkyl diamine, thioalkyl amine or hydroxyalkyl amine can be heavy or light where appropriate for synthesis of a desired N-(aminoalkyl), N-(thioalkyl) or N-(hydroxyalkyl)-piperazine derivative. The amino, hydroxyl or thiol group of the N-(aminoalkyl), N-(thioalkyl) or N-(hydroxyalkyl)-piperazine derivatives can be protected as appropriate. When an alkyl diamine, thioalkylamine or hydroxyalkyl amine is used, the piperazine can comprise an N-aminoalkyl, N-thioalkyl or N-hydroxyalkyl moiety wherein the amino, hydroxyl or thiol group of the moiety can be reacted with the cleavable linker on a support to thereby cleavably link the piperazine, prepared from the N-(aminoalkyl), N-(thioalkyl) or N-(hydroxyalkyl)-piperazine derivative, to the support.

The support comprising a labeling reagent can be prepared by any of several methods. In some embodiments, the amino, hydroxyl or thiol group of the N-(aminoalkyl), N-(thioalkyl) or N-(hydroxyalkyl)-piperazine can be reacted with the cleavable linker of a suitable support. The cleavable linker can be a "sterically hindered cleavable linker" (See: Example 9). The piperazine can be reacted with isotopically labeled or non-isotopically labeled haloacetic acid (substituted or unsubstituted) depending on the nature of the labeling reagent desired for the set of labeling reagents. Thereafter the carboxylic acid can be converted to an active ester. The active ester can be reacted with analytes of a sample to thereby label the analytes with the labeling reagent of the support. Cleavage of the cleavable linker will release the labeled analyte from the support. This process can be repeated with an unique piperazine based labeling reagent for the preparation of the different supports of a set of labeling supports.

In some embodiments, the N-(aminoalkyl), N-(thioalkyl) or N-(hydroxyalkyl)-piperazine can be first reacted with isotopically labeled or non-isotopically labeled haloacetic acid (substituted or unsubstituted), or an ester thereof. Preferably, the amino, hydroxyl or thiol group of the N-(aminoalkyl), N-(thioalkyl) or N-(hydroxyalkyl)-piperazine can be protected with a suitable protecting reagent (For a list of suitable protecting groups See: Green et al., Protecting Groups In Organic Synthesis, Third Edition, John Wiley & Sons, Inc. New York, 1999). The unprotected amino, thiol or hydroxyl group of the resulting bis-alkylated piperazine can then be reacted with the cleavable linker of a suitable support. Thereafter the carboxylic acid can be converted to an active ester. If the haloacetic acid compound was an ester, the ester can be saponified prior to conversion to an active ester. The active ester can be reacted with analytes of a sample to thereby label the analytes with the labeling reagent of the support. Cleavage of the cleavable linker will release the labeled analyte from the support. This process can be repeated with a unique piperazine based labeling reagent for the preparation of the different supports of a set of labeling supports.

Therefore, in some embodiments, the set of labeling reagents can comprise one or more of the following support bound labeling reagents:

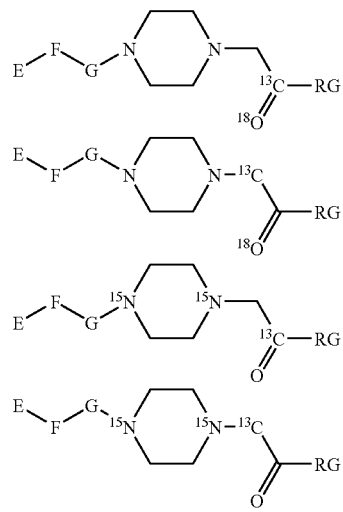

wherein RG, E and F have been previously described. According to the method, G can be an amino alkyl, hydroxy alkyl or thio alkyl group, cleavably linked to the cleavable linker wherein the amino alkyl, hydroxy alkyl or thio alkyl group comprises one to eight carbon atoms, which may optionally contain a heteroatom or a substituted or unsubstituted aryl group, and wherein the carbon atoms of the alkyl and aryl groups independently comprise linked hydrogen, deuterium and/or fluorine atoms. Each carbon of the heterocyclic ring can have the formula $CJ_2$, wherein each J is the same or different and is selected from the group consisting of H, deuterium (D), $R^1$, $OR^1$, $SR^1$, $NHR^1$, $N(R^1)_2$, fluorine, chlorine, bromine and iodine. Each $R^1$ can be the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms.

In some embodiments, the labeled analytes can be generated by first reacting the analyte with a support comprising the labeling reagent, cleavably linked to the support through a cleavable linker, and then cleaving the labeled analyte from the support. Accordingly, a sample mixture can comprise one or more isobarically labeled analytes of the formula:

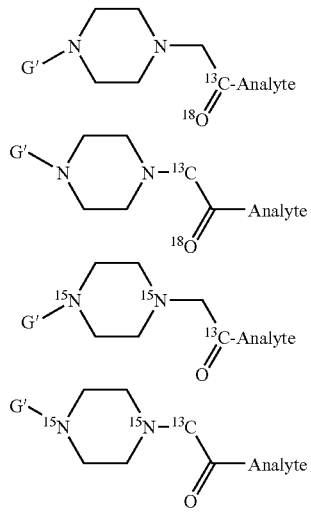

wherein: G' can be an amino alkyl, hydroxy alkyl or thio alkyl group comprising one to eight carbon atoms which may optionally contain a heteroatom or a substituted or unsubstituted aryl group wherein the carbon atoms of the alkyl and aryl groups independently comprise linked hydrogen and/or deuterium atoms. Each carbon of the heterocyclic ring can have the formula $CJ_2$, wherein each J is the same or different and is selected from the group consisting of: H, deuterium (D), $R^1$, $OR^1$, $SR^1$, $NHR^1$, $N(R^1)_2$, fluorine, chlorine, bromine and iodine. Each $R^1$ can be the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms. Here the alkyl amine group, hydroxy alkyl group or thio alkyl group can be the moiety that was linked to the cleavable linker of the solid support. The product of each cleavage reaction can be combined to produce a sample mixture suitable for analysis of labeled analytes by the methods described herein.

In some embodiments, methods of the invention can further comprise digesting each sample with at least one enzyme to partially, or fully, degrade components of the sample prior to performing the labeling of the analytes of the sample (Also see the above section entitled: "Sample Processing"). For example, the enzyme can be a protease (to degrade proteins and peptides) or a nuclease (to degrade nucleic acids). The enzymes may also be used together to thereby degrade sample components. The enzyme can be a proteolytic enzyme such as trypsin, papain, pepsin, ArgC, LysC, V8 protease, AspN, pronase, chymotrypsin or carboxypeptidease C.

In some embodiments, methods can further comprise separating the sample mixture prior to performing the first mass analysis (Also see the above section entitled: "Separation Of The Sample Mixture"). In this manner the first mass analysis can be performed on only a fraction of the sample mixture. The separation can be performed by any separations method, including by chromatography or by electrophoresis. For example, liquid chromatography/mass spectrometry (LC/MS) can be used to effect such a sample separation and mass analysis. Moreover, any chromatographic separation process suitable to separate the analytes of interest can be used. Non-limiting examples of suitable chromatographic and electrophoretic separations processes have been described herein.

In still other embodiments, the methods of the invention can comprise both an enzyme treatment to degrade sample components and a separations step.

As described previously, it is possible to determine the analyte associated with the selected ions by analysis of the gross mass of the daughter fragment ions. One such method of determination is described in the section entitled: "Analyte Determination By Computer Assisted Database Analysis".

Once the analyte has been determined, information regarding the gross mass and relative amount of each reporter moiety in the second mass analysis and the gross mass of daughter fragment ions provides the basis to determine other information about the sample mixture. The amount of reporter can be determined by peak intensity in the mass spectrum. In some embodiments, the amount of reporter can be determined by analysis of the peak height or peak width of the reporter (signature ion) signal obtained using the mass spectrometer. Because each sample can be labeled with a different labeling reagent and each labeling reagent can comprise a unique reporter that can be correlated with a particular sample, determination of the different reporters in the second mass analysis identifies the sample from which the ions of the selected analyte originated. Where multiple reporters are found (e.g. according to the multiplex methods of the invention), the relative amount of each reporter can be determined with respect to the other reporters. Because the relative amount of each reporter determined in the second mass analysis correlates with the relative amount of an analyte in the sample mixture, the relative amount (often expressed as concentration and/or quantity) of the analyte in each sample combined to form the sample mixture can be determined. As appropriate, a correction of peak intensity associated with the reporters can be performed for naturally occurring, or artificially created, isotopic abundance, as previously discussed. More specifically, where the volume and/or quantity of each sample that is combined to the sample mixture is known, the relative amount (often expressed as concentration and/or quantity) of the analyte in each sample can be calculated based upon the relative amount of each reporter determined in the second mass analysis.

This analysis can be repeated one or more times on selected ions of a different mass to charge ratio to thereby obtain the relative amount of one or more additional analytes in each sample combined to form the sample mixture. As appropriate, a correction of peak intensity associated with the reporters can be performed for naturally occurring, or artificially created, isotopic abundance.

Alternatively, where a calibration standard comprising a unique reporter linked to an analyte, having the selected mass to charge ratio, has been added to the sample mixture in a known amount (often expressed as a concentration and/or quantity), the amount of the unique reporter associated with the calibration standard can be used to determine the absolute amount (often expressed as a concentration and/or quantity) of the analyte in each of the samples combined to form the sample mixture. This is possible because the amount of analyte associated with the reporter for the calibration standard is known and the relative amounts of all other reporters can be determined for the labeled analyte associated with the selected ions. Since the relative amount of reporter, determined for each of the unique reporters (including the reporter for the calibration standard), is proportional to the amount of the analyte associated with each sample combined to form the sample mixture, the absolute amount (often expressed as a concentration and/or quantity) of the analyte in each of the samples can be determined based upon a ratio calculated with respect to the formulation used to produce the sample mixture. As appropriate, a correction of peak intensity associated with the reporters can be performed for naturally occurring, or artificially created, isotopic abundance.

This analysis can be repeated one or more times on selected ions of a different mass to charge ratio to thereby obtain the absolute amount of one or more additional analytes in each sample combined to form the sample mixture. As appropriate, a correction of peak intensity associated with the reporters can be performed for naturally occurring, or artificially created, isotopic abundance.

In some embodiments, the methods can be practiced with digestion and/or separation steps. In some embodiments, the steps of the methods, with or without the digestion and/or separation steps, can be repeated one or more times to thereby identify and/or quantify one or more other analytes in a sample or one or more analytes in each of the two or more samples (including samples labeled with support bound labeling reagents). Depending of whether or not a calibration standard is present in the sample mixture for a particular analyte, the quantitation can be relative to the other labeled analytes, or it can be absolute. Such an analysis method can be particularly useful for proteomic analysis of multiplex samples of a complex nature, especially where a preliminary separation of the labeled analytes (e.g. liquid chromatography or electrophoretic separation) precedes the first mass analysis.

In some embodiments, the analytes can be peptides in a sample or sample mixture. Analysis of the peptides in a sample, or sample mixture, can be used to determine the amount (often expressed as a concentration and/or quantity) of identifiable proteins in the sample or sample mixture wherein proteins in one or more samples can be degraded prior to the first mass analysis. Moreover, the information from different samples can be compared for the purpose of making determinations, such as for the comparison of the effect on the amount of the protein in cells that are incubated with differing concentrations of a substance that may affect cell growth. Other, non-limiting examples may include comparison of the expressed protein components of diseased and healthy tissue or cell cultures. This may encompass comparison of expressed protein levels in cells, tissues or biological fluids following infection with an infective agent such as a bacteria or virus or other disease states such as cancer. In other examples, changes in protein concentration over time (time-course) studies may be undertaken to examine the effect of drug treatment on the expressed protein component of cells or tissues. In still other examples, the information from different samples taken over time may be used to detect and monitor the concentration of specific proteins in tissues, organs or biological fluids as a result of disease (e.g. cancer) or infection.

In some embodiments, the analyte can be a nucleic acid fragment in a sample or sample mixture. The information on the nucleic acid fragments can be used to determine the amount (often expressed as a concentration and/or quantity) of identifiable nucleic acid molecules in the sample or sample mixture wherein the sample was degraded prior to the first mass analysis. Moreover, the information from the different samples can be compared for the purpose of making determinations as described above.

III. Workflows

In some embodiments, the labeling of the analytes of a sample can be performed prior to performing sample processing steps. In some embodiments, the labeling of analytes can be performed amongst other sample processing steps. In some embodiments, the labeling of analytes is the last step of sample processing and/or immediately precedes the preparation of a sample mixture.

Using proteomic analysis as a non-limiting example, there are at least several possible workflows that might be used. To aid in understanding of the following discussion a distinction is sometimes made between the precursor protein and the analyte peptide. However, it should be understood that either, or both, of the protein and the peptide can be considered analytes as described herein.

In one type of workflow, the precursor proteins can be digested to peptide analytes that can thereafter be labeled. In another type of workflow, the precursor proteins can be labeled with the labeling reagent and then digested to labeled peptide analytes. In another type of workflow, the precursor proteins can be captured on a solid support, digested and then the support bound peptides can be labeled. Optionally the flow through peptides can also labeled. In another type of workflow, the precursor proteins can be captured on a solid support, labeled and then the support bound protein can be digested to produce labeled peptides. Optionally the flow through peptides can also analyzed. Regardless of the workflow, additional sample processing (e.g. separation steps) can be performed on the labeled peptides as desired before MS analysis.

A) Exemplary Workflows Involving Digestion Followed by Labeling

Figure 20:
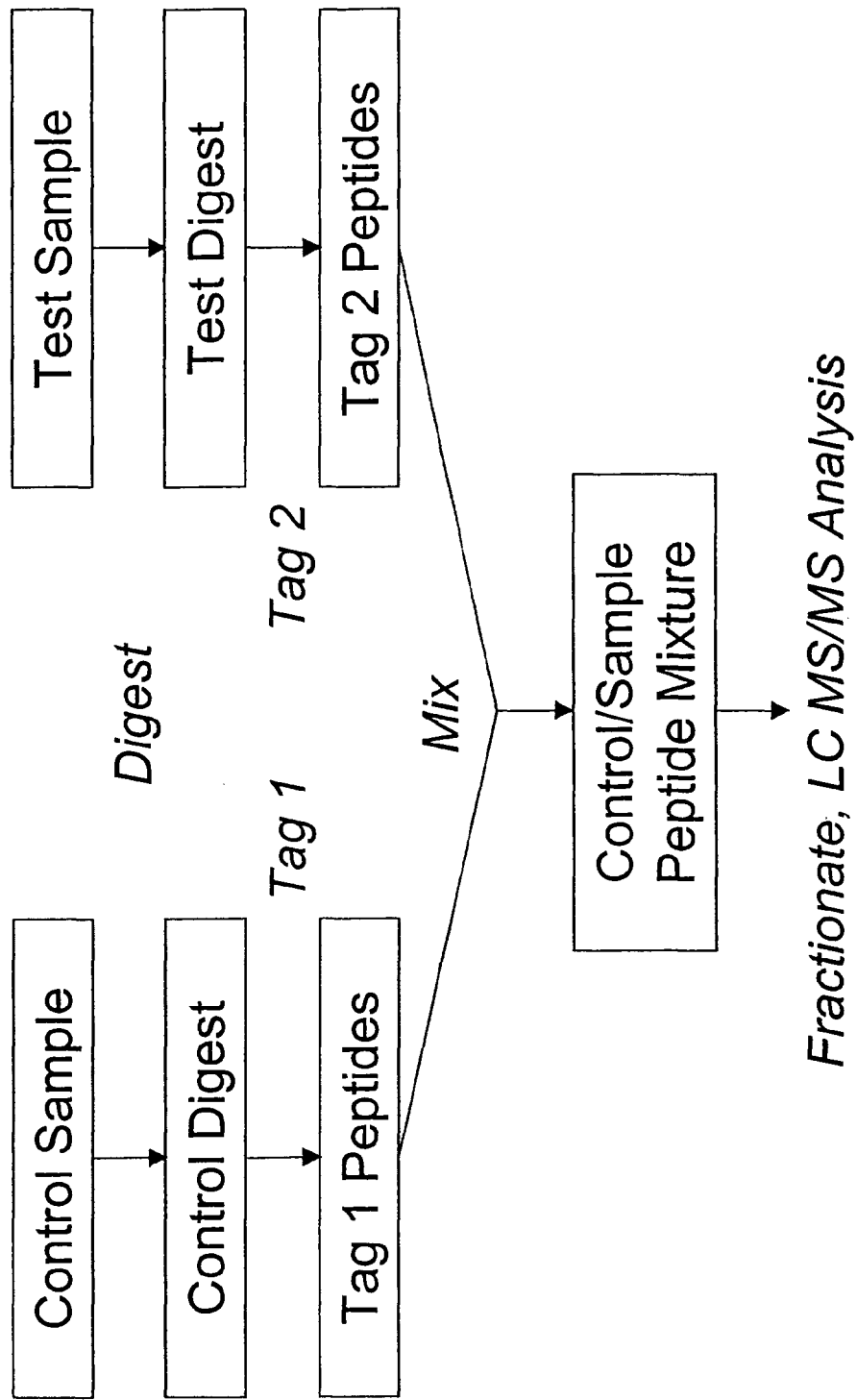
FIG. 20 is an illustration of a one possible workflow for proteomic analysis.

With reference to FIG. 20 for example, there might be a "control" sample and a "test" sample to be analyzed. If, for the example illustrated in FIG. 20, the goal is to analyze peptides (as the analytes) of "control" and "test" sample proteins, the proteins of the samples can, in some embodiments, be optionally reduced, optionally cysteine blocked and digested with an enzyme to thereby produce the analyte peptides that can be labeled for subsequent analysis. The analyte peptides can, in some embodiments, be labeled without further sample processing. In some embodiments, further sample processing might be desired before labeling and/or after labeling. For example, a separation step might be performed to eliminate certain types of peptides that are not of interest, thereby decreasing the complexity of the sample. In some embodiments, the labeled analyte peptide can be subject to separation (e.g. high performance liquid chromatography (HPLC) before mass spectral analysis.

Figure 21A:
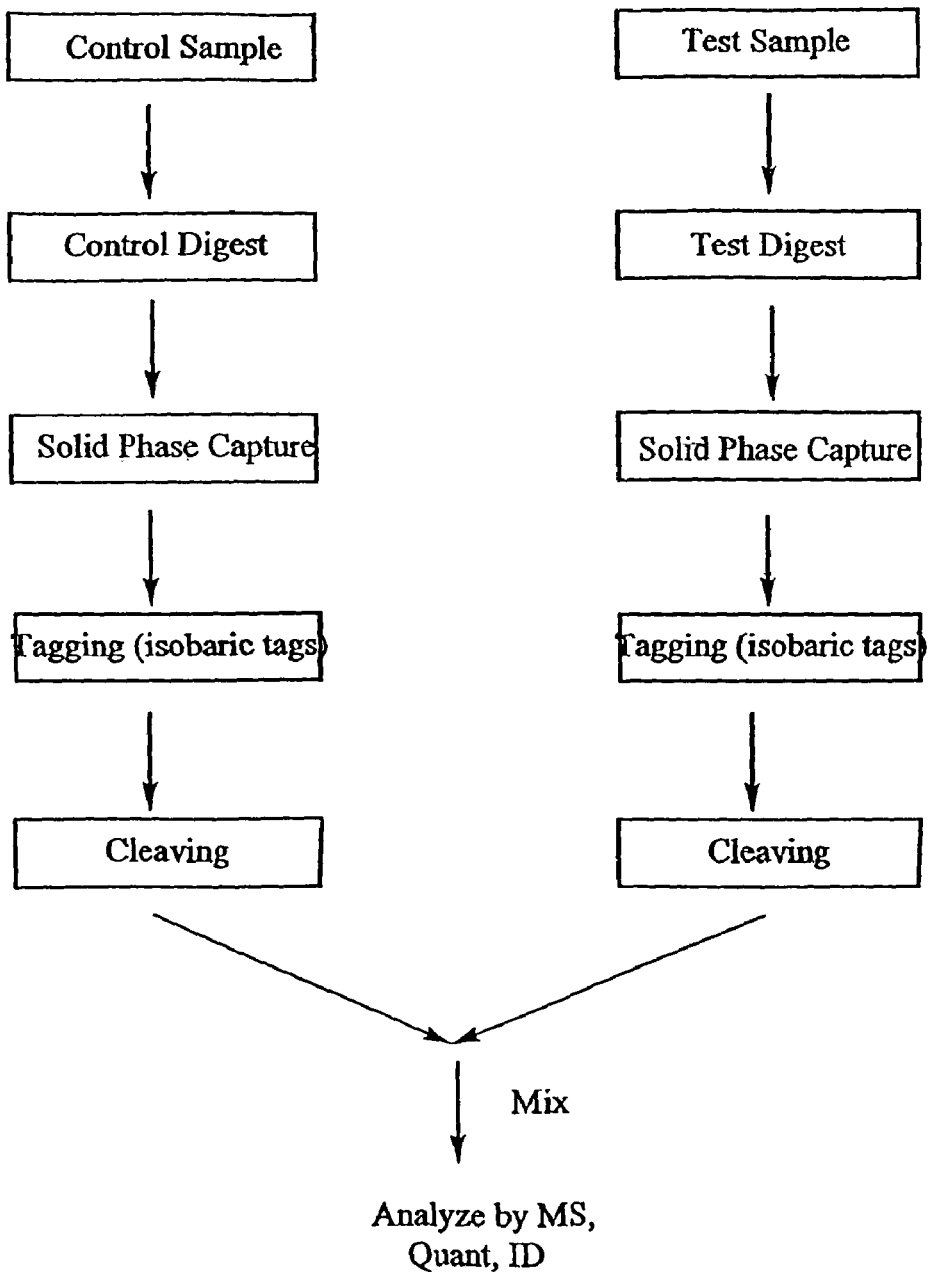
FIG. 21A is an illustration of a one possible workflow for proteomic analysis utilizing solid phase capture.
Figure 21:
FIG. 21B is an illustration of the generic parts of a support that can be used for capturing peptides and proteins.
FIG. 21C is an illustration of a specific support that can be used for capturing peptides and proteins by reaction of the thiol group of a cysteine moiety with the iodo acetate moiety of the support.
Figure 21:
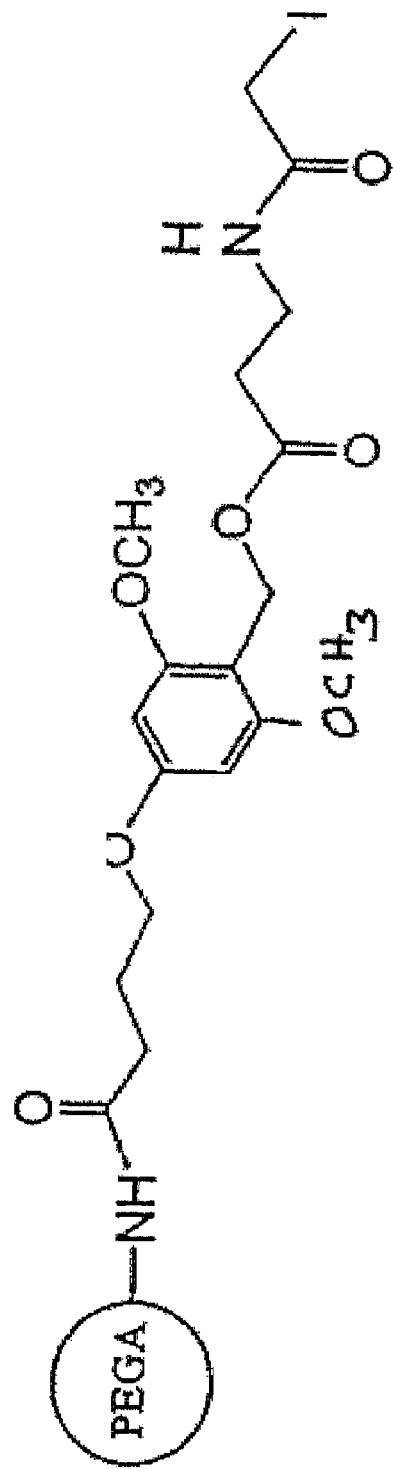
Figure 22:
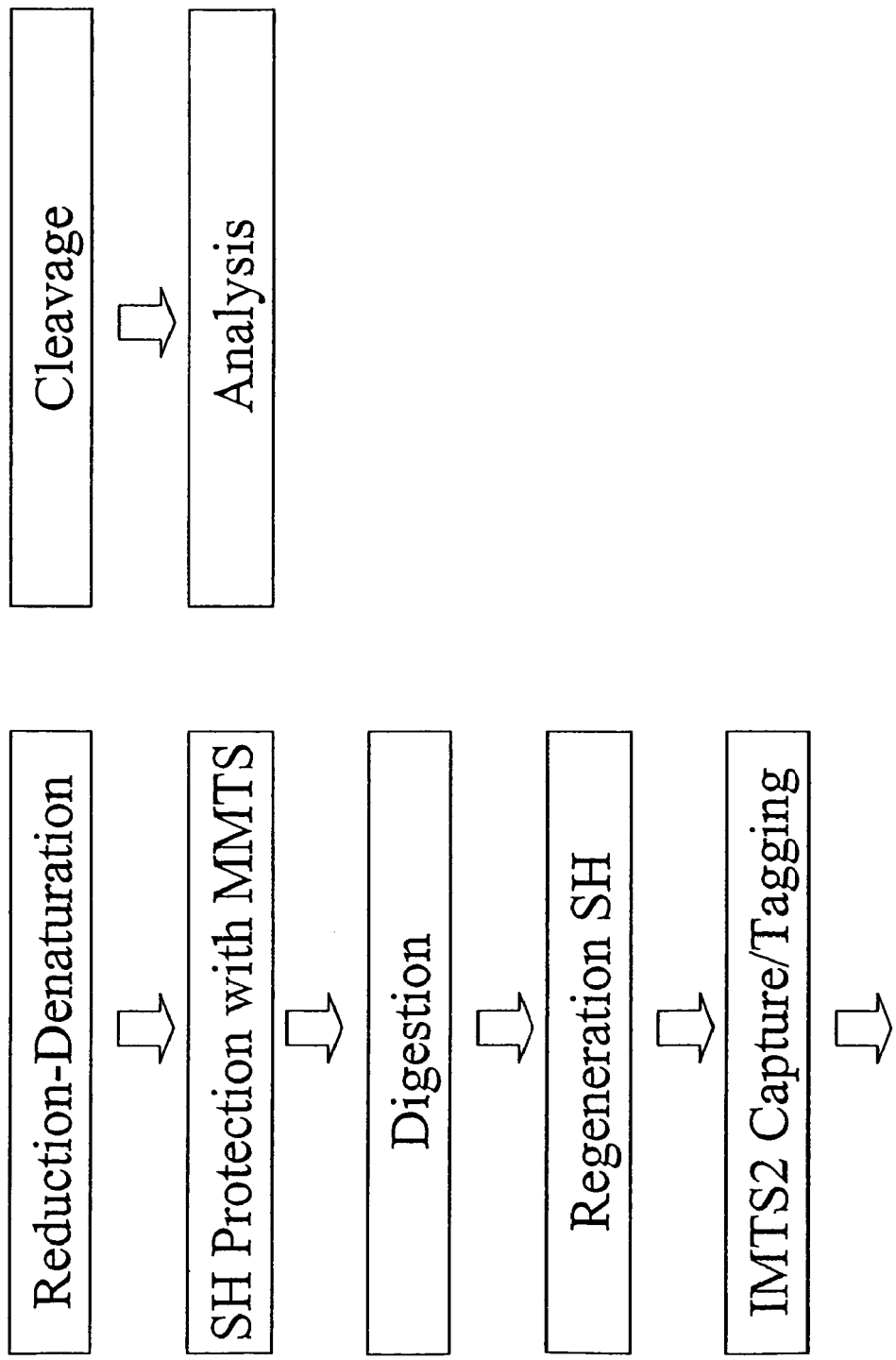
FIG. 22 is an illustration of a one possible workflow for proteomic analysis utilizing solid phase capture.

Another workflow is illustrated in FIGS. 21A and 22. FIG. 22 differs from 21A primarily in that FIG. 22 illustrates optional steps of blocking and deprotection of the thiol groups of cysteine that are involved with peptide capture. FIG. 21A illustrates how, in some embodiments, the "control" sample and the "test" samples can be digested with an enzyme and then components of the sample can be captured on a solid phase through a cleavable linker. For example, the support can comprise a cleavable linker and a reactive group that reacts with moieties of a peptide (See: FIG. 21B for an illustration the basic components of such a support). For example, a specific support suitable for capturing cysteine containing peptides is illustrated in FIG. 21C. The thiol group of the cysteine containing peptides can react with the iodoacetate group of the illustrated support. Because not all peptides are expected to comprise cysteine, this is a method for reducing the complexity of the sample to be analyzed since those peptides without a cysteine moiety will flow through the support and not be captures. Once immobilized, according to the processing method illustrated in FIG. 21A, the amine groups of the peptides can be labeled with a labeling reagent (See: FIG. 21A). The labeled peptide analytes can then be cleaved from the support and further processed (including forming a mixture) and/or analyzed (FIG. 21A).

Figure 23:
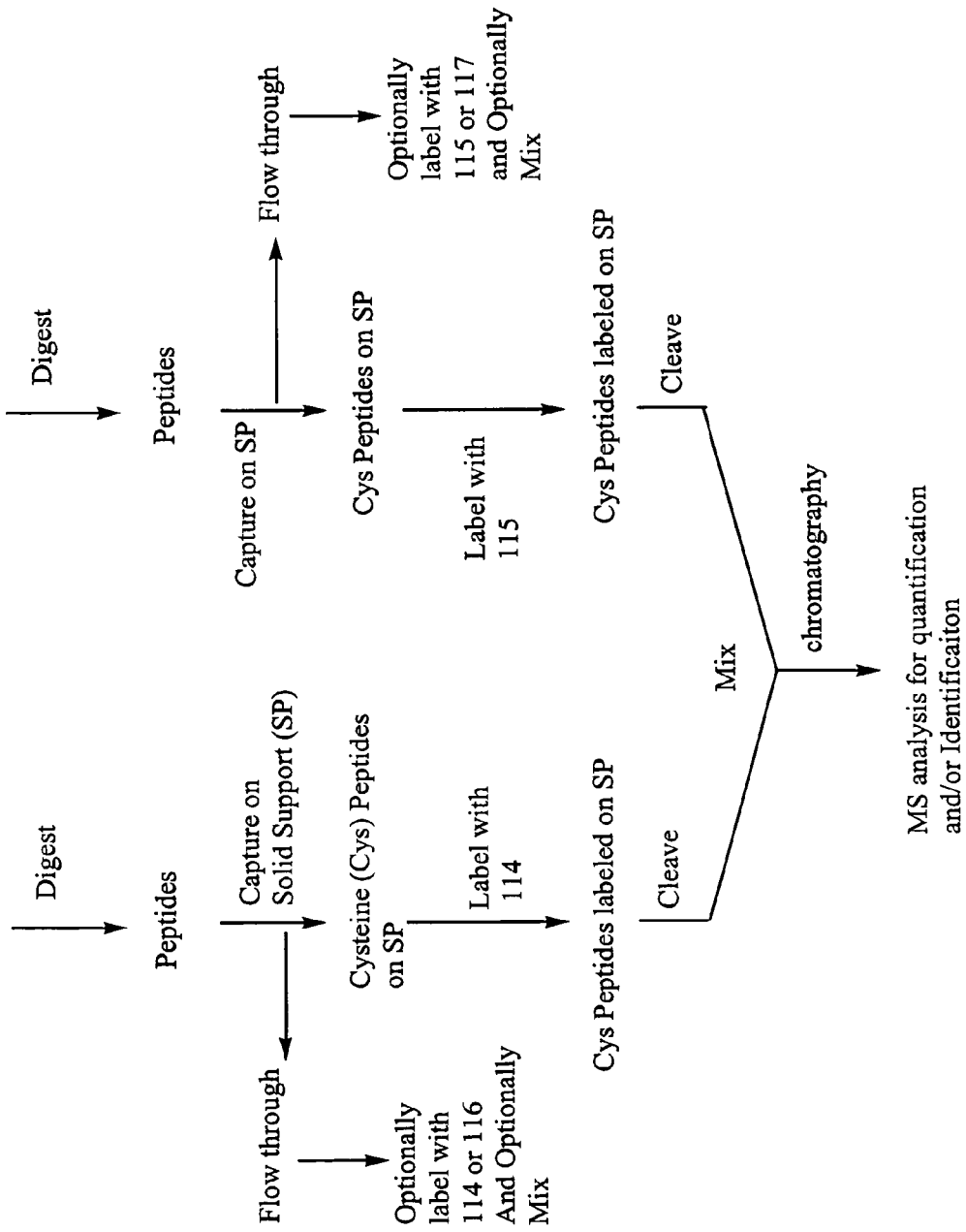
FIG. 23 is an illustration of a one possible workflow for proteomic analysis utilizing solid phase capture.
Figure 24:
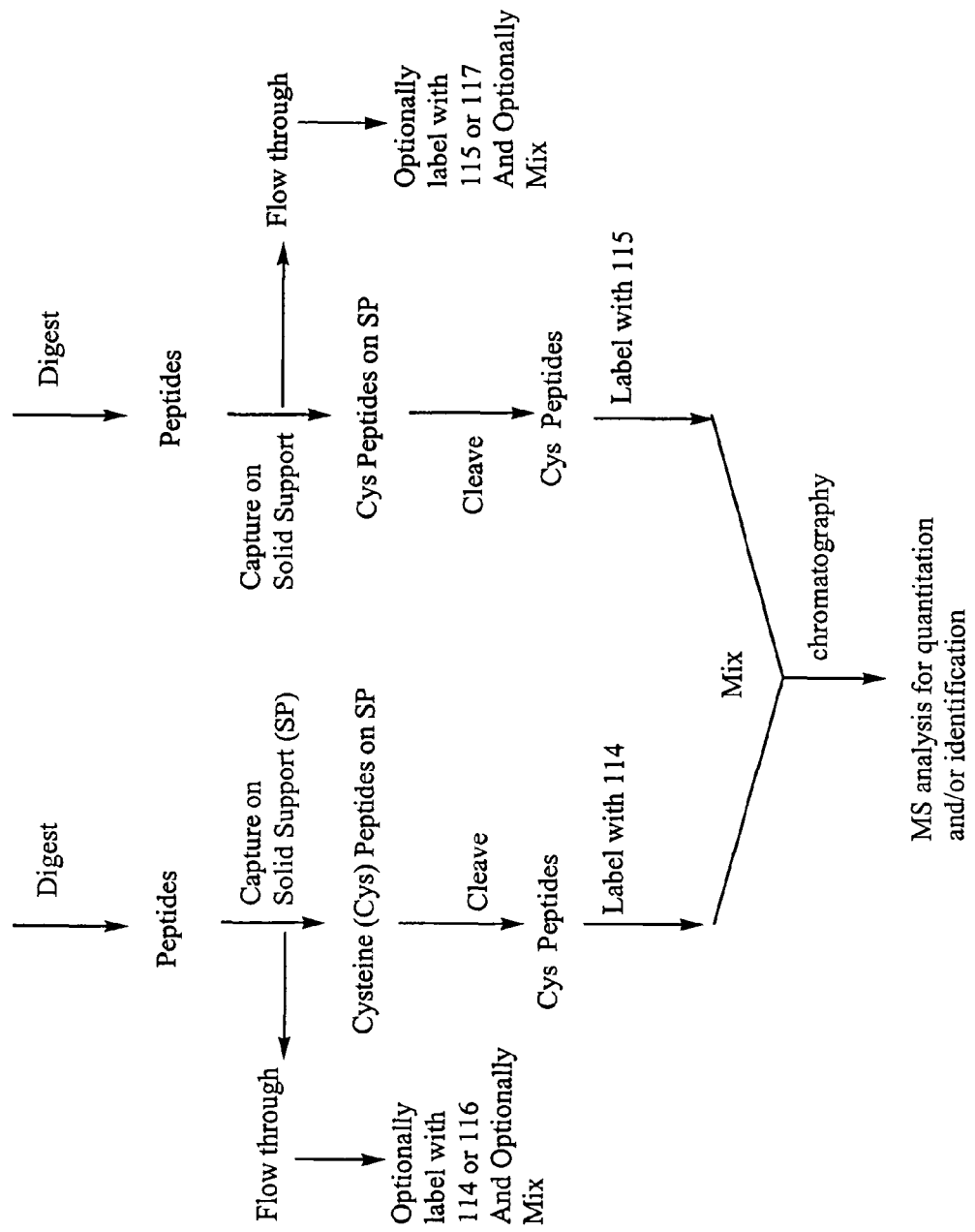
FIG. 24 is an illustration of a one possible workflow for proteomic analysis utilizing solid phase capture.

In some embodiments, the peptides that flow through the support (because they do not react with the functional group of the support) can (instead of being discarded) be collected, labeled with a labeling reagent and analyzed separately or together with the labeled peptides collected from the support. This workflow is illustrated in FIGS. 23 and 24. As illustrated, the peptides that flow through the solid support can be labeled with the same or with a different labeling reagent of a set of labeling reagents. Regardless of the labeling reagent, they can be optionally be mixed with the sample mixture that is analyzed by MS/MS analysis. They also can be independently analyzed. FIGS. 23 and 24 differ in that it is possible to label the peptides retained on the support either while still on the support (FIG. 23) or after they have been cleaved from the support (FIG. 24).

Figure 25:
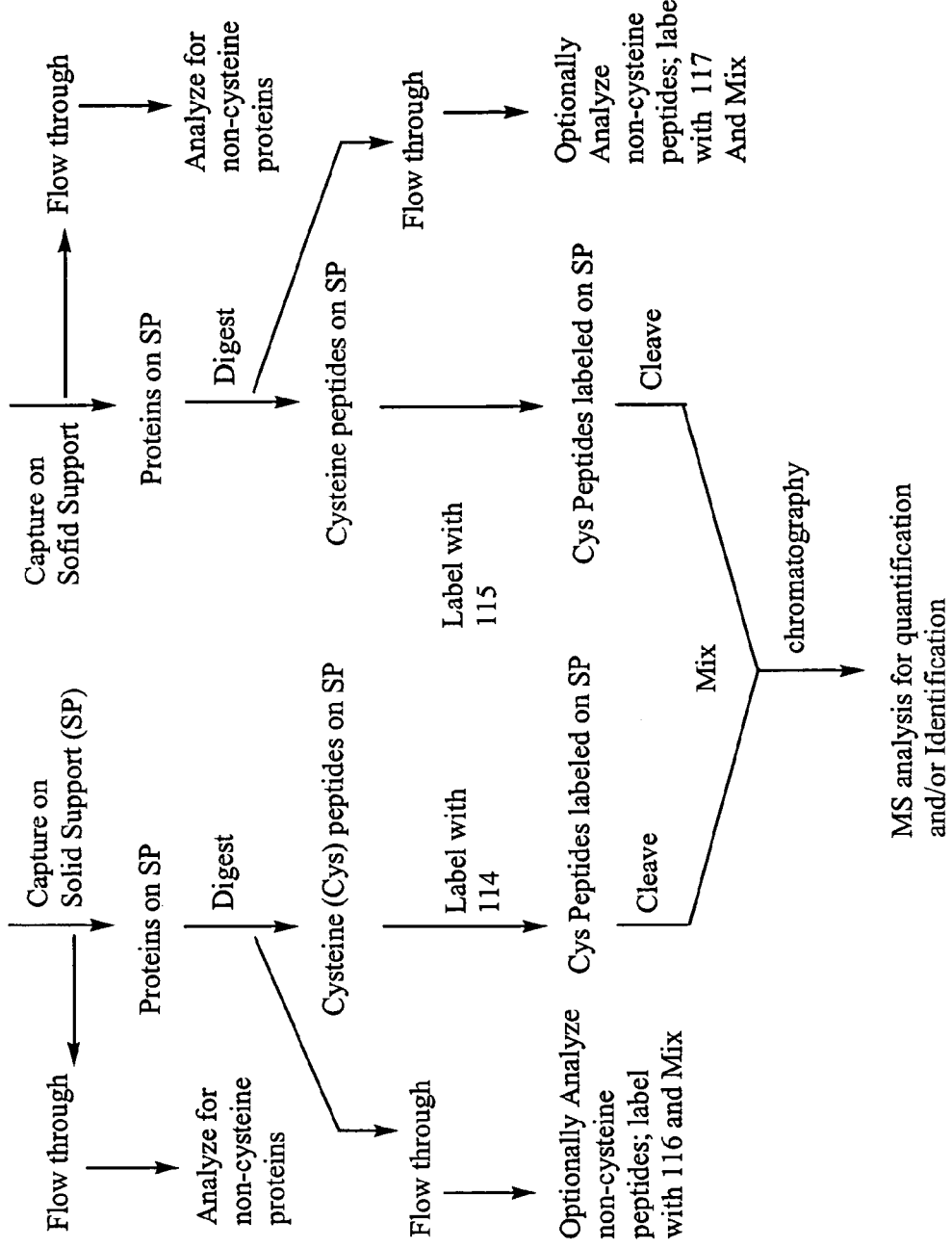
FIG. 25 is an illustration of a one possible workflow for proteomic analysis utilizing solid phase capture.

With reference to FIG. 25, it is also possible to use a solid support to capture the precursor proteins. As illustrated there can be two samples processed using a parallel path. A suitable support for capturing the cysteine moiety of proteins is illustrated in FIG. 21C. According to the figure, the support bound proteins can be digested. The peptides that do not comprise a cysteine moiety can be removed from the support with a wash and be collected. They can be optionally labeled and analyzed with the sample mixture or analyzed separately. The support bound cysteine comprising peptides can then be labeled with labeling reagent and cleaved from the support (option shown in the FIG. 25). The support bound cysteine comprising peptides can otherwise first be cleaved from the support and then labeled with labeling reagent (option not shown in FIG. 25). Labeled peptides from the different samples (optionally including the labeled peptides that do not comprise cysteine moieties) can be mixed and processed and/or analyzed.

B) Exemplary Workflows Involving Labeling Followed by Digestion

Whether or not a support is used to capture the precursor protein or analyte peptides, the step of labeling with a labeling reagent can be performed either before or after digestion of the precursor protein to the analyte peptides. Accordingly, for these workflows, the protein is labeled before digestion.

It is possible to reduce and cysteine block the sample protein, label the N-ε-lysine side chain amine groups of the sample protein with the labeling reagent and then digest the protein into labeled peptides. The labeled peptide analytes can be analyzed or they can be further processed (including preparing a sample mixture), for example by separation or by immobilization to a support. For example, it is possible to label the precursor protein by reaction of the labeling reagent with N-ε-lysine side chain amine groups of the sample protein and then optionally immobilize the labeled precursor protein to a support. The labeled protein can be cleaved from the support and then digested or the labeled protein can be digested while still support bound. In the latter case, support bound digestion will free peptides from the support that do not comprise a cysteine moiety. These can be collected and optionally analyzed either separately or as part of the sample mixture comprising the later released labeled peptides comprising cysteine moieties.

When the precursor proteins are labeled before digestion to peptides, the digestion pattern can be altered. For example, digestion with trypsin can be expected to produce predominately C-terminal arginine peptides because the N-ε-lysine side chain amine groups are modified with the label. Consequently, the activity of trypsin can be much like that of Arg-C. Because only those C-terminal arginine peptides that also comprise a lysine side chain can be labeled and therefore detectable in the mass spectrometer, this offers a way to further reduce the complexity of the sample to be further processed and/or analyzed.

In some embodiments, it is possible to reduce the protein and label the cysteine groups with labeling reagent (i.e. a thiol specific labeling reagent) and then digest the protein into labeled peptides for analysis. The labeled peptide analytes can be analyzed or can be further processed, for example by separation and/or immobilization to a support. For example, it is possible to immobilize labeled peptides to a support by reaction of the N-α-amine groups and/or the N-ε-amine groups of the lysine side chains with functional groups of the support. Supports with cleavable linkers for the immobilization of compounds comprising amine functional groups include resins comprising trityl linkers (See: Trityl chloride resin (Trityl-Cl) or 2-Chlorotrityl chloride resin available from Novabiochem (San Diego, Calif.)). This workflow is distinct from those described previously. The labeled analytes can be cleaved from the support, further processed and/or analyzed. This process might not provide substantial complexity reduction since all of the digested peptides are expected to comprise at least an N-α-amine group.

The foregoing examples are not intended to be exhaustive of various possible workflows. They are intended to be exemplary only. With regard to embodiments where labeling precedes digestion, it is possible to engage in further processing prior to performing the digestion.

C) Summary

Whilst the preceding discussion focused, by way of specific example, on proteomic analysis and the determination of peptides as analytes, the concepts described are intended to encompass many types of analytes for which the preceding workflows are applicable without the exercise of undue experimentation. Accordingly, the scope of this disclosure is not intended to be limited to any of these specific examples discussed.

IV. Mixtures

In some embodiments, this invention pertains to mixtures (i.e. sample mixtures). The mixtures can comprise at least two differentially labeled analytes, wherein each of the two-labeled analytes can originate from a different sample and comprise the formula: RP-X-LK-Y-Analyte. For each different label, some of the labeled analytes of the mixture can be the same and some of the labeled analytes can be different. The atoms, moieties or bonds, X, Y, RP and LK have been previously described and their characteristics disclosed. The mixture can be formed by mixing all, or a part, of the product of two or more labeling reactions wherein each labeling reaction uses a different labeling reagent of the general formula: RP-X-LK-Y-RG, wherein atoms, moieties or bonds X, Y, RP, LK RG have been previously described and their characteristics disclosed. The labeling reagents can be isotopically coded isomeric or isobaric labeling reagents. The unique reporter of each different labeling reagent can indicate from which labeling reaction each of the two or more labeled analytes is derived. The labeling reagents can be isomeric or isobaric. Hence, two or more of the labeled analytes of a mixture can be isomeric or isobaric. The mixture can be the sample mixture as disclosed in any of the above-described methods. Characteristics of the labeling reagents and labeled analytes associated with those methods have been previously discussed.

The analytes of the mixture can be peptides. The analytes of the mixture can be proteins. The analytes of the mixture can be peptides and proteins. The analytes of the mixture can be nucleic acid molecules. The analytes of the mixture can be carbohydrates. The analytes of the mixture can be lipids. The analytes of the mixture can be steroids. The analytes of the mixture can be small molecules of less than 1500 daltons. The analytes of the mixture comprise two or more analyte types. The analyte types can, for example, be selected from peptides, proteins, nucleic acids carbohydrates, lipids, steroids and/or small molecules of less than 1500 daltons.

In some embodiments, the label of each isobarically labeled analyte can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocyclic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

In some embodiments, the labeled analytes of the mixture are isobars and each comprise the formula:

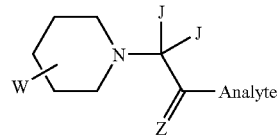

wherein Z, J and W have been previously described and their characteristics disclosed. For example, the sample mixture can comprise one or more isobarically labeled analytes of the formula:

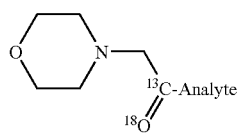 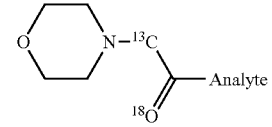

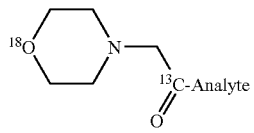 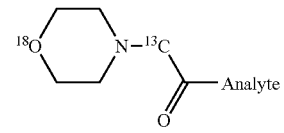

wherein isotopes of carbon 13 and oxygen 18 are used to balance the gross mass between the morpholine reporter and the carbonyl linker of the different labeling reagents.

In some embodiments, the sample mixture can comprise one or more isobarically labeled analytes of the formula:

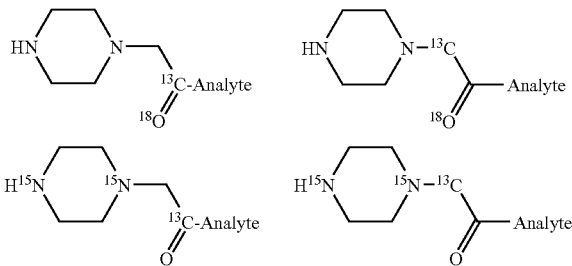
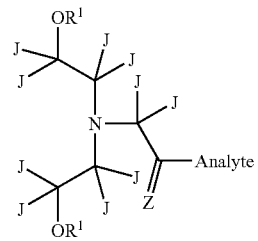

wherein isotopes of carbon 13, oxygen 18 and nitrogen 15 are used to balance the gross mass between the reporter and the carbonyl linker of the different labeling reagents. In some embodiments, the sample mixture can comprise one or more isobarically labeled analytes of the formula:

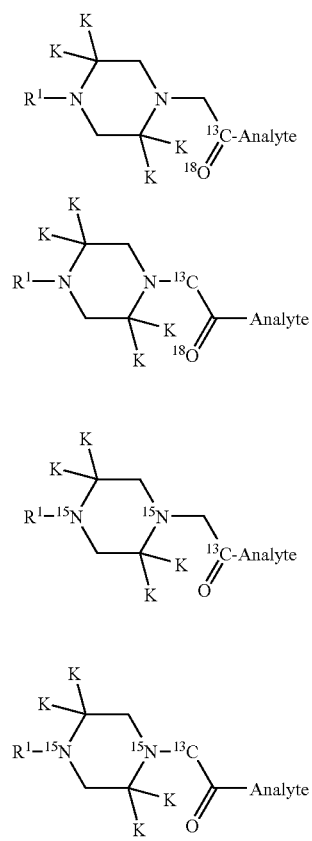

wherein: isotopes of carbon 13, oxygen 18 and nitrogen 15 are used to balance the gross mass between the reporter and the carbonyl linker of the different labeling reagents and wherein; 1) each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and 2) each K is independently selected as hydrogen or an amino acid side chain.

In some embodiments, the labeled analytes of the mixture are isobars and each comprise the formula:

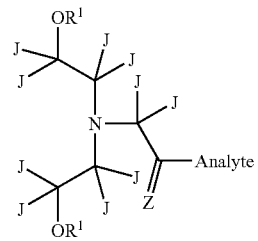

wherein: Z, J and $R^1$ have been previously described and their characteristics disclosed. For example, the sample mixture can comprise one or more isobarically labeled analytes of the formula:

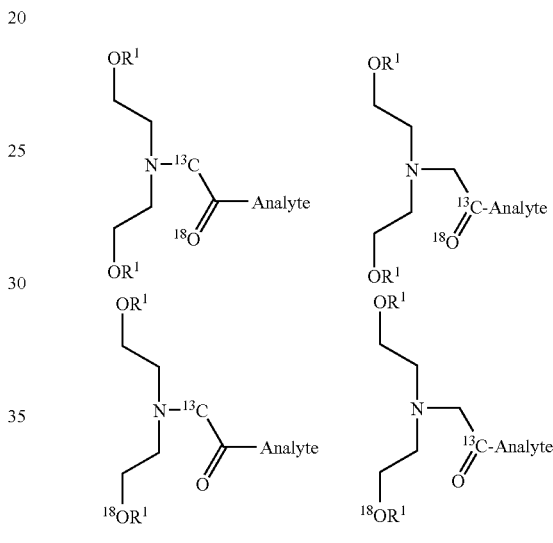

wherein isotopes of carbon 13 and oxygen 18 are used to balance the gross mass between the reporter and the carbonyl linker of the different labeling reagents.

In other embodiments, the labeled analytes can be generated by first reacting the analyte with a support comprising the labeling reagent, cleavably linked to the support through a cleavable linker, and then cleaving the labeled analyte from the support. For example the labeled analytes of the mixture can be one or more isobars comprising the general formula:

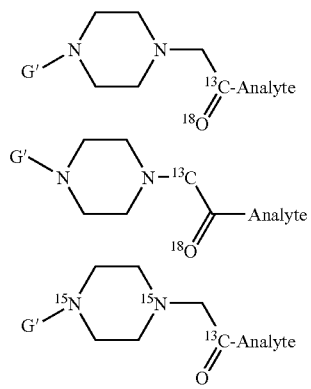

-continued

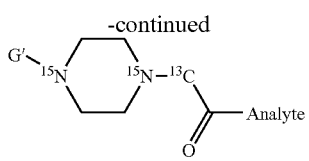

wherein: G' has been previously described and its characteristics disclosed.

V. Kits

In some embodiments, this invention pertains to kits. The kits can comprise a set of two or more labeling reagents of the formula: RP-X-LK-Y-RG and one or more reagents, containers, enzymes, buffers and/or instructions. The atoms, moieties or bonds X, Y, RP, LK RG have been previously described and their characteristics disclosed. The labeling reagents of a kit can be isomeric or isobaric. Other properties of the labeling reagents of the kits have likewise been disclosed. For example, the kits can be useful for the multiplex analysis of one or more analytes in the same sample, or in two or more different samples.

In some embodiments, the label of each isobarically labeled analyte can be a 5, 6 or 7 membered heterocyclic ring comprising a ring nitrogen atom that is N-alkylated with a substituted or unsubstituted acetic acid moiety to which the analyte is linked through the carbonyl carbon of the N-alkyl acetic acid moiety, wherein each different label comprises one or more heavy atom isotopes. The heterocyclic ring can be substituted or unsubstituted. The heterocyclic ring can be aliphatic or aromatic. Possible substituents of the heterocylic moiety include alkyl, alkoxy and aryl groups. The substituents can comprise protected or unprotected groups, such as amine, hydroxyl or thiol groups, suitable for linking the analyte to a support. The heterocyclic ring can comprise additional heteroatoms such as one or more nitrogen, oxygen or sulfur atoms.

In some embodiments, the different reagents of a kit are isobars and each comprise the formula:

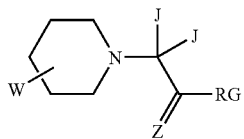

wherein RG, Z, J and W have been previously described and their characteristics disclosed. For example, the reagents of a kit can comprise one or more isobarically labeled reagents of the formula:

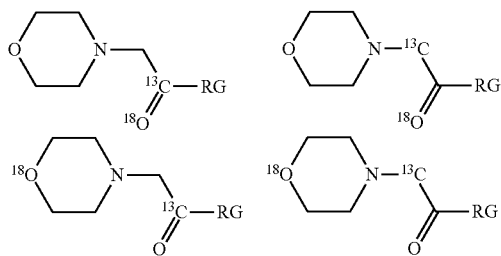

wherein RG is the reactive group and isotopes of carbon 13 and oxygen 18 are used to balance the gross mass between the morpholine reporter and the carbonyl linker of the different labeling reagents.

In some embodiments, the kit can comprise one or more isobarically labeled reagents of the formula:

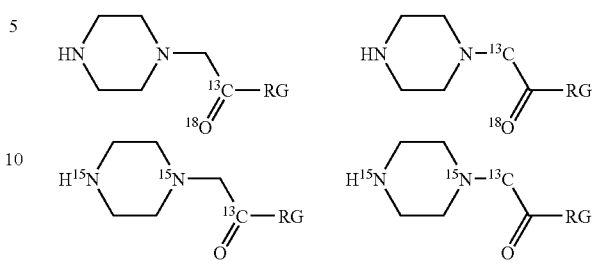

wherein RG is the reactive group and isotopes of carbon 13, oxygen 18 and nitrogen 15 are used to balance the gross mass between the reporter and the carbonyl linker of the different labeling reagents. In some embodiments, the reagents of a kit can comprise one or more isobarically labeled reagents of the formula:

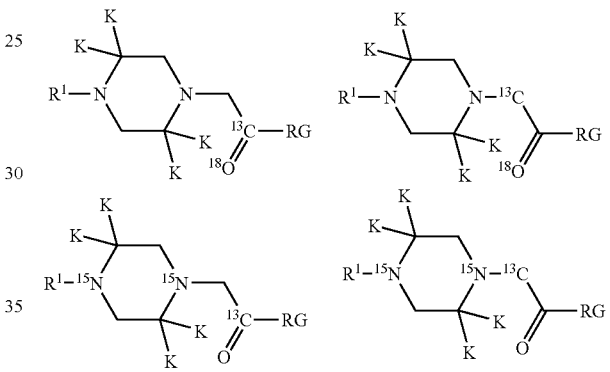

wherein: isotopes of carbon 13, oxygen 18 and nitrogen 15 are used to balance the gross mass between the reporter and the carbonyl linker of the different labeling reagents and wherein; 1) each $R^1$ is the same or different and is an alkyl group comprising one to eight carbon atoms which may optionally contain a heteroatom or a substituted or unsubstituted aryl group wherein the carbon atoms of the alkyl and aryl groups independently comprise linked hydrogen, deuterium and/or fluorine atoms; and 2) each K is independently selected as hydrogen or an amino acid side chain. In yet other embodiments, the labeled analytes of the kit are isobars and each comprises the formula:

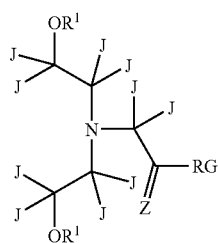

wherein: RG Z, J and $R^1$ have been previously described and their characteristics disclosed. For example, the reagents of a kit can comprise one or more isobarically labeled analytes of the formula:

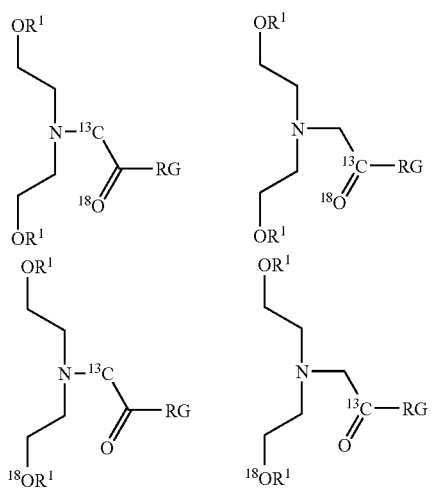

wherein RG has been previously described and disclosed and isotopes of carbon 13 and oxygen 18 are used to balance the gross mass between the reporter and the carbonyl linker of the different labeling reagents.

In some embodiments, this invention pertains to kits comprising one or more sets of supports, each support comprising a different labeling reagent, cleavably linked to the support through a cleavable linker. For example, the cleavable linker can be chemically or photolytically cleavable. The supports can be reacted with different samples thereby labeling the analytes of a sample with the same reporter/linker, and analytes of different samples with different reporter/linker combinations. Supports of a set that can be used in embodiments of this invention have the general formula: E-F-G-RP-X-LK-Y-RG, wherein E, F, G, RP, X, LK, Y and RG have been previously defined herein and their characteristics disclosed. Each different support of the set can comprise a unique reporter.

For example the supports of a kit can comprise two or more of the reagent supports of the formula:

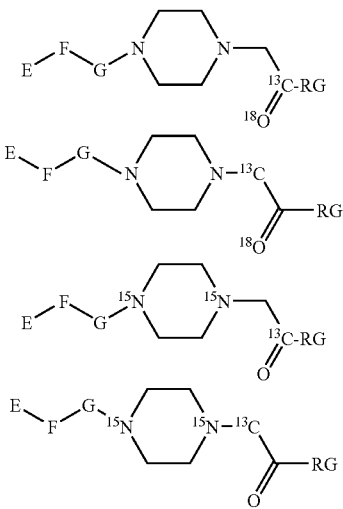

wherein: E, F, G and RG have been previously described and their characteristics disclosed.

In some embodiments, the kit comprises a proteolytic enzyme. The proteolytic enzyme can be trypsin, papain, pepsin, ArgC, LysC, V8 protease, AspN, pronase, chymotrypsin or carboxypeptidease C. In some embodiments, the kit can comprise instructions for using the labeling reagents to differentially label the analytes of different samples.

VI. Compositions

In some embodiments, this invention pertains to compositions that can be used as labeling reagents. The compositions can be labeling reagents of the formula: RP-X-LK-Y-RG, wherein the atoms, moieties or bonds X, Y, RP, LK RG have been previously described and their characteristics disclosed. The labeling reagents can be isomeric or isobaric. Other properties of the labeling reagents have likewise been disclosed. For example, the labeling reagents can be useful for the multiplex analysis of one or more analytes in the same sample, or in two or more different samples.

The labeling reagents can be isotopically enriched (coded) with at least one heavy atom isotope. The labeling reagents can be isotopically enriched to comprise two or more heavy atom isotopes. The labeling reagents can be isotopically enriched to comprise three or more heavy atom isotopes. The labeling reagents can be isotopically enriched to comprise four or more heavy atom isotopes. In some embodiments, at least one heavy atom isotope is incorporated into a carbonyl or thiocarbonyl group of the labeling reagent and at least one other heavy atom isotope is incorporated into the reporter group of the labeling reagent.

Each incorporated heavy atom isotope can be present in at least 80 percent isotopic purity. Each incorporated heavy atom isotope can be present in at least 93 percent isotopic purity. Each incorporated heavy atom isotope can be present in at least 96 percent isotopic purity.

The labeling reagents comprise a reporter group that contains a fixed charge or that is ionizable. The reporter group therefore can include basic or acidic moieties that are easily ionized. In some embodiments, the reporter can be a morpholine, piperidine or piperazine compound. In some embodiments, the reporter can be a carboxylic acid, sulfonic acid or phosphoric acid group containing compound. Accordingly, is some embodiments, the labeling reagents can be isolated in their salt form. For example, piperazine containing labeling reagents can be obtained as a mono-TFA salt, a mono-HCl salt, a bis-TFA salt or a bis-HCl salt. The number of counterions present in the labeling reagent can depend in the number of acidic and/or basic groups present in the labeling reagent.

In some embodiments, the labeling reagents can comprise a carbonyl or thiocarbonyl linker. Labeling reagents comprising a carbonyl or thiocarbonyl linker can be used in active ester form for the labeling of analytes. In an active ester, an alcohol group forms a leaving group (LG). In some embodiments, the alcohol (LG) of the active ester can have the formula:

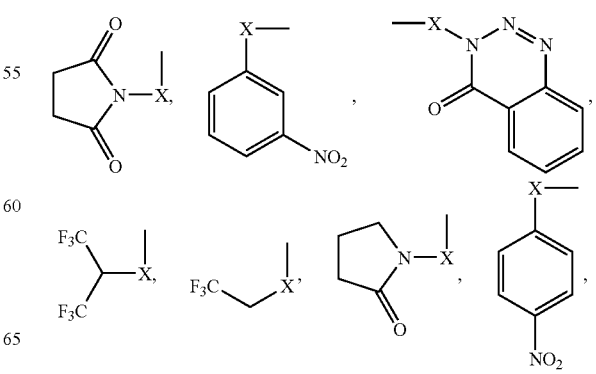

-continued

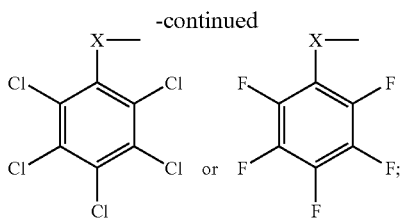

wherein X is O or S. The active ester can be an N-hydroxysuccinimidyl ester.

In some embodiments, the active ester compound can be a 5, 6 or 7 membered heterocyclic ring comprising a ring nitrogen atom that is N-alkylated with a substituted or unsubstituted acetic acid moiety to which the alcohol moiety of the active ester is linked through the carbonyl carbon of the N-alkyl acetic acid moiety, wherein the compound is isotopically enriched with one or more heavy atom isotopes. The heterocyclic ring of the active ester can be substituted with one or more substituents. The one or more substituents can be alkyl, alkoxy or aryl groups. The one or more substituents can be alkylamine, alkylhydroxy or alkylthio groups. The one or more substituents can be protected or unprotected amine groups, hydroxyl groups or thiol groups. The heterocyclic ring can be aliphatic. The heterocyclic ring can be aromatic. The heterocyclic ring can comprise one or more additional nitrogen, oxygen or sulfur atoms.

In some embodiments, the active ester compound can be an N-substituted morpholine acetic acid active ester compound of the formula:

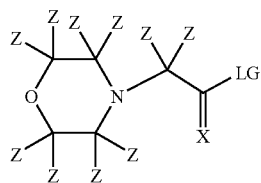

or a salt thereof, wherein; LG is the leaving group of an active ester; X is O or S; each Z is independently hydrogen, deuterium, fluorine, chlorine, bromine, iodine, an amino acid side chain or a straight chain or branched C1-C6 alkyl group that may optionally contain a substituted or unsubstituted aryl group wherein the carbon atoms of the alkyl and aryl groups each independently comprise linked hydrogen, deuterium or fluorine atoms. In some embodiments, Z independently can be hydrogen, deuterium, fluorine, chlorine, bromine or iodine. In some embodiments, Z independently can be hydrogen, methyl or methoxy. In some embodiments, X is $^{16}$O or $^{18}$O. The nitrogen atom of the morpholine ring can be $^{14}$N or $^{15}$N. In some embodiments, the active ester is a compound comprising the formula:

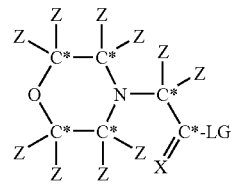

wherein each C* is independently $^{12}$C or $^{13}$C; LG is the leaving group of an active ester; X is O or S; and each Z is independently hydrogen, deuterium, fluorine, chlorine, bromine, iodine, an amino acid side chain or a straight chain or branched C1-C6 alkyl group that may optionally contain a substituted or unsubstituted aryl group wherein the carbon atoms of the alkyl and aryl groups each independently comprise linked hydrogen, deuterium or fluorine atoms.

In some embodiments, the active ester compound can be an N-substituted piperidine acetic acid active ester compound of the formula:

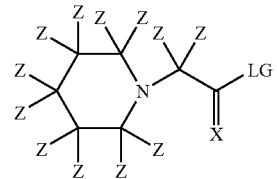

or a salt thereof, wherein; LG is the leaving group of an active ester; X is O or S; each Z is independently hydrogen, deuterium, fluorine, chlorine, bromine, iodine, an amino acid side chain or a straight chain or branched C1-C6 alkyl group that may optionally contain a substituted or unsubstituted aryl group wherein the carbon atoms of the alkyl and aryl groups each independently comprise linked hydrogen, deuterium or fluorine atoms. In some embodiments, Z independently can be hydrogen, deuterium, fluorine, chlorine, bromine or iodine. In some embodiments, Z independently can be hydrogen, methyl or methoxy. In some embodiments X is $^{16}$O or $^{18}$O. The nitrogen atom of the piperidine ring can be $^{14}$N or $^{15}$N. In some embodiments, the active ester is a compound comprising the formula:

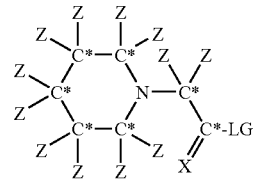

wherein each C* is independently $^{12}$C or $^{13}$C; LG is the leaving group of an active ester; X is O or S; and each Z is independently hydrogen, deuterium, fluorine, chlorine, bromine, iodine, an amino acid side chain or a straight chain or branched C1-C6 alkyl group that may optionally contain a substituted or unsubstituted aryl group wherein the carbon atoms of the alkyl and aryl groups each independently comprise linked hydrogen, deuterium or fluorine atoms.

In some embodiments, the active ester compound can be an N-substituted piperidine acetic acid active ester compound of the formula:

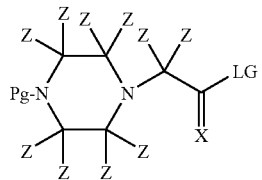

or a salt thereof, wherein; LG is the leaving group of an active ester; X is O or S; Pg is an amine protecting group; and each Z is independently hydrogen, deuterium, fluorine, chlorine, bromine, iodine, an amino acid side chain or a straight chain or branched C1-C6 alkyl group that may optionally contain a substituted or unsubstituted aryl group wherein the carbon atoms of the alkyl and aryl groups each independently comprise linked hydrogen, deuterium or fluorine atoms. In some embodiments, Z independently can be hydrogen, deuterium, fluorine, chlorine, bromine or iodine. In some embodiments, Z independently can be hydrogen, methyl or methoxy. In some embodiments X is $^{16}O$ or $^{18}O$. In some embodiments, each nitrogen atom of the piperazine ring is $^{14}N$ or $^{15}N$. In some embodiments, the active ester is a compound comprising the formula:

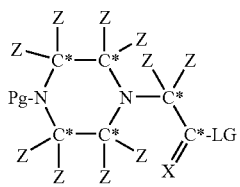

wherein each C* is independently $^{12}C$ or $^{13}C$; LG is the leaving group of an active ester; X is O or S; Pg is an amine protecting group and each Z is independently hydrogen, deuterium, fluorine, chlorine, bromine, iodine, an amino acid side chain or a straight chain or branched C1-C6 alkyl group that may optionally contain a substituted or unsubstituted aryl group wherein the carbon atoms of the alkyl and aryl groups each independently comprise linked hydrogen, deuterium or fluorine atoms.

VII. Exemplary N-Substituted Piperazine Based Labeling Reagents

A. Preparation of N-Substituted Piperazines comprising Heavy Atom Isotopes

In some embodiments, this invention pertains to a method for the production of isotopically enriched N-substituted piperazines, and the N-substituted piperazines themselves. According to the method, a partially protected amino acid can be condensed with an N-substituted amino acid ester wherein at least one of the two amino acids comprises a heavy atom isotope such as, for example, $^{18}O$, $^{15}N$, $^{13}C$, $^{81}Br$, $^{37}Cl$ or deuterium. When condensing the two amino acids, any side chain reactive groups can be protected as they would be for the condensation of amino acids to form peptides. Similarly, the condensation chemistry can be chosen from the various methods known for condensing amino acids. These include, but are not limited to, the use of carbodiimides (e.g. dicyclohexylcarbodiimide, DCC), active esters, mixed anhydride formation and the like.

The partially protected amino acid comprises an amine-protecting group (N-protecting group), such as tert-butyloxycarbonyl (t-boc); a well-known protecting group in peptide synthesis. Numerous other suitable N-protecting groups are well known in the peptide synthesis art. The partially protect amino acid can comprise a side chain protecting where the amino acid comprises a reactive side chain moiety. Numerous suitable side chain protecting groups are likewise known in the peptide synthesis art. The amino acid can be any natural amino acid (e.g. glycine, alanine, lysine) or non-natural amino acid of basic structure:

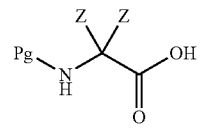

wherein Pg can be the N-protecting group. Each group Z can be independently hydrogen, deuterium, fluorine, chlorine, bromine, iodine, an amino acid side chain, a straight chain or branched C1-C6 alkyl group that may optionally contain a substituted or unsubstituted aryl group wherein the carbon atoms of the alkyl and aryl groups each independently comprise linked hydrogen, deuterium or fluorine atoms or a straight chain or branched C1-C6 alkoxy group that may optionally contain a substituted or unsubstituted aryl group wherein the carbon atoms of the alkyl and aryl groups each independently comprise linked hydrogen, deuterium or fluorine atoms. In some embodiments, each Z is independently hydrogen, methyl or methoxy. In some embodiments, each Z is hydrogen, deuterium, fluorine, chlorine, bromine or iodine. An alkyl ether group, as used herein, can include one or more polyethylene glycol substituents. Similarly, the alkoxy group, as used herein, can comprise ether and/or polyethylene glycol substituents. The N-protecting group can be an acid labile protecting group. The N-protecting group can be a base labile protecting group.

The N-substituted amino acid ester can be any natural amino acid (e.g. glycine, alanine, lysine) or non-natural amino acid of basic structure:

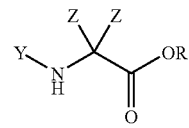

wherein Z is previously defined. The group Y can be a straight chain or branched C1-C6 alkyl group or a straight chain or branched C1-C6 alkyl ether group wherein the carbon atoms of the alkyl group or alkyl ether group each independently comprise linked hydrogen, deuterium or fluorine atoms. In some embodiments, Y is methyl, ethyl, n-propyl, isopropyl, n-butyl, isobutyl, sec-butyl or tert-butyl. The group R can be a straight chain or branched C1-C6 alkyl group or a substituted or unsubstituted phenyl group, wherein the carbon atoms of the alkyl group or phenyl group each independently comprise linked hydrogen, deuterium or fluorine atoms. In some embodiments, the N-substituted amino acid ester is the ester (e.g. methyl or ethyl) of sarcosine, which is an ester of N-methyl glycine.

Every possible permutation of $^{15}N$ or $^{13}C$ labeled glycine is commercially available. Likewise, other natural amino acids are commercially available with one or more incorporated heavy atom isotopes. Because glycine, and other amino acids, comprising one or more heavy atom isotopes are commercially available, these amino acids can be easily incorporated into the procedure for the production of N-substituted piperazines. The amino acids comprising heavy atom isotopes can be N-protected using procedures well-known in peptide chemistry. For example, the amino acids can be N-protected with a 9-fluorenylmethoxycarbonyl (Fmoc) group or a t-boc group. Furthermore, the amino acids comprising heavy atom isotopes can be N-alkylated and converted to an ester of the amino acid using well-known procedures. Accordingly, heavy atom isotope containing starting materials for the preparation of N-substituted piperazines, as described herein, are either commercially available, or can be easily prepared from commercially available amino acids using no more than routine experimentation.

According to the method, the two amino acids can be condensed to thereby produce an N-protected peptide dimer as an ester. The N-protected peptide dimer ester can comprise one or more heavy atom isotopes via the incorporation of the one or more amino acids comprising one or more heavy atom isotopes. The N-protected peptide dimer ester can comprise one heavy atom isotope, two heavy atom isotopes, three heavy atom isotopes, four heavy atom isotopes, five heavy atom isotopes or six heavy atom isotopes. The N-protected peptide dimer can comprise greater than six heavy atom isotopes. The N-protected peptide dimer ester can have the general formula:

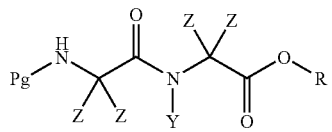

wherein Pg, R, Y and Z are previously defined.

According to the method, the N-protected peptide dimer ester can then be cyclized to form a 6-membered cyclic dione. Cyclization proceeds by removing the N-protecting group of the N-protected peptide dimer ester and driving the reaction of the deprotected amine with the ester group. The reaction can be carried out under basic conditions and can be heated to speed production of the product. The product of the cyclization can have the general formula:

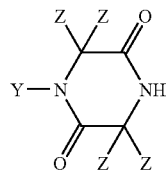

wherein Y and Z are previously defined.

According to the method, the ketone groups of the cyclic dione can then be reduced to form the desired N-substituted piperazine comprising one or more heavy atom isotopes. The reduction can be performed using a reducing agent, such as lithium aluminum hydride (LAH) or Red-Al (Sigma-Aldrich). The product, in some embodiments being a volatile oil, can be optionally temporarily modified (e.g. protected) to aid in isolation. Because piperazine comprises two basic nitrogen atoms, the product can, in some embodiments, be isolated as a mono or bis-acid salt. For example, the N-substituted piperazine comprising one or more heavy atom isotopes can be isolated as a mono-TFA salt, a mono-HCl salt, a bis-TFA salt or a bis-HCl salt.

Figure 13:
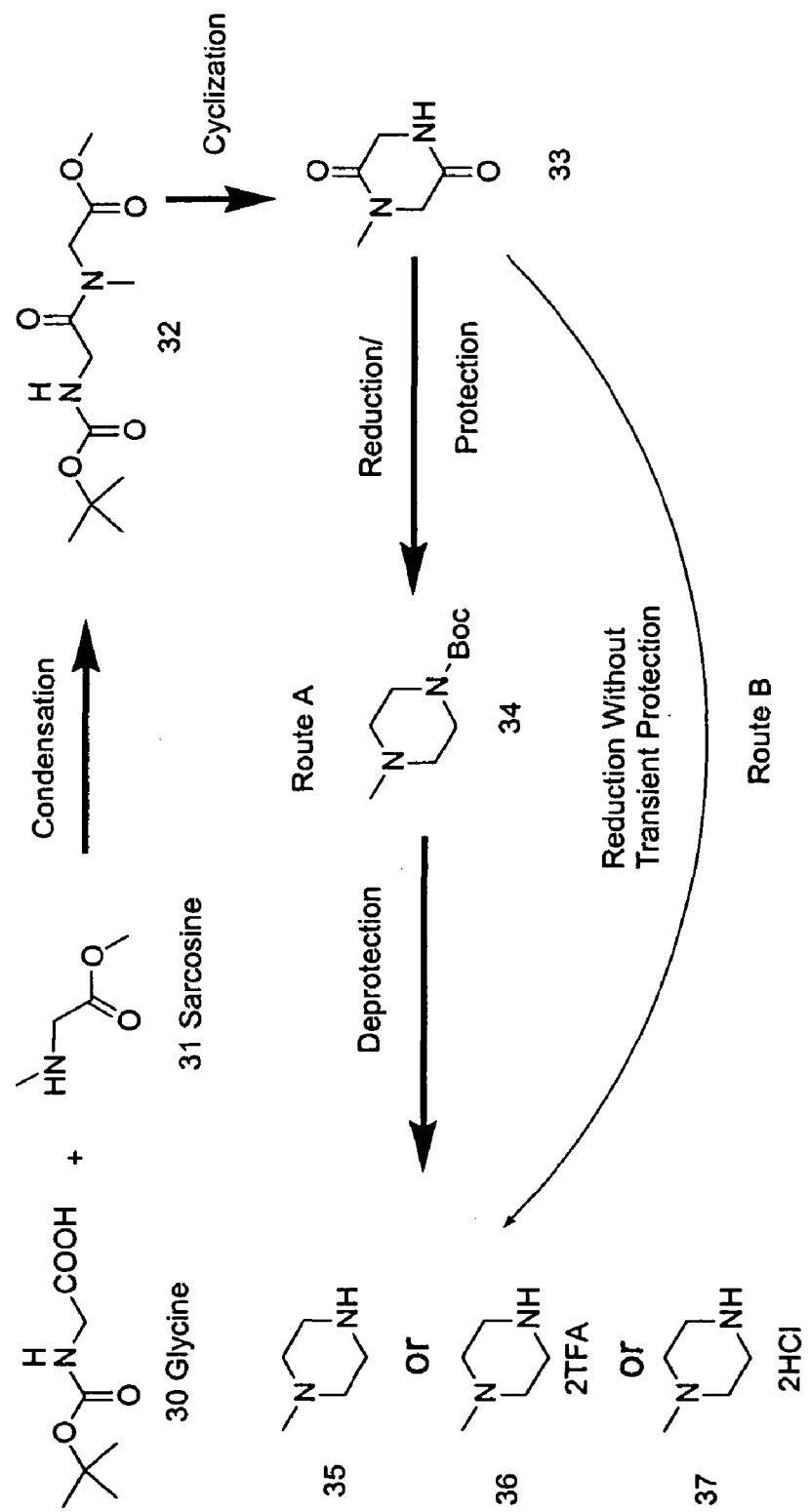
FIG. 13 is an illustration of a synthetic scheme for the synthesis of N-methyl piperazines.

FIG. 13 illustrates the application of the aforementioned general procedure to the production of N-methyl piperazine. Examples 10-13 describe the application of the illustrated procedure to the production of three different N-methyl piperazines each comprising 1-3 heavy atom isotopes.

With reference to FIG. 13 and Examples 10-13, t-boc protected glycine (30) is condensed with sarcosine methyl ester (31) to thereby produce the dipeptide (32). The t-boc group is removed and the dipeptide is cyclized to the cyclic dione (33). The ketone groups of the dione are then reduced to produce N-methyl piperazine. The N-methyl piperazine product can either be transiently protected (34) or can be obtained directly from the reduction (35). The product can also be obtained as a salt of an acid (e.g. TFA salt (36) or HCl (37)).

In summary, a wide variety of N-substituted piperazine compounds, unlabeled or labeled with one or more heavy atom isotopes, can be produced by the aforementioned process. Consequently, the present invention contemplates all possible isotopically enriched N-substituted piperazine compound comprising one or more heavy atom isotopes of the general formula:

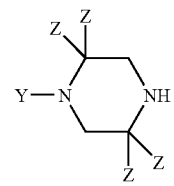

including all possible salt forms (a salt or mixture of salts) thereof, wherein Y and Z are previously defined. Also contemplated are isotopically enriched N-substituted piperazine compounds, whether or not a salt form, existing in hydrate form (i.e. one or more complexed heavy or light water molecules).

B. Preparation of N-Substituted Piperazine Acetic Acids Comprising Heavy Atom Isotopes In some embodiments, this invention pertains to methods for the production of isotopically enriched N-substituted piperazine acetic as well as the isotopically enriched N-substituted piperazine acetic acids. In some embodiments, an N-substituted piperazine can be reacted with a halo acetic acid moiety comprising one or more heavy atom isotopes. In this context, halo refers to the halogens, chlorine, bromine and iodine. In still some other embodiments, an N-substituted piperazine comprising one or more heavy atom isotopes can be reacted with a halo acetic acid moiety. In some other embodiments, an N-substituted piperazine comprising one or more heavy atom isotopes can be reacted with a halo acetic acid moiety comprising one or more heavy atom isotopes. Accordingly, the heavy atom isotopes found in the product N-substituted piperazine acetic acids can be introduced by way of the piperazine, by way of the halo acetic acid moiety or by way of both the piperazine and the halo acetic acid moiety. As will be discussed in more detail below, $^{18}O$ can also be introduced into the carboxylic acid moiety of an N-substituted piperazine acetic acid by way of exchange with $H_2^{18}O$.

Numerous light N-substituted piperazines (e.g. N-methyl and N-ethyl piperazine) are commercially available. Furthermore, Section A above describes the preparation of N-substituted piperazine comprising one or more heavy atoms from commercially available amino acids. Both light and heavy N-substituted piperazine compounds can be used to produce the N-substituted piperazine acetic acids comprising one or more heavy atom isotopes.

Numerous light and heavy halo acetic acid moieties are commercially available. The halo acetic acid moiety to be reacted with the N-substituted piperazine can be purchased as the carboxylic acid or as an ester of the carboxylic acid (e.g. the methyl ester, ethyl ester or phenyl ester). If only the carboxylic acid is available and the ester is desired, the ester can be prepared using well-known esterification methods. If only the ester is available and the carboxylic acid is desired, the ester can be hydrolyzed to produce the carboxylic acid. Either the carboxylic acid or the ester can be used in the alkylation reaction provided that at least one additional equivalent of base is required if the carboxylic acid is used. If the ester is used to perform the alkylation, the product ester can be hydrolyzed to produce the N-substituted piperazine acetic acid. General structures for the carboxylic acid and the ester compounds that can be used to alkylate N-substituted piperazines are:

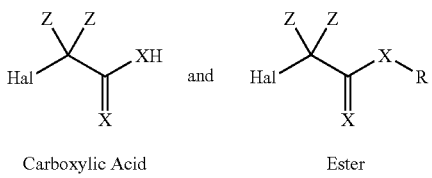

Carboxylic Acid    Ester wherein Z and R are defined above. Hal is a halogen (Cl, Br or I) and X is oxygen (O) or sulfur (S). In some embodiments, X is $^{16}O$ or $^{18}O$. One or more of the atoms of the halo acetic acid compound can be a heavy atom isotope.

The alkylation of an N-substituted piperazine with a halo acetic acid moiety proceeds under basic conditions. The base need only be strong enough to deprotonate piperazine but can be selected to not substantially react with the halo acetic acid moiety. In some embodiments, two or more equivalents of N-substituted piperazine can be used, as N-substituted piperazine is a base. If it is desirable to use only one equivalent of N-substituted piperazine (for example, when the N-substituted piperazine is labeled with one or more heavy atom isotopes and is therefore valuable), other bases can be used. Suitable bases include, but are not limited to, hindered bases such as triethylamine ($Et_3N$) and diisopropylethyamine (DIEPA). Other suitable bases include sodium carbonate and potassium carbonate. Hindered bases are a good choice because they do not react substantially with the halo acetic acid moiety.

Figure 14A:
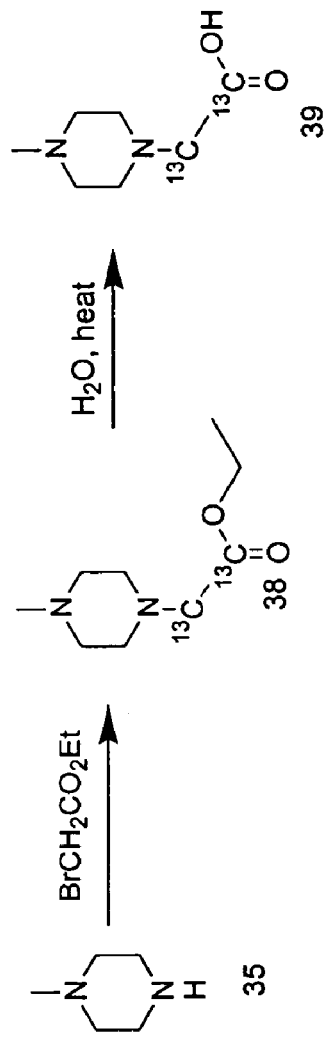
FIG. 14A is an illustration of a synthetic scheme for the synthesis of N-methyl piperazine acetic acids.
Figure 14B:
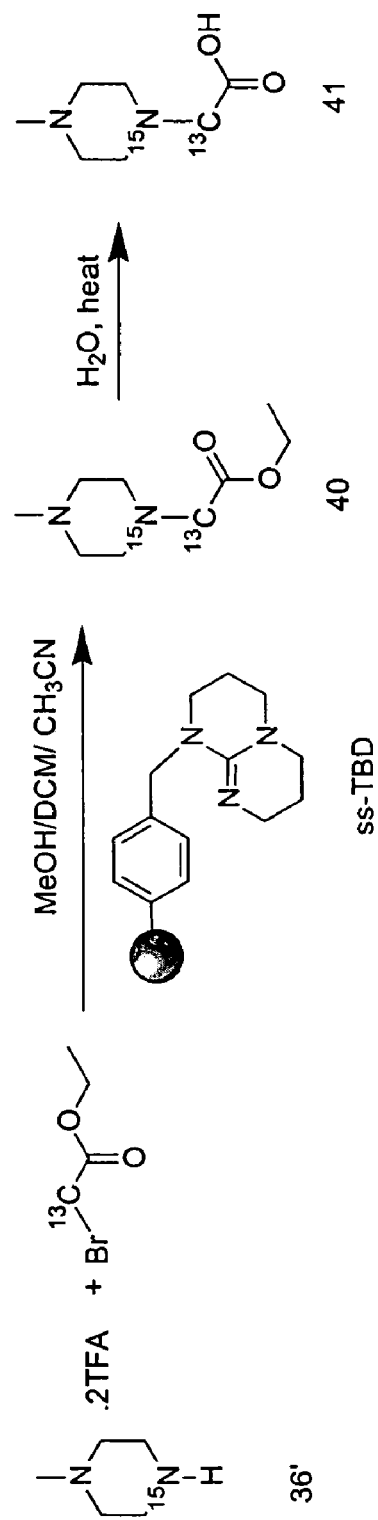
FIG. 14B is an illustration of another synthetic scheme for the synthesis of N-methyl piperazine acetic acids.

A solid phase base, such as 1,5,7-Triazabicyclo[4.4.0]dec-5-ene (TBD) bound to polystyrene crosslinked with 2% DVB, Capacity (base): ~2.6 mmol/g (ss-TBD, Fluka, P/N 90603) can also be used (See FIG. 14B). A solid phase base has the advantage that it is easily, and completely, removed from the product by filtration once the alkylation reaction has been completed. Accordingly, the resulting product is not contaminated with salt of the base.

If the carboxylic acid is used to alkylate the N-substituted piperazine, the reaction can produce a product of the general formula:

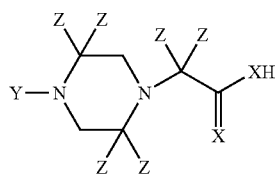

or a salt form thereof, wherein X, Y and Z have been previously defined. One or more atoms of the N-substituted piperazine acetic acid can be a heavy atom isotope. Also contemplated are isotopically enriched N-substituted piperazine acetic acid compounds, whether or not a salt form, existing in hydrate form (i.e. one or more complexed heavy or light water molecules).

If the ester is used to alkylate the N-substituted piperazine, the reaction will produce an ester of the general formula:

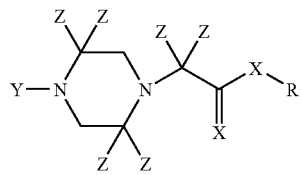

or a salt form thereof, wherein R, X, Y and Z have been previously defined. Also contemplated are isotopically enriched N-substituted piperazine acetic acid ester compounds, whether or not a salt form, existing in hydrate form (i.e. one or more complexed heavy or light water molecules). One or more atoms of the N-substituted piperazine acetic acid ester can be a heavy atom isotope. The N-substituted piperazine acetic acid ester can be converted to the N-substituted piperazine acetic acid of general formula:

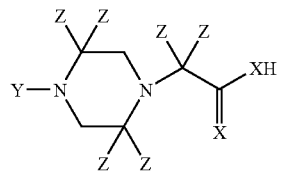

by hydrolysis of the ester. The N-substituted piperazine acetic acid can exist in salt form and/or in hydrate form. Depending on the state of protonation of the ester, it may or may not be necessary to add base to aqueous solution to perform the hydrolysis because piperazine is basic (unless neutralized by acid). Accordingly, base can be added as required to induce the hydrolysis of the ester to the carboxylic acid, but in some embodiments it will not be required. Hydrolysis can also be performed under aqueous acidic conditions.

N-substituted piperazine acetic acid can be zwitterionic. Because it comprises a carboxylic acid group (or thio acid group) and two basic nitrogen atoms, it can exist in at least four different forms. It can exist completely deprotonated as its carboxylate anion. It can exist as its mono protonated zwitterion. It can exist as a monobasic salt (e.g. mono-TFA or mono-HCl salt). It can also exist as its dibasic salt (e.g. bis-TFA or bis-HCl salt). The state of protonation of the product is a function of the conditions under which it was isolated. All protonation states of N-substituted piperazine acetic acid are contemplated as embodiments of the present invention, including compounds is hydrate form.

With reference to FIGS. 14A and 14B, as well as Examples 14 and 15, respectively, the production of two different isotopically enriched N-methyl piperazine acetic acid compounds is described. In FIG. 14A and Example 14, two equivalents of commercially available unlabeled N-methyl piperazine is reacted with ethyl bromoacetate to produce a N-methyl piperazine acetic acid compound comprising two $^{13}C$ atoms. Because N-methyl piperazine is basic, hydrolysis of the ethyl ester proceeded by merely heating the compound in an aqueous solution.

With reference to FIG. 14B and Example 15, the starting piperazine is a bis-TFA salt of $^{15}N$ labeled N-methyl piperazine. Acid salts of the piperazine base can be alkylated so long as sufficient base is added to the reaction to deprotonate piperazine. In this example, the ethyl bromoacetate is $^{13}C$ labeled. Because both the piperazine and acetic acid reactants comprise heavy atom isotopes, a solid phase base was chosen so that only one equivalent of each reactant was required to produce the product. As was observed with Example 14, hydrolysis of the ethyl ester proceeded by mere heating the compound in an aqueous solution.

In some other embodiments, the N-substituted piperazine acetic acid can be assembled on a solid support. According to the method and with reference to FIG. 14C and Example 16, the halo acetic acid moiety, as a carboxylic acid, can be reached with trityl chloride resin to thereby produce a support bound halo acetic acid. The support bound halo acetic acid can then be treated with the desired N-substituted piperazine (e.g. N-methyl piperazine) under basic conditions to thereby produce the N-substituted piperazine acetic acid. Isotopically enriched N-methyl piperazine and halo acetic acid moieties can be used, including $^{18}O$ labeled compounds although $^{18}O$ labeling can involve special considerations and is discussed in more detail below.

In accordance with the aforementioned discussion, a heavy atom isotope can be incorporated at virtually any position of the N-substituted piperazine acetic acid, including $^{18}O$ incorporation that will be discussed in more detail below. Consequently, the present invention contemplates all possible isotopically enriched N-substituted piperazine acetic acids comprising one or more heavy atom isotopes of the general formula:

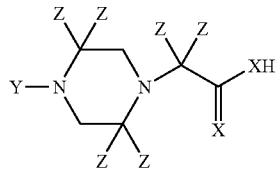

including all possible salt forms and/or hydrate forms thereof.

C. Incorporation of $^{18}O$ into N-Substituted Piperazine Acetic Acids

In some embodiments, this invention pertains to methods for the incorporation of $^{18}O$ into N-substituted piperazine acetic acids as well as to the $^{18}O$ labeled N-substituted piperazine acetic acids themselves. In some embodiments, incorporation of $^{18}O$ is not substantially different as compared with the methods described for the preparation of isotopically labeled N-substituted piperazine acetic acids in Section B, above. In some other embodiments, incorporation of $^{18}O$ is substantially different and takes advantage of the very caveat that creates some concern about the methods previously discussed.

The caveat with respect to the preparation of $^{18}O$ labeled N-substituted piperazine acetic acids lies with the exchange of $^{18}O \Leftrightarrow ^{16}O$ that can occur between unlabeled water ($H_2{}^{16}O$) and the $^{18}O$ of a heavy carboxylic acid group. A carboxylic acid group is inherently acidic. Acid can catalyze the exchange of the oxygen atoms of a carboxylic acid group and water, such as residual water in a sample or water used in a reaction (e.g. hydrolysis of an ester). Consequently, whenever $^{18}O$ labeled N-substituted piperazine acetic acids were desired, one of two different synthetic routes was chosen.

In some embodiments, the $^{18}O$ labeled N-substituted piperazine acetic acid was obtained by alkylation with an appropriately $^{18}O$ labeled halo acetic acid moiety. The procedure is essentially as outlined in Section B, above except that an acid labile ester of the halo acetic acid was used in the alkylation reaction. In some embodiments, the halo acetic acid moiety comprised the formula:

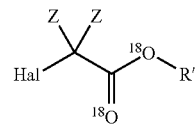

wherein Hal is previously defined and R' is an acid labile ester group, including but not limited to tert-butyldimethylsilyl or t-boc.

Figure 15A:
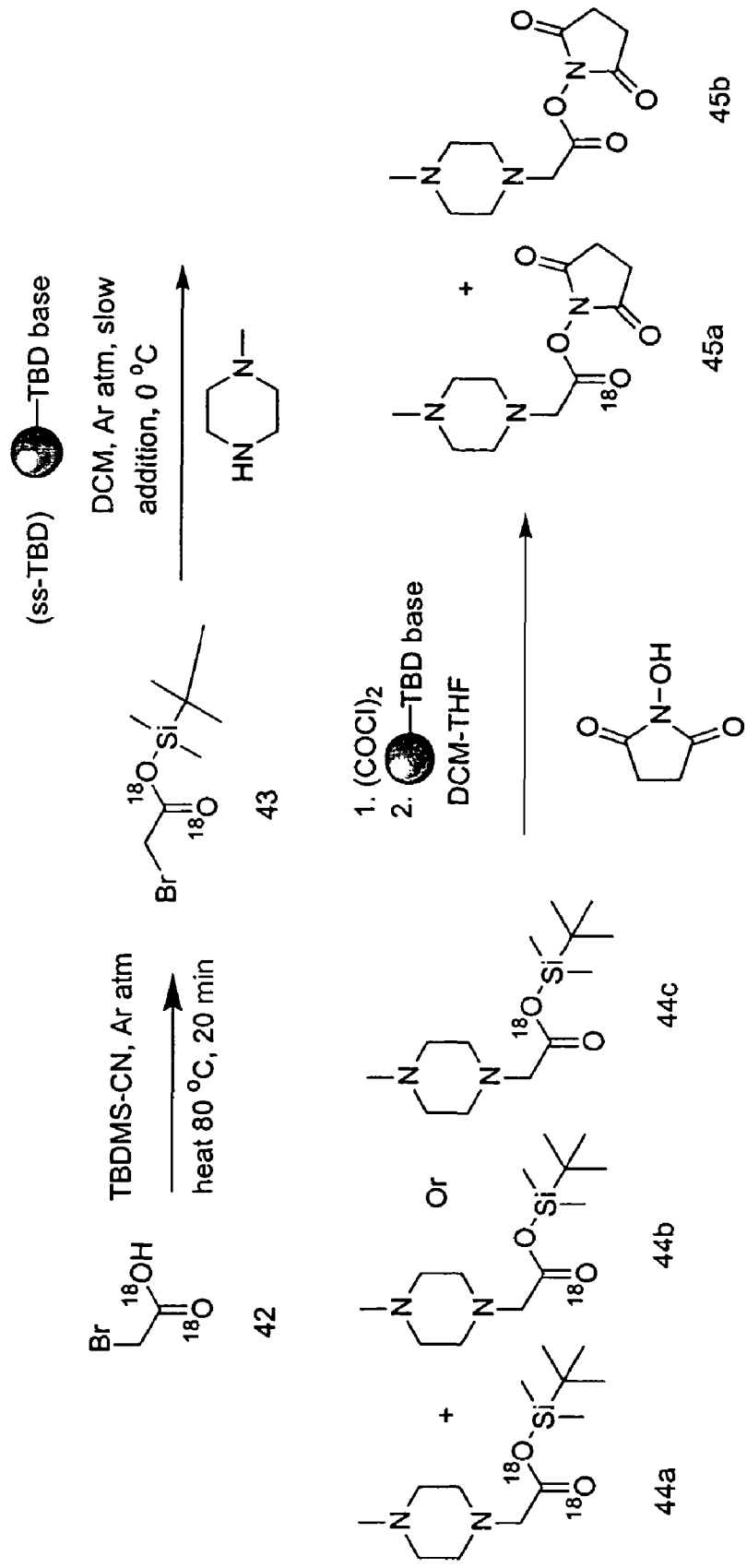
FIG. 15A is an illustration of a synthetic scheme for the synthesis of $^{18}O$ labeled N-methyl piperazine acetic acids.

With reference to FIG. 15A and Example 17, the tert-butyldimethylsilyl (TBDMS) ester of $(^{18}O)_2$ bromoacetic acid (43) was used in the alkylation reaction. This ester was prepared using $^{18}O$ labeled bromoacetic acid (42), obtained as a custom order from Cambridge Isotope Laboratory, Inc., and TBDMS-CN. The TBDMS ester of N-methyl piperazine acetic acid (44a, 44b & 44c) was the product of the alkylation with N-methyl piperazine. The TBDMS ester was selected so that it could be converted to the acid chloride with, for example, oxalyl chloride thereby avoiding the requirement for any water and the possible exchange of $^{18}O$ with $^{16}O$. In the presence of solid phase base (ss-TBD) and N-hydroxysuccinimide (NHS), the acid chloride was converted to the NHS ester (45a & 45b). If the carboxylic acid is desired, instead of the active ester, the TBDMS ester could be converted to the carboxylic acid by treatment with an anhydrous acid such as TFA. Accordingly, aqueous treatment that might lead to $^{18}O \Leftrightarrow ^{16}O$ exchange, can be avoided whether the active ester or the carboxylic acid is desired.

Figure 15B:
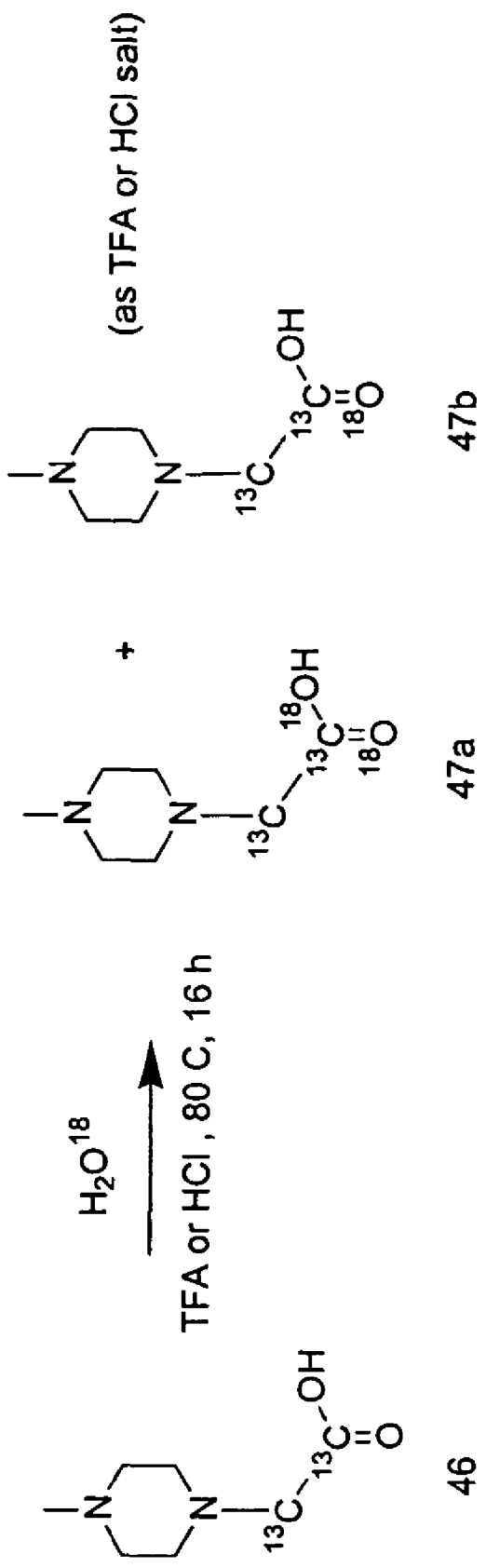
FIG. 15B is an illustration of another synthetic scheme for the synthesis of $^{18}O$ labeled N-methyl piperazine acetic acids.

In some other embodiments, the alkylation to produce N-substituted piperazine acetic acid proceeded as described in Section B, above and the $^{18}O$ was later incorporated. With reference to FIG. 15B and Example 18, it was found that $^{18}O$ could be incorporated into the carboxylic acid group of any N-substituted piperazine acetic acid by treatment of the N-substituted piperazine acetic acid with $H_2{}^{18}O$ under acidic conditions. For example and with reference to FIG. 15B, an isotopically enriched N-methyl piperazine acetic acid (46) lacking $^{18}O$, used to produce the 114 labeling reagent, was treated with $H_2{}^{18}O$ and either HCl or TFA to thereby produce the TFA or HCl salt of the $^{18}O$ isotopically enriched N-methyl piperazine acetic acid (47a) and (47b). Also contemplated are isotopically enriched compounds, whether or not a salt form, existing in hydrate form (i.e. one or more complexed heavy or light water molecules).

Furthermore, the isotopic purity of the product could be increased by repeated cycles of treatment with $H_2{}^{18}O$ under acidic conditions. The higher the state of enrichment of the $H_2{}^{18}O$, the fewer cycles required to produce highly $^{18}O$ enriched N-substituted piperazine acetic acid. When $H_2{}^{18}O$ of 99% purity was used, the isotopic enrichment of N-substituted piperazine acetic acid was typically 96% after two cycles. One or more additional cycles can be performed to further increase the $^{18}O$ isotopic content of the product N-substituted piperazine acetic acids. Because this exchange was performed under acidic conditions, the product was easily isolated as the bis-acid salt of N-substituted piperazine acetic acid (e.g. the bis-TFA or bis-HCl salt). Also contemplated are isotopically enriched compounds, whether or not a salt form, existing in hydrate form (i.e. one or more complexed heavy or light water molecules).

Consequently, the present invention contemplates all possible isotopically enriched N-substituted piperazine acetic acids comprising one or more heavy atom isotopes of the general formula:

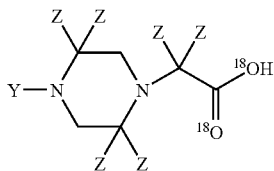

including all possible salt forms and/or hydrate forms thereof.

D. Preparation of Various Active Esters of N-Substituted Piperazine Acetic Acid

In some embodiments, this invention pertains to methods for the preparation of active esters of N-substituted piperazine acetic acid, including isotopically enriched versions thereof, as well as the N-substituted piperazine acetic acid esters themselves, and isotopically enriched versions thereof. The active ester can be any active ester. In some embodiments, the active ester can be formed using an alcohol or thiol of the following formula:

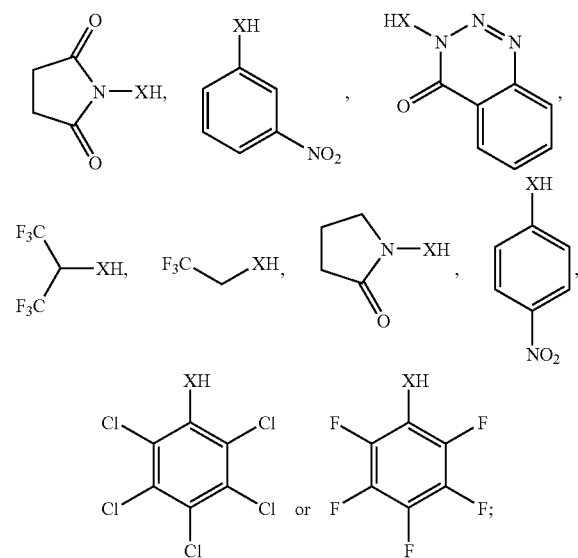

wherein X is O or S, but preferably O. In some other embodiments, the active ester can be formed using an alcohol or thiol of the following formula:

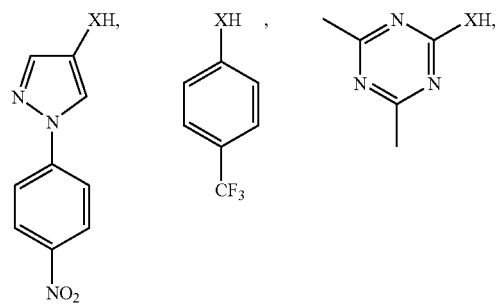

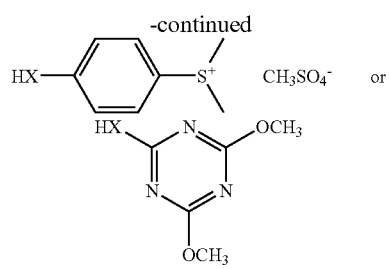

wherein X is O or S, but preferably O.

In some embodiments, the active ester can be prepared through an intermediary imidazolide. According to this method, an N-substituted piperazine acetic acid ester, including isotopically enriched versions thereof, can be converted to the imidazolide. The imidazolide so prepared can then be reacted with the alcohol of choice to thereby produce the active ester of the selected alcohol.

Figure 16A:
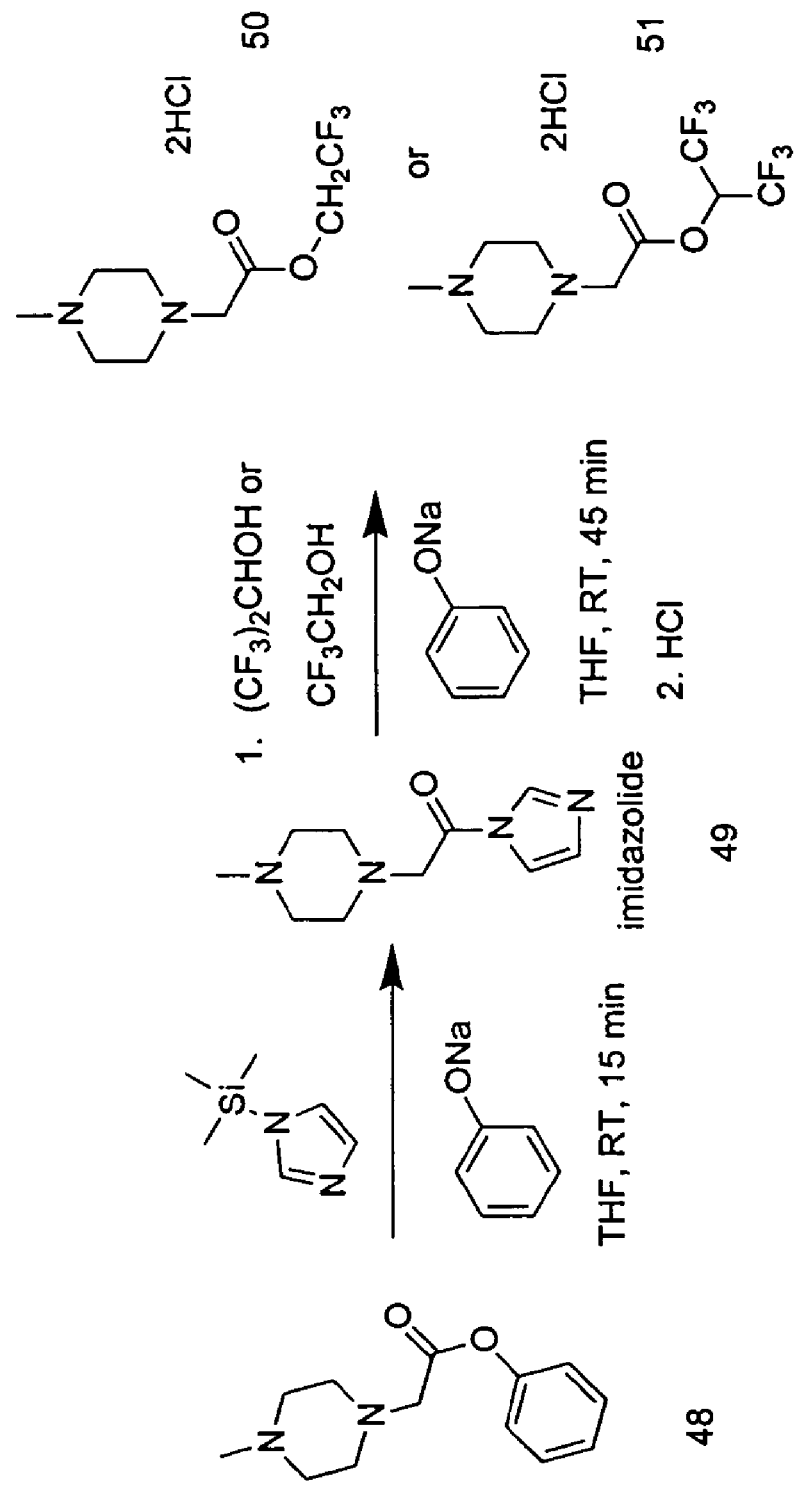
FIG. 16A is an illustration of a synthetic scheme for the synthesis of various active esters of N-methyl piperazine acetic acid.

With reference to FIG. 16A and Example 19, this procedure was used to prepare active esters of 2,2,2-trifluoroethanol and 1,1,1,3,3,3-hexafluoro-2-propanol. According to the figure and the example, the phenyl ester of N-methyl piperazine acetic acid (48) was treated with trimethyl silyl imidizole (TMS-imidizole) and sodium phenoxide to form the imidazolide of N-methyl piperazine acetic acid (49). The imidazolide (49) was then reacted with either 2,2,2-trifluoroethanol or 1,1,1,3,3,3-hexafluoro-2-propanol (HFI—OH) to produce the desired active ester of N-methyl piperazine acetic acid (50) or (51), respectively as a bis-acid salt.

In some other embodiments, the active ester can be prepared by conversion of the N-substituted piperazine acetic acid, including isotopically enriched versions thereof, to an acid chloride followed by subsequent reaction of the acid chloride with the alcohol of choice to thereby produce the active ester of the selected alcohol.

Figure 16B:
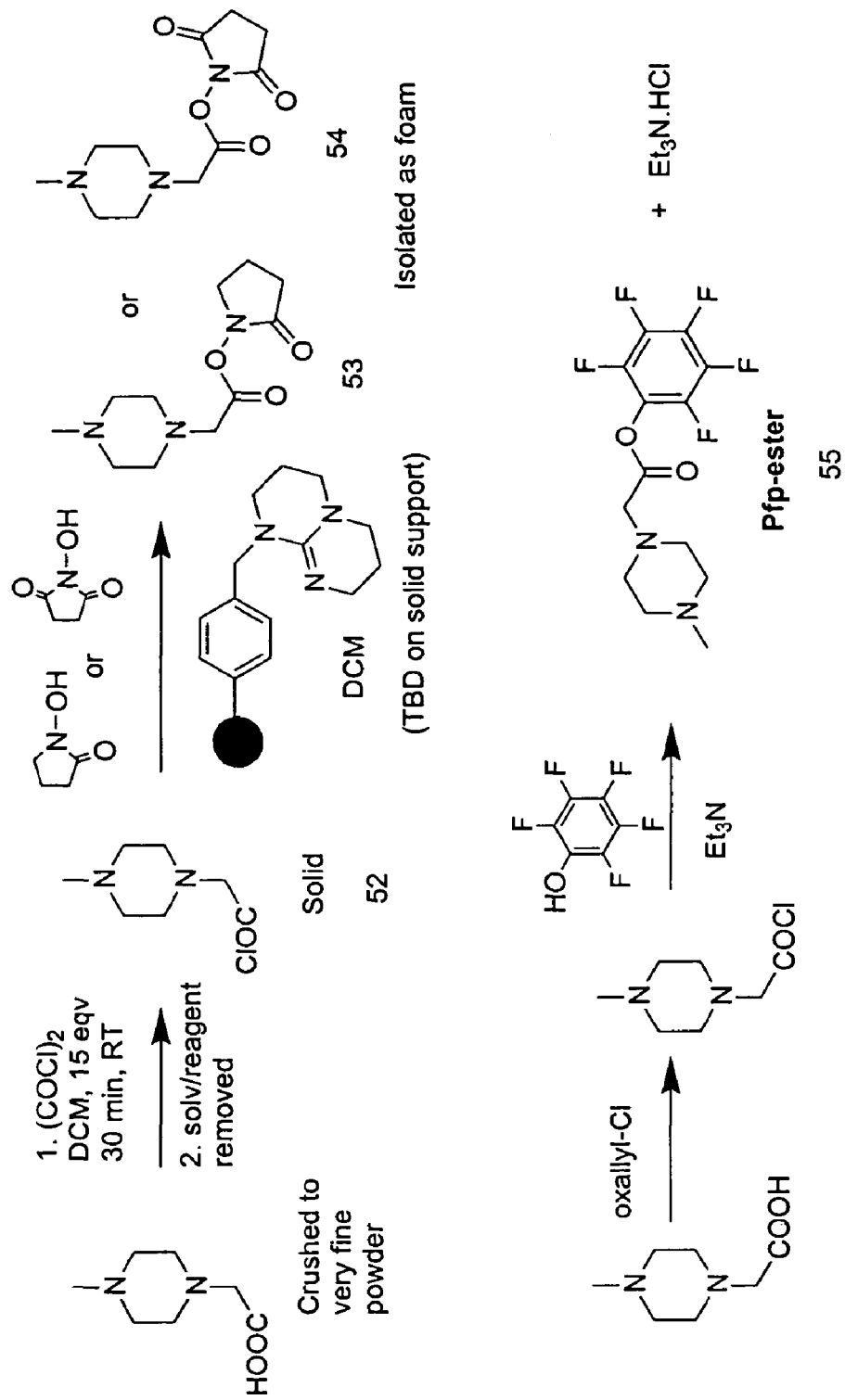
FIG. 16B is an illustration of another synthetic scheme for the synthesis of various active esters of N-methyl piperazine acetic acid.

With reference to FIG. 16B and Example 20, the preparation of the NHS and NHP esters of N-methyl piperazine acetic acid are illustrated using this general procedure. According to the figure and the example, N-methyl piperazine acetic acid is treated with oxalyl chloride to produce the acid chloride (52). The acid chloride is then treated with either of NHP or NHS and solid phase base to thereby produce the active ester (53) or (54), respectively as the free piperazine base (not as an acid salt).

FIG. 16B also illustrates the application of oxalyl chloride to the production of the pentafluorophenyl (Pfp) ester (55) wherein a solution phase base (e.g. triethylamine) is used. The reaction proceeded well with the solution phase base but the hydrochloride salt of the base proved difficult to remove. Application of the solid phase base avoids this caveat.

In still some other embodiments, the active ester can be prepared by treatment of the N-substituted piperazine acetic acid, including isotopically enriched versions thereof, with a trihalooacetate ester of the alcohol that is desired to form the active ester of the N-substituted piperazine acetic acid. In this context, halo refers to fluorine, chlorine, bromine and iodine but preferably to fluorine and chlorine. The trihalooacetate ester has the general formula:

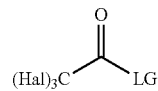

wherein Hal refers to a halogen (fluorine, chlorine, bromine or iodine) and LG refers to the leaving group alcohol. The leaving group (LG) of the trihaloacetate esters can have the following general formula:

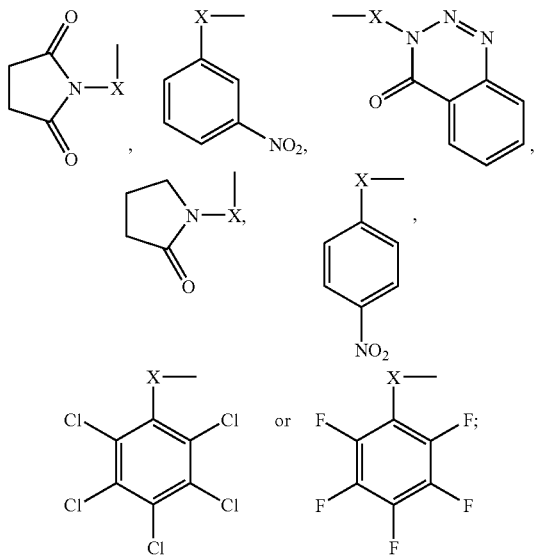

wherein X is O or S, but preferably O. Active esters of N-methyl piperazine acetic acid comprising these leaving groups (LG) were successfully prepared using the identified trifluoroacetate esters (where X is O).

This procedure can be applied to the N-substituted piperazine acetic acids whether they are the acid salt or the zwitterion form. The N-substituted piperazine acetic acids can be reacted with the triholoacetate ester of the alcohol to thereby produce the active ester of the N-substituted piperazine acetic acid. A base that can deprotonate the basic nitrogen atoms of piperazine ring can be added to the reaction as need to induce formation of the product when the starting material is an acid salt of N-substituted piperazine acetic acid. The active ester of the N-substituted piperazine acetic acid can itself be isolated as the mono-acid salt or the di-acid salt. (e.g. the mono-TFA salt, the mono HCl salt, the bis-TFA salt or the bis-HCl salt). Also contemplated are isotopically enriched active ester compounds, whether or not a salt form, existing in hydrate form (i.e. one or more complexed heavy or light water molecules). When the trihaloacetate ester is reacted with an N-substituted piperazine acetic acid the product can be:

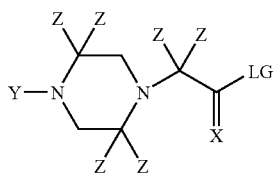

or a salt form and/or hydrate form thereof, wherein X, Y and Z are previously defined. The group LG is the leaving group of the active ester that is displaced by the reactive group of an analyte to be labeled; in essence the leaving group is the alcohol used to form the active ester.

Certain trihaloacetate esters are commercially available. For example, the trifluoracetate esters of pentafluorphenol and 4-nitrophenol can be purchased from commercial sources. However, the others can be obtained by reacting the desired alcohol with trihaloacetic anhydride. With reference to Table 2, below, the trifluoroacetate esters of pentachlorophenol (Pcp), 3-hydroxy-1,2,3-benzotriazine-4(3H)-one (Dhbt), NHS, 3-nitrophenol (3-NP) and N-hydroxypyrrolidinone (NHP) were prepared by reacting the respective alcohol with trifluoracetic anhydride. The general procedure for such reactions can be found in Example 21. Other alcohols that can be used to produce trihaloacetate esters suitable for the formation of other active esters can also be used.

Figure 16C:
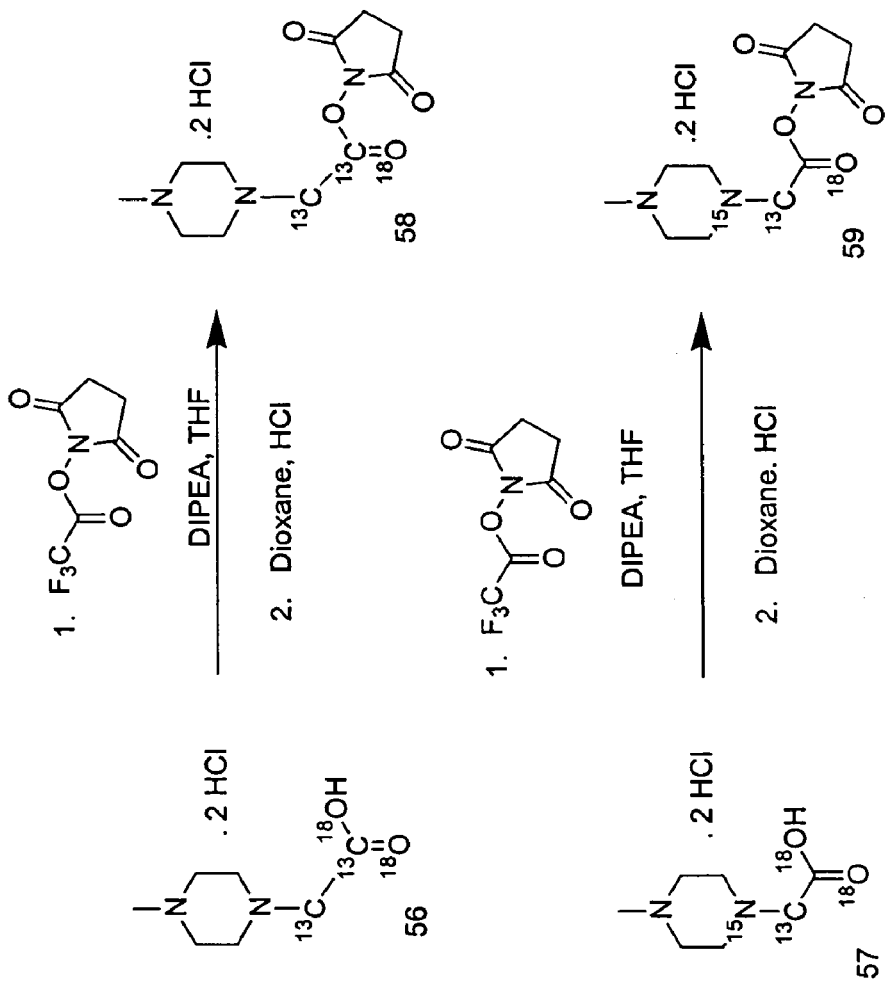
FIG. 16C is an illustration of yet another synthetic scheme for the synthesis of various active esters of N-methyl piperazine acetic acid.

FIG. 16C illustrates the production of the 114 and 115 labeling reagents as the NHS ester. Accordingly, the procedure was successfully applied to the production of isotopically enriched active esters of N-substituted piperazine acetic acids. These active ester reagents were produced as the bis-HCl salts from the bis-HCl salts of the piperazine base.

Figure 16D:
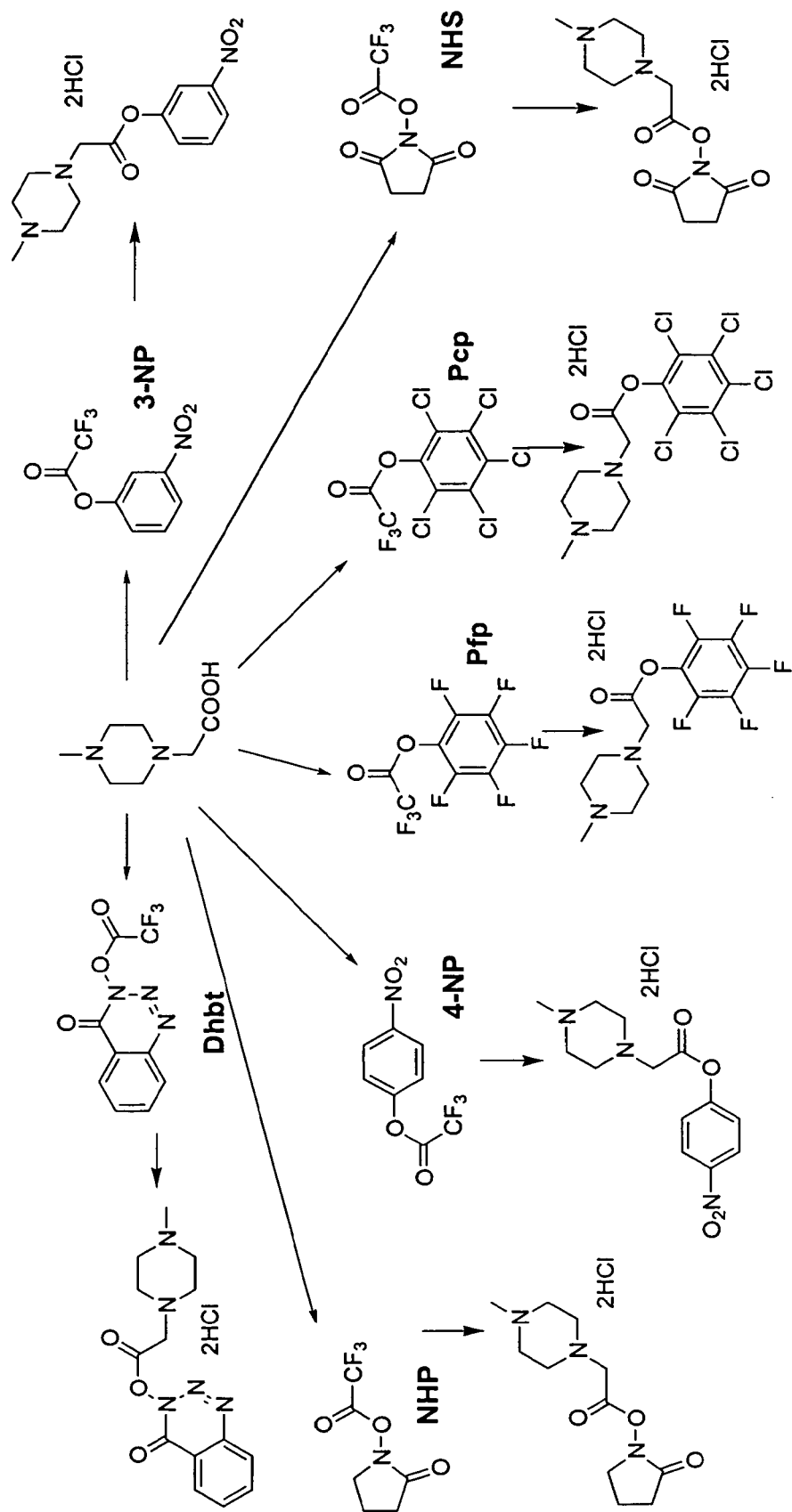
FIG. 16D is an illustration of still another synthetic scheme for the synthesis of various active esters of N-methyl piperazine acetic acid.

FIG. 16D illustrates the production of numerous other active esters of N-methyl piperazine acetic acid that were produced using this generic process. As will be appreciated by the ordinary practitioner, this procedure is generic and robust and can be applied to the production of numerous other active esters of a plethora of N-substituted piperazine acetic acid derivatives.

Figure 17A:
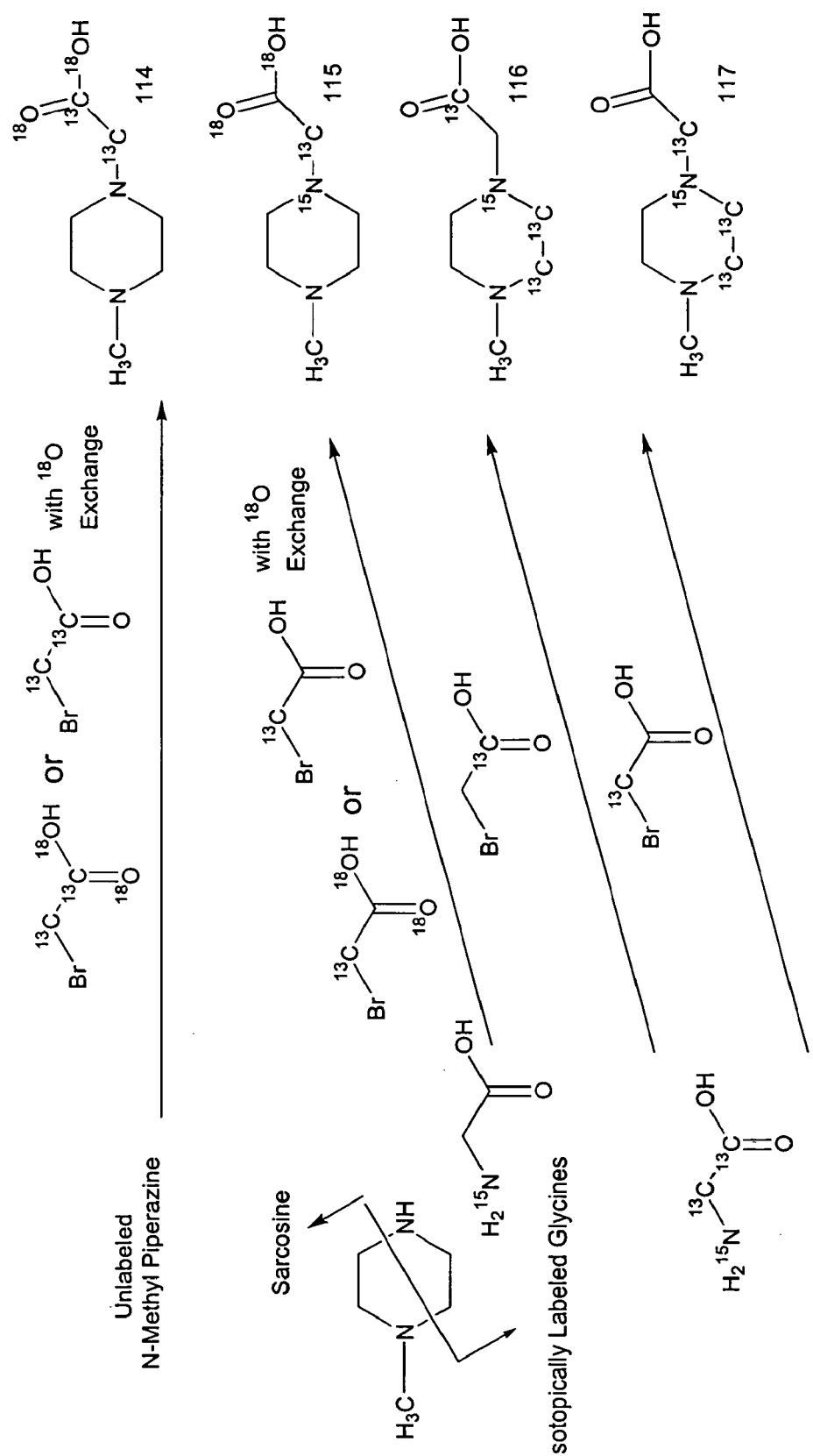
FIG. 17A is an illustration of the heavy atom isotope incorporation pathway for the preparation of four isobaric N-methyl piperazine acetic acids.
Figure 17B:
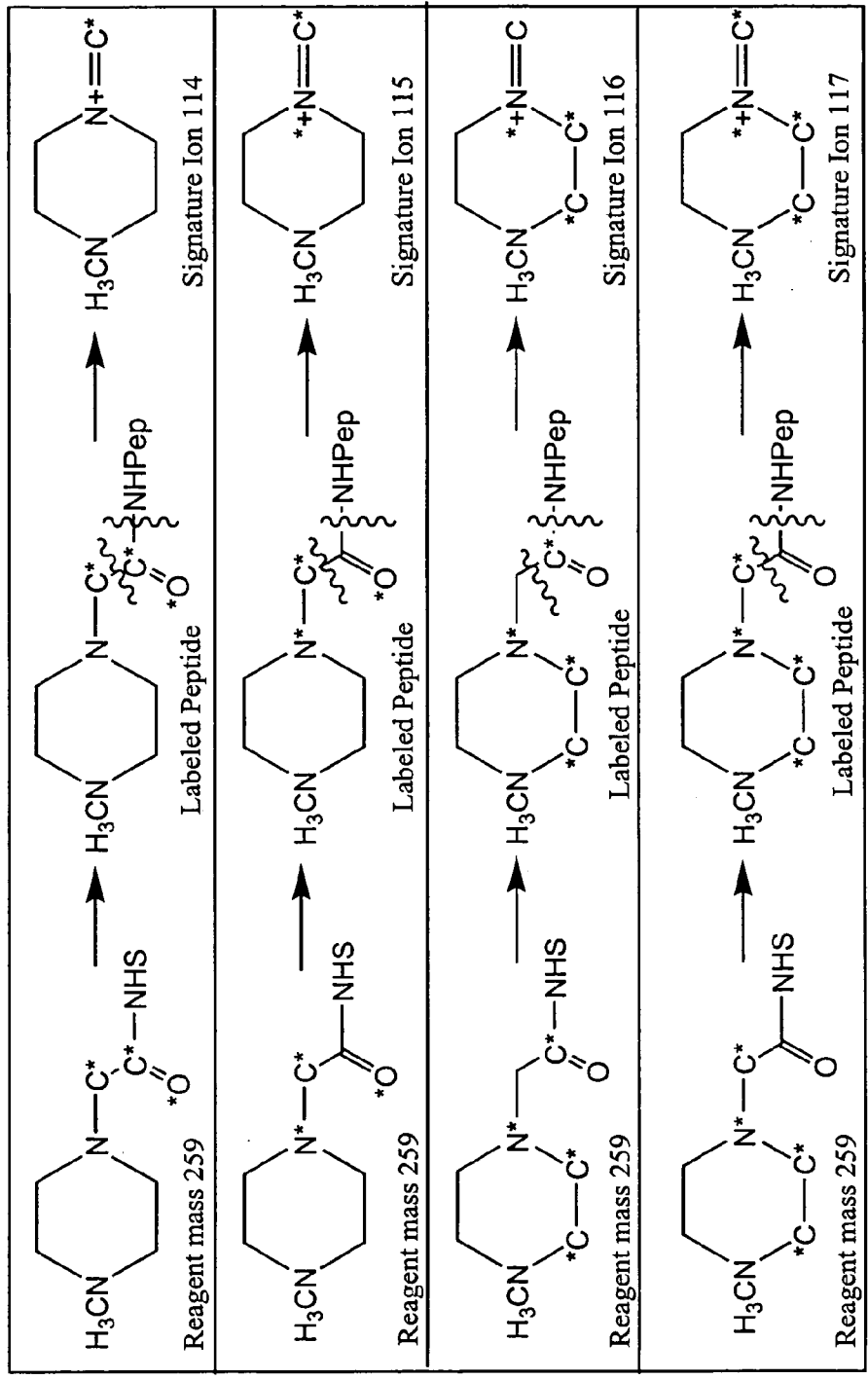
FIG. 17B is an illustration of the labeling and fragmentation of peptides using four isobaric N-methyl piperazine acetic acid active ester labeling reagents.

E. Isotope Incorporation Pathway for the Preparation of a Set of Isobaric Labeling Reagents FIG. 17A illustrates the general pathway taken to the production of a set of four isobaric labeling reagents identified as 114, 115, 116 and 117. These designations are based upon the "signature ion" each reagent produces upon fragmentation in a mass spectrometer (FIG. 17B). The "signature ion" can be used to deconvolute information associated with different samples in a multiplex assay.

The pathways illustrated in FIG. 17A utilize the procedures set forth above for the production of N-substituted piperazine acetic acids, and active esters thereof. In particular, suitable isotopically labeled glycines were used in the preparation of suitable isotopically labeled N-substituted piperazines (i.e. N-methyl piperazines). The labeled and unlabeled N-methyl piperazines can be treated with isotopically labeled bromoacetic acid derivatives, with or without subsequent $^{18}O$ enrichment, to thereby produce the N-methyl piperazine acetic acid compounds of desired structure. These suitably labeled N-methyl piperazine acetic acid compounds were used as labeling reagents; in the present case by conversion to an active ester (e.g. NHS ester) for coupling with analytes such as peptides.

FIG. 17 illustrates different possible structures for the reporter fragment ions of the 114, 115, 116 and 117 labeling reagents.

F. State of Isotopic Enrichment

The various N-substituted piperazines, N-substituted piperazine acetic acids and active esters of N-substituted piperazine acetic acid can be prepared with starting materials of greater than 80 percent isotopic purity for each heavy atom isotope. The isotopic purity can be greater than 93 percent for each heavy atom isotope in some starting materials. In other starting materials the isotopic purity can be greater than 96 percent for each heavy atom isotope. In still other starting materials the isotopic purity can be greater than 98 percent for each heavy atom isotope. When performing an $^{16}O$ to $^{18}O$ exchange, it was possible to routinely obtain carboxylic acid groups of 96 or greater percent isotopic purity (per oxygen atom) of the heavy atom isotope.

With the exception of $^{18}O$, which can be exchanged with $^{16}O$ in certain cases, the isotope purity and composition of starting materials will generally translate directly into the isotopic purity of the products. Moreover, for $^{18}O$, it has been shown that isotopic purity of greater than 96 percent (per atom) can be achieved using the methods described herein. Accordingly, in some embodiments, this invention pertains to N-substituted piperazines, N-substituted piperazine acetic acids and/or active esters of N-substituted piperazine acetic acid having an isotopic purity of at least 80 percent for each heavy atom isotope. In some other embodiments, this invention pertains to N-substituted piperazines, N-substituted piperazine acetic acids and/or active esters of N-substituted piperazine acetic acid having an isotopic purity of at least 93 percent for each heavy atom isotope. In still some other embodiments, this invention pertains to N-substituted piperazines, N-substituted piperazine acetic acids and/or active esters of N-substituted piperazine acetic acid having an isotopic purity of at least 96 percent for each heavy atom isotope. In yet some other embodiments, this invention pertains to N-substituted piperazines, N-substituted piperazine acetic acids and/or active esters of N-substituted piperazine acetic acid having an isotopic purity of at least 98 percent for each heavy atom isotope.

G. Labeling of Analytes with Active Esters of N-substituted Piperazine Acetic Acids:

Generally, active esters of N-substituted piperazine acetic acid are electrophilic and can be reacted with nucleophilic groups of the analyte to thereby produce labeled analytes. In some embodiments, the labeling reagent can be support bound. Active esters can react with thiol groups, and to a lesser extent with hydroxyl groups. However, active esters are particularly well suited for reaction with amine groups.

The active esters of N-substituted piperazine acetic acid can be reacted with an analyte in solution to thereby produce a labeled analyte. The solution used to effect labeling can be selected depending upon the nature of the analyte and the labeling reagent. Conditions can be selected such that the labeling reagent and/or the analyte are soluble, or at least partially soluble. Because analytes can be biomolecules, the labeling conditions can be selected to be aqueous. Aqueous conditions can include organic modifiers that increase the solubility of the labeling reagent and/or analyte. Organic modifiers can be water miscible and can include, but are not limited to, alcohols (such as methanol, ethanol, n-propanol, iso-propanol or n-butanol or t-butanol) ethers (such as tetrahydrofuran or dioxane) acetonitrile (ACN), N,N-dimethylformamide (DMF), N-Methyl pyrrolidine (NMP), and the like. The reactions can be performed under conditions of preferred ionic strength and/or pH.

Generally, the pH of aqueous solutions can be modulated with a buffer. The pH can be adjusted to be within the range of 4-10. The pH can be adjusted to be outside of this range. The basicity of non-aqueous reactions can be modulated by the addition of non-nucleophilic organic bases. Non-limiting examples of suitable bases include N-methylmorpholine (NMM), triethylamine ($Et_3N$) and N,N-diisopropylethylamine (DIPEA). Alternatively, the pH can be modulated using biological buffers such as (N-[2-hydroxyethyl)piperazine-N'-[2-ethanesulfonic acid) (HEPES) or 4-morpholineethane-sulfonic acid (MES). Inorganic buffers such as sodium bicarbonate or sodium carbonate can also be used to control pH. Non-nucleophilic buffers can be used so that the buffers do not react with the labeling reagent.

All four of the isobaric labeling reagents of N-methylpiperazine acetic acid (114, 115, 116 and 117; See FIG. 17A) were produced as NHS esters. These reagents comprise an exemplary set of isobaric labeling reagents. Two or more of the reagents were used to label peptides, including peptides (analytes) obtained from digested protein (See: Examples 24 & 26). The set of reagents (two or more of them), were shown to be suitable for the multiplex analysis, including proteome analysis of yeast using the general procedures as described herein.

Because the reagents are the labeling reagents are non-polymeric, low molecular weight isobaric compounds, there is no significant signal splitting in either the MS or MS/MS modes that might otherwise complicate the spectra.

H. General Properties of the NMPAA Isobaric Labeling Reagents when Fragmented

Figure 17C:
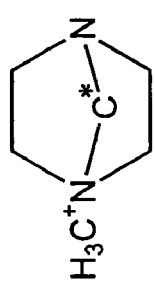
FIG. 17C is an illustration of two possible structures for each of the signature ions produced from the isobaric set of reagents illustrated in FIG. 17B.
Figure 17C:
Figure 17C:
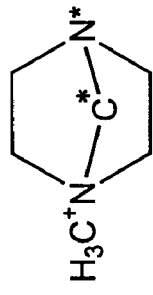
Figure 17C:
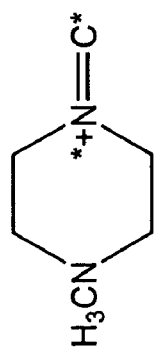
Figure 17C:
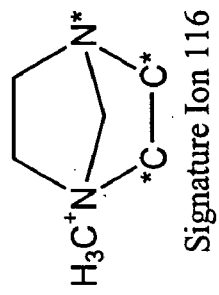
Figure 17C:
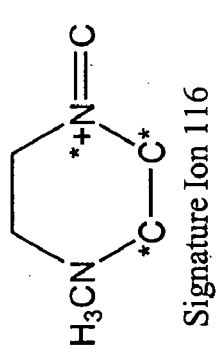
Figure 17C:
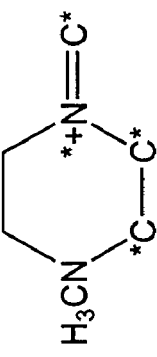

FIG. 17C is an illustration of two possible structures for the signature ions of the 114, 115, 116 and 117 labeling reagents. Because there are alternative chemical structures that might be correct, reference is made to the molecular formulas of the signature ions. The molecular formula of the light signature ion is $C_6H_{13}N_2^+$. The molecular formulas of the isotopically enriched 114, 115, 116 and 117 signature ions respectively are: $^{13}CC_5H_{13}N_2^+$, $^{13}CC_5H_{13}^{15}NN^+$, $^{13}C_2C_4H_{13}^{15}NN^+$ and $^{13}C_3C_3H_{13}^{15}NN^+$.

Figure 18:
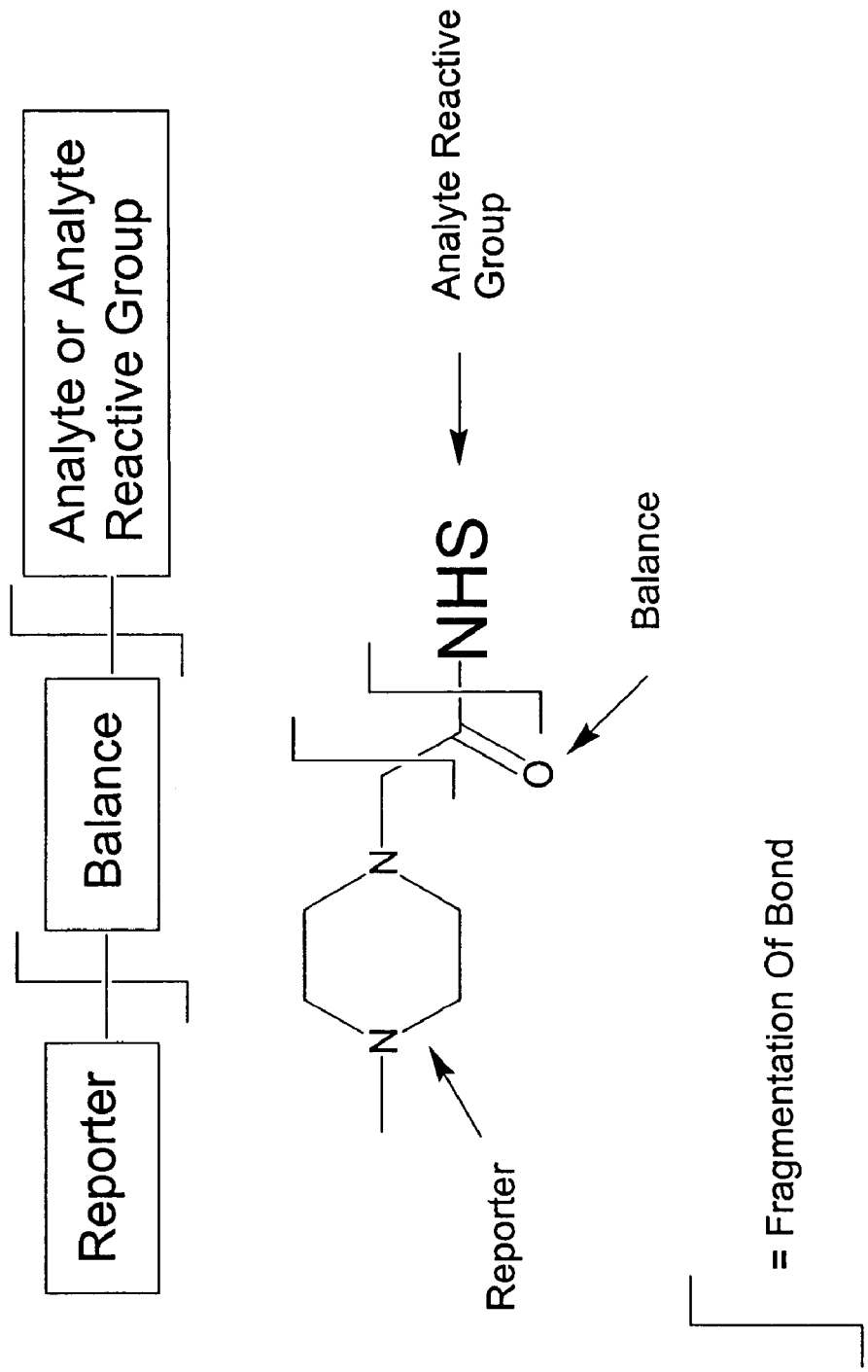
FIG. 18 is an illustration of general properties of isobaric labeling reagents, including an example of an N-methyl piperazine acetic acid moiety containing isobaric labeling reagent.
Figure 19A:
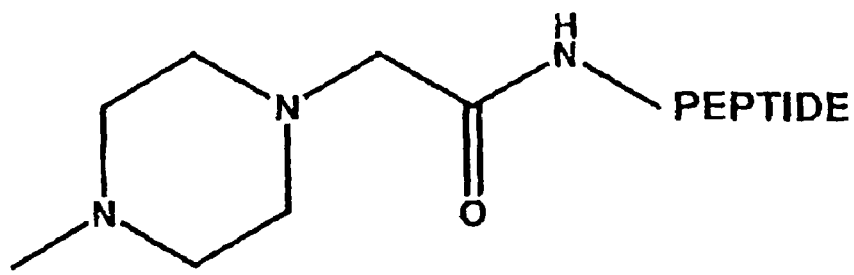
FIG. 19A is an illustration of a peptide analyte labeled with N-methyl piperazine acetic acid.
Figure 19B:
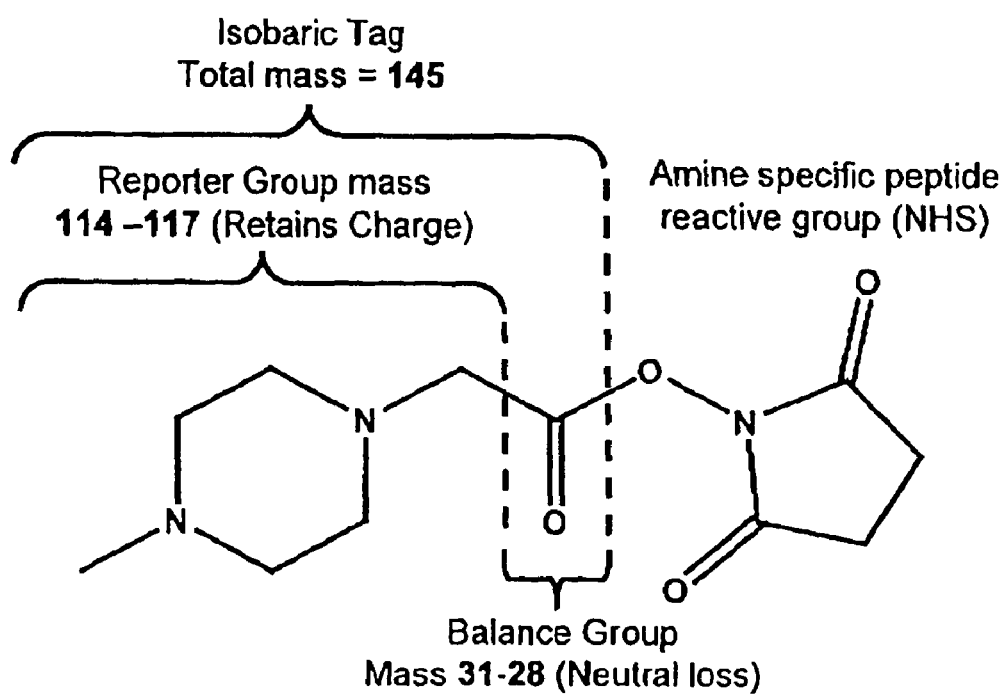
FIG. 19B is an illustration of how the N-methyl piperazine acetic acid moiety comprises a reporter and balance moiety.

With reference to FIGS. 18 & 19, the general properties of the isobaric labeling reagents when fragmented are illustrated. The isobaric labeling reagents can be considered to comprise a reporter, a balance and an analyte reactive group. Once the analyte has been labeled, the analyte can be linked directly to the balance.

As illustrated, there is a bond that links the reporter to the balance and a bond that links the balance to the analyte (or the analyte reactive group). When subjected to dissociative energy levels these bonds can be fragmented. In some embodiments, fragmentation of one of the bonds will result in fragmentation of the other bond. In this way, little or no partially labeled analyte is observed in the MS/MS spectrum. This results in a cleaner spectrum. When the label is fragmented, the reporter will produce the signature ion and the balance can be selected to result in a neutral loss or it can also produce a fragment ion. If the balance results in neutral loss (uncharged fragment) the fragment is not observed in the MS/MS spectrum. This results in a cleaner spectrum.

Figure 19C:
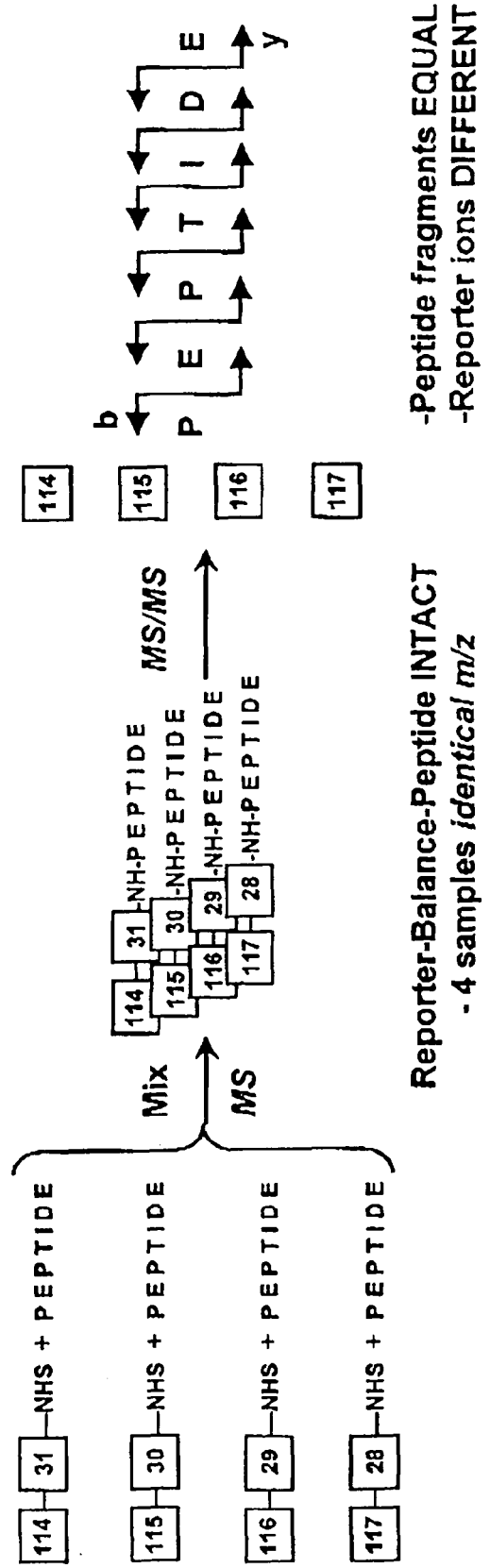
FIG. 19C is an illustration of how the peptides are labeled with different isobaric labeling reagents, mixed, analysed by a first MS analysis and then a second MS (MS/MS) analysis whereby the reporters and daughter ion fragments of the labeled peptides are generated.

As illustrated in FIG. 18, each of the reagents of the isobaric set of N-methyl piperazine labeling reagents comprises a reporter, a balance and an analyte reactive group. The bond fragmentation pattern for the reagents is illustrated in FIG. 19C. These reagents have been determined to exhibit favorable fragmentation characteristics. Specifically, they tend to produce very little observed partially labeled analyte. Furthermore, the carbonyl balance group appears to predominately fragment by neutral loss. Moreover, because the reporter of the label comprises two basic nitrogen groups, it produces strong ion signals for both the signature ions and the labeled analytes in the mass spectrometer.

FIG. 19C illustrates the process whereby a peptide from four different samples can be labeled with each of the different labeling reagents of a set of isobaric labeling reagents (i.e. 114, 115, 116 and 117). The labeled peptides can be mixed to form a sample mixture and analyzed by MS analysis. The four differentially labeled peptides will appear as a single peak in the MS because they all have the same gross mass. After being subjected to dissociative energy, subsequent mass analysis provides the mass of the reporters (signature ions) and the daughter fragment ions of the peptide.

I. Preparation of Sample Mixtures:

Once two or more samples have been differentially labeled with different isobaric labels of a set, a sample mixture can be prepared simply by mixing the samples of labeled analytes. The samples can be of any type. One or more of the samples can be control samples and one or more of the samples can be test samples. Because the unique reporter moiety of each different labeling reagent will produce a unique signature ion under MS/MS conditions, labeled analytes of each sample of the mixture can be related back to the sample from which it originated when the mixture is analyzed.

The sample mixture can be prepared by mixing differing amounts of each sample. The sample mixture can be prepared by mixing equal amounts of each of the samples. In this way there can be a direct comparison of the amount of each analyte (analyte by analyte) in each of the samples based upon the intensity of the peaks for the signature ions observed in the mass spectrometer. Whether or not equal amounts of sample are mixed together, the amount of each sample used to produce the sample mixture can be recorded. If unequal amounts of sample are used to prepare the sample mixture, appropriate ratios can be calculated from this information so that the relative and/or absolute amount (often expressed in concentration or quantity) of the analytes in the sample mixture can be determined based upon the intensity of the signature ion peaks.

For example, two or more samples containing digested peptides as the analyte, each sample being labeled with one of the isobaric labeling reagents (114, 115, 116 or 117; See FIG. 17A), can be mixed to form a mixture that can be analyzed in a tandem mass spectrometer. After the first MS analysis, selected ions, of a particular mass representing a mixture of fragment ions of the same analyte labeled with two or more different isobaric labels, can be subjected to dissociative energy causing fragmentation of the selected ions. The selected ions, and the fragments thereof, can then re-analyzed in the mass spectrometer wherein signature ions of the isobaric labeling reagents used to label the analytes, as well as daughter ions of the analyte, can be observed (See FIG. 19C). Relative quantitation of analytes in the samples can be determined. Absolute quantitation is possible if a known amount of the peptide, as a labeled standard, is added to the sample mixture.

The following examples are illustrative of the disclosed compositions and methods, and are not intended to be limit the scope of the invention. Without departing from the spirit and scope of the invention, various changes and modifications of the invention will be clear to one skilled in the art and can be made to adapt the invention to various uses and conditions. Thus, other embodiments are encompassed.

EXAMPLES

A: Synthesis of Morpholine Derivatives

Example 1

Synthesis of Morpholine Acetic Acid

Bromoacetic acid (2 g, 14.4 mole) was dissolved in tetrahydrofuran (50 mL) and added dropwise to a stirred solution of morpholine (3.76 g, 43.2 mole) in tetrahydrofuran (THF, 20 mL). The solution was stirred at room temperature for three days. The white solid (4.17 g) was filtered, washed with THF (100 mL), and recrystallised from hot ethanol (EtOH), Yield: 2.59 g: IR: 1740 cm-1. For the two different isobaric versions of morpholine acetic acid, either bromoacetic-1-$^{13}$C acid (Aldrich PN 27,933-1) or bromoacetic-2-$^{13}$C acid (Aldrich PN 27,935-8) was substituted for bromoacetic acid.

Example 2

Synthesis of Morpholine Acetic Acid N-Hydroxysuccinimide Ester

Dimethylformamide (dry, 1.75 g, 0.024M) was dissolved in tetrahydrofuran (dry, 30 mLs). This solution was added dropwise to a stirred solution of thionyl chloride (2.85 g, 0.024M) dissolved in tetrahydrofuran (dry, 20 mLs) and cooled in an ice bath. After complete addition and 30 minutes on ice, the ice bath was removed and solid N-hydroxysuccinimide (2 g, 0.017 Moles) was added (which completely dissolved) immediately followed by solid pre-powdered morpholine acetic acid [or -1-$^{13}$C or -2-$^{13}$C morpholine acetic acid] (3.64 g, 0.016M). The morpholine acetic acid dissolved slowly giving a homogeneous solution that rapidly became cloudy. The reaction was left vigorously stirring over night at room temperature. The white solid was washed with tetrahydrofuran and dried under vacuum, weight 3.65 g (67%), IR spectrum 1828.0 cm-1, 1790.0 cm-1, 1736.0 cm-1.

Example 3

Analyte Determination and Relative Quantitation in Two Samples 100 pmole amounts of freeze-dried Glu-Fibrinopeptide B (Sigma) were reacted with 200 µl of freshly-made 2% w/v solutions of either I or II (See: FIG. 1A for structure and Examples 1 & 2 for preparation) in ice-cold 0.5M MOPS buffer (pH 7.8 with NaOH) for 30 minutes on ice. The reaction was terminated by the addition of TFA to 0.5% v/v final concentration. The modified peptides were then mixed in various pre-determined proportions to approximately cover the range 1:10 to 10:1 of the differentially labeled peptides. Each peptide mixture was individually purified by reverse-phase de-salting using a Millipore C18 Zip-Tip. Excess reagent and buffer do not retain on the reverse-phase packings, and were thus efficiently removed prior to MS analysis. The mixtures (0.5 µl) were then spotted onto a MALDI target plate, over-spotted with 0.5 µl of 1% w/v α-cyano cinnamic acid in 50% aqueous acetonitrile and each sample was analyzed using a MALDI source fitted to a QTOF analyzer.

Figure 2:
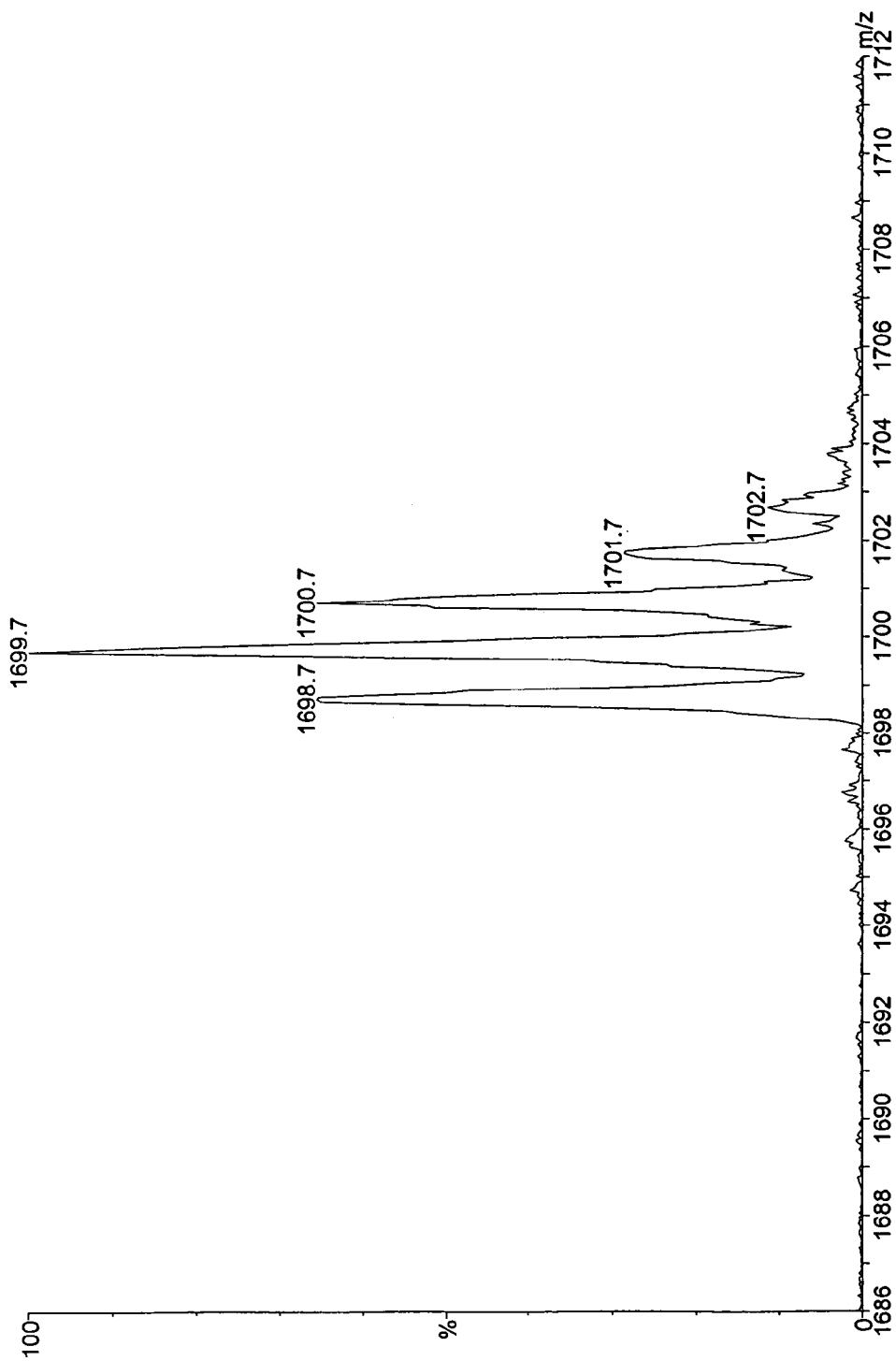
FIG. 2 is an expansion plot of a mass spectrum of a labeled analyte.

FIG. 2 is an expansion plot of the MS spectrum obtained from the 1:1 mix of Glu-fibrinopeptide as modified with reagents I and II. The peak at m/z 1699 represents the N-terminally modified mass of Glu-fibrinopeptide, and as expected, there is no observable difference in m/z of the two different forms of the peptide (See: FIGS. 1A(III) and 1A(IV). The modified peptides are isobaric. The isotopic cluster observed for the peak is exactly as expected for a single species.

Figure 3:
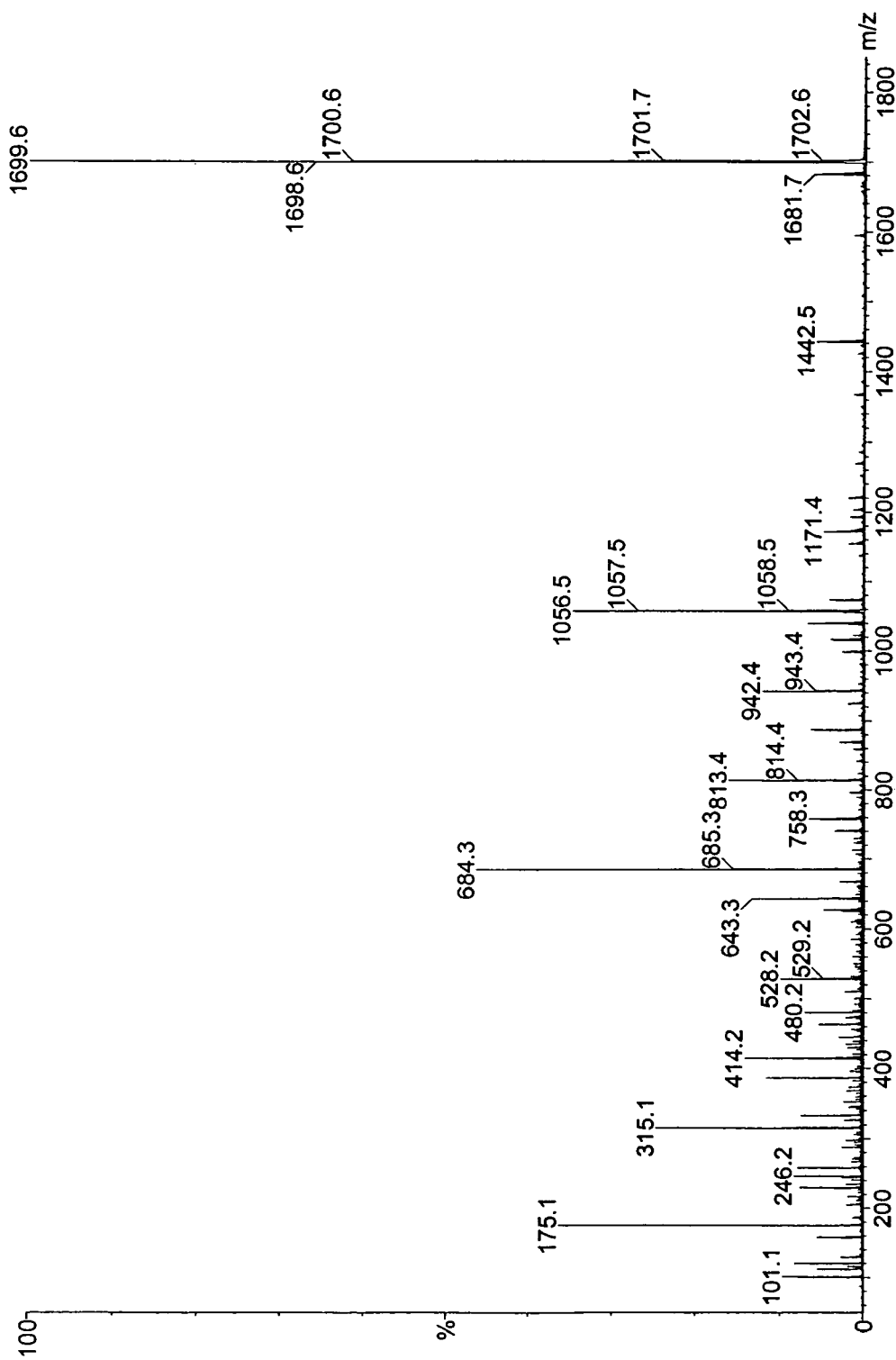
FIG. 3 is the complete mass spectrum obtained from a second mass analysis of the selected labeled analyte identified in the expansion plot of FIG. 2.
Figure 4:
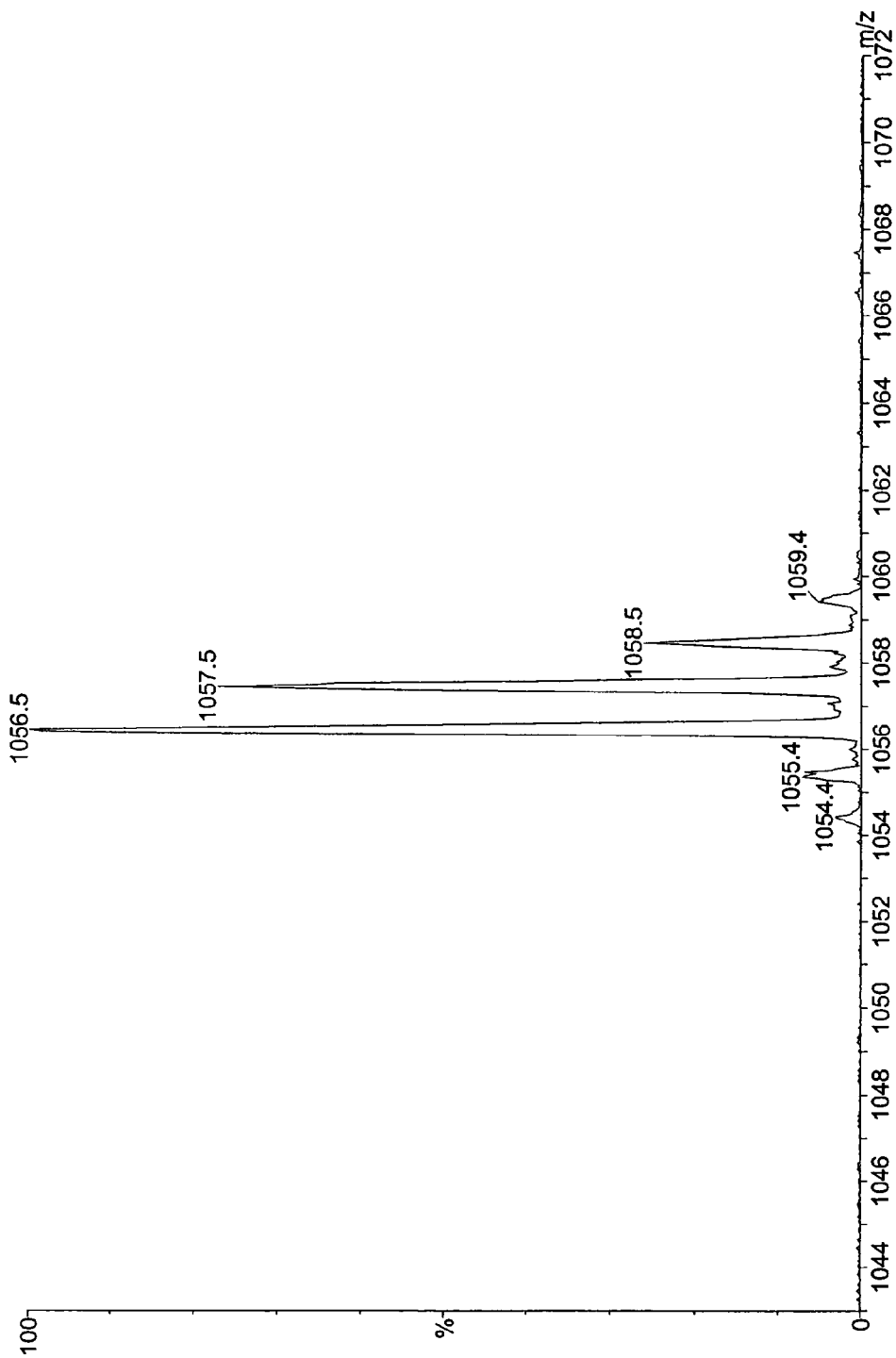
FIG. 4 is an expansion plot of a mass spectrum of the predominate y-ion daughter fragment ion of the analyte as determined in the second mass analysis.
Figure 5:
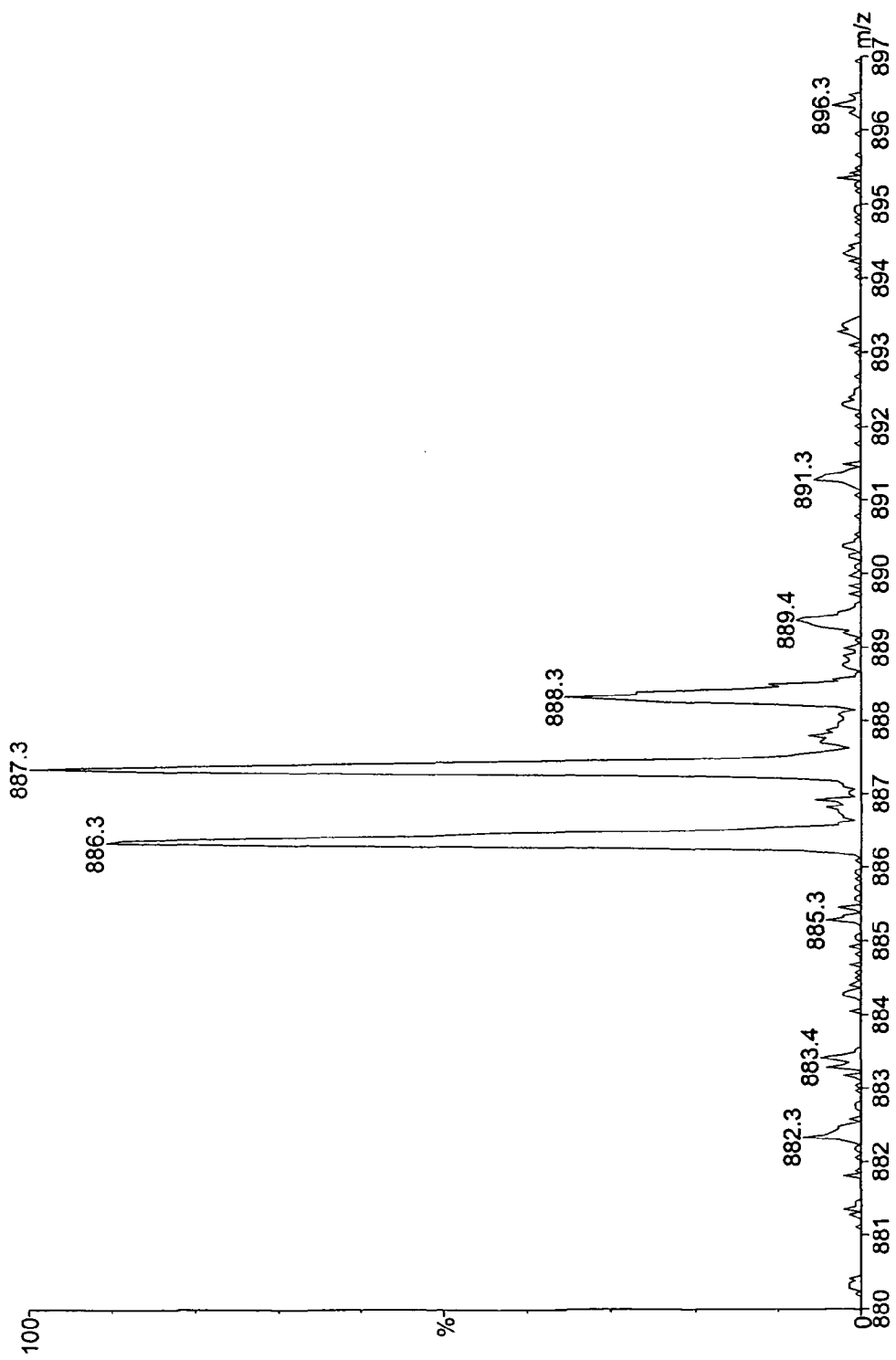
FIG. 5 is an expansion plot of a mass spectrum of the predominate b-ion daughter fragment ion of the analyte as determined in the second mass analysis.

The singly-charged precursor ion of m/z 1699 was then selected for fragmentation by low energy CID (collision offset of approximately −70V), yielding the MS/MS spectrum found in FIG. 3. As expected, the observed ion series was predominantly of types b- and y-. All these ions appeared as single species, with no indication that they comprised a 1:1 mixture of the differentially-labeled peptide species. For example, an expansion of the prominent y-ion at m/z 1056.5 is shown in the expansion plot as FIG. 4 and the prominent b-ion at m/z 886.3 is shown in the expansion plot as FIG. 5.

TABLE 1

| Observed | Predicted |
|---|---|
| 0.13 | 0.125 |
| 0.17 | 0.166 |
| 0.2 | 0.25 |
| 0.46 | 0.5 |
| 1.03 | 1 |
| 2.15 | 2 |

TABLE 1-continued

| Observed | Predicted |
|---|---|
| 4.16 | 4 |
| 6.3 | 6 |
| 7.9 | 8 |

Figure 7:
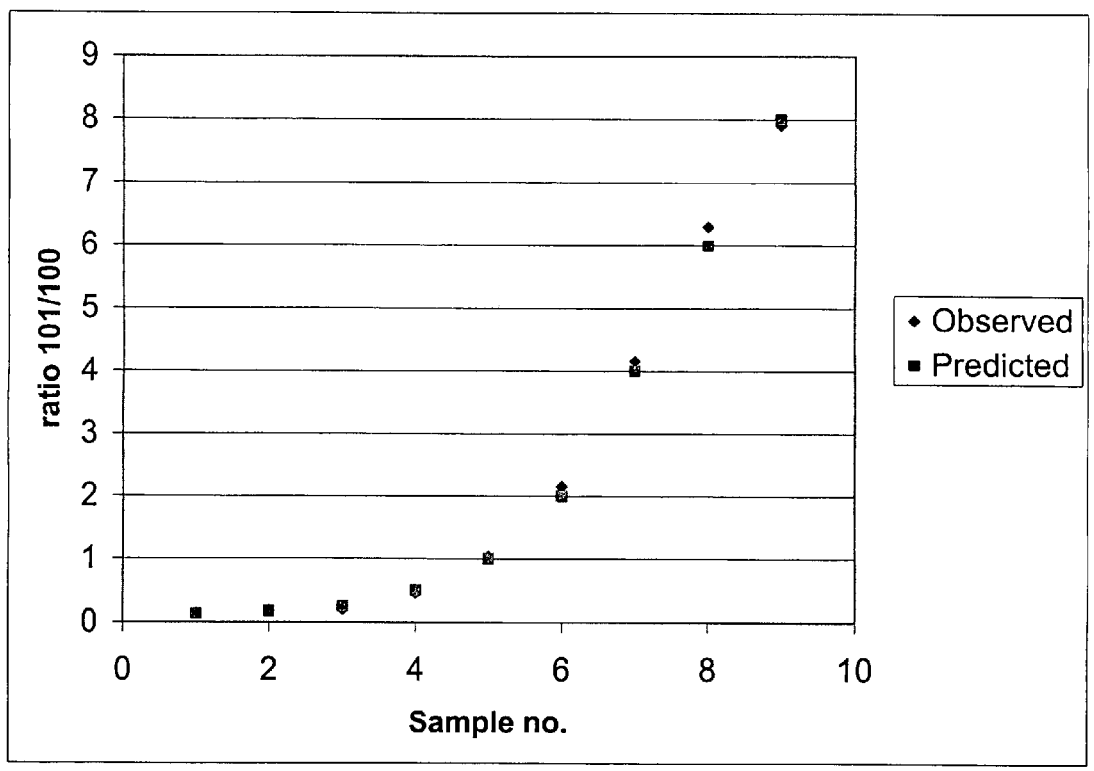
FIG. 7 is a plot of observed vs. predicted ratios of reporters determined by a second mass analysis for various mixtures of a labeled peptide, each peptide of the mixture comprising one of two different reporters.

Close examination of the spectrum at about 100 m/z (FIG. 6), however, reveals the presence of both species VII and VIII (FIG. 1B), which are the fragmentation products of species V and VI (FIG. 1B), respectively. No peaks are observed at m/z 128.1, thereby indicating that species V and VI are not stable enough to be observed. In this example, therefore, it may be that fragmentation of the amide bond between the carbonyl group and the amino-terminal amino acid of the peptide induced subsequent fragmentation of the reporter/linker moiety and loss of the carbonyl moiety as neutral CO. Peak integration was performed using the instrumentation provided with the instrument. Following compensation for the naturally occurring second C-13 isotopic contribution of approximately 6 percent, the measured relative ratio of VIII/VII (101/100) was 1.03 (expected value 1.00). Table 1 shows actual versus observed ratios for additional experimental mixtures prepared (ratio expressed as intensity m/z 101/m/z 100), with correction for the naturally occurring second C-13 contribution. This data is also represented graphically in FIG. 7. There is excellent agreement between observed and predicted values, with mean error <10%.

Example 4

Proteomic Analysis

In practice, a representative proteomic analysis can be performed as follows. Total cellular protein extracts for comparison (e.g. samples A and B) are separately digested with trypsin, or another proteolytic enzyme. The resulting peptide mixtures are separately reacted with, for example, compounds I and II to give complete modification of N-terminal and lysine amines of the peptides. For example, sample A can be reacted with compound I and sample B can be reacted with compound U. Each of the samples containing modified peptides/proteins are then be mixed together before chromatographic separation (typically using multi-dimensional HPLC) and analyzed by MS and MS/MS techniques. The labeling can be performed with a single label/tag treatment (no prior blocking of lysine groups with a second reagent required) as the groups are isobaric.

The mixture of labeled proteins/peptides is then chromatographically separated and the eluent, or fractions thereof, analyzed by mass spectrometry as described in Example 3, above. Effective sensitivity may also be significantly increased using triple-quadrupole or Q-trap mass spectrometers, where the m/z region of 100 and 101 is monitored in precursor-ion mode. The relative ratios of the two "signature" peaks are directly correlated with the ratio of each peptide/protein analyte of interest in each of samples A and B. As used herein, the "signature" peaks are the peaks for the reporter.

Example 5

Analyte Determination and Quantitation Relative to an Internal Standard

Total cellular protein extracts for comparison (e.g. samples A and B) are separately digested with trypsin. The resulting peptide mixtures are separately reacted with X and XI (FIG. 8) to give substantially complete modification of N-terminal and lysine amines as described above. For example, sample A peptides are reacted with X and sample B peptides are reacted with XI. Known amounts or each of samples A and B, containing substantially modified peptides, are then mixed together. To the combined mixture of A and B is now added, in accurately determined amount, a set (one or more) of synthetic peptide(s) that correspond exactly in amino acid sequence and/or post-translational modification (e.g. phosphorylation) to peptide(s) that may be present in the mixture of samples A and B, and where the synthetic peptide(s) are labeled with another member of set of isobaric labeling reagents (e.g. compounds XII or XIII, see: FIG. 8). The combined mixture of peptides from sample A, sample B and synthetic internal standard peptides is now subjected to chromatographic separation, for example by multi-dimensional HPLC, and then analyzed by MS and MS/MS techniques as described previously. All equivalent labeled peptides from sample A, B and synthetic counterparts of identical sequence are isobaric and have substantially identical chromatographic properties. By "substantially identical chromatographic properties" we mean that there is very little, if any, separation of the differentially labeled but otherwise identical peptides. Following MS/MS analysis, the absolute concentration of peptides from sample A and B may be accurately determined by comparison of the relative intensity of the reporters for X (sample A) and for XI (sample B) with respect to the intensity of the reporter (the "signature peak") resulting from the standard peptide labeled with the additional member of the isobaric set (e.g. XII or XIII).

Although the foregoing is a description of two samples (i.e. Samples A and B), this process could be extended in many practical ways. For example, there may be many samples that are analyzed simultaneously provided there is a large enough set of labeling/tagging reagents.

There could be a double (or more where there are more samples to be analyzed) internal standard (e.g. sample A peptides may be 'spiked' with synthetic peptides labeled with reagent XII and sample B peptides may be spiked with synthetic peptides labeled with reagent XIII (of known absolute concentration)). When all are combined, separated and analyzed as described above, Sample A peptides can be quantitated relative to the signature peak for compound XII and sample B peptides can be quantitated relative to the signature peak for compound XIII.

Example 6

Exemplary Synthesis of Piperidine Acetic Acid N-Hydroxysuccinimide Ester

Bromoacetic acid is dissolved in tetrahydrofuran (or another suitable non-nucleophilic solvent) and added dropwise to a stirred solution containing an excess of piperidine in tetrahydrofuran (THF, or another suitable non-nucleophilic solvent). The solution is stirred at room temperature for one to three days. The solid is filtered, washed with THF (or another suitable non-nucleophilic solvent), and optionally recrystalised. For the two different isobaric versions of piperidine acetic acid, either bromoacetic-1-$^{13}$C acid (Aldrich PN 27,933-1) or bromoacetic-2-$^{13}$C acid (Aldrich PN 27,935-8) can be substituted for bromoacetic acid. Isomer substituted piperidine can be obtained from sources such as Cambridge Isotope Laboratories.

To convert the acetic acid derivatives to active esters, such as an N-hydroxysuccinimidyl ester, dimethylformamide (DMF) is dissolved in tetrahydrofuran (or another suitable non-nucleophilic solvent). This solution is added dropwise to a stirred solution of an equal molar amount of thionyl chloride (based upon the molar quantity of DMF) dissolved in tetrahydrofuran (or another suitable non-nucleophilic solvent) and cooled in an ice bath. After complete addition and 30 minutes on ice, the ice bath is removed and solid N-hydroxysuccinimide is added immediately followed by piperidine acetic acid (or -1-$^{13}$C or -2-$^{13}$C piperidine acetic acid). The reaction is left vigorously stirring over night at room temperature. The product piperidine acetic acid N-hydroxysuccinimide ester is then isolated from the reaction mixture possibly by mere filtration. Recrystallization and/or chromatography can optionally be used to purify the crude product.

Example 7

Exemplary Synthesis of Piperazine Acetic Acid N-Hydroxysuccinimide Ester

A solution containing two equivalents of piperazine dissolved in tetrahydrofuran (THF) is added dropwise to a solution containing one equivalent of bromoacetic acid (as compared with the amount of piperazine) dissolved in tetrahydrofuran. The two solutions should be as concentrated as is practical. The resulting reaction solution is stirred at room temperature for one to three days. The solid is filtered, washed with THF, and optionally recrystallised. For the two different isobaric versions of piperidine acetic acid, either bromoacetic-1-$^{13}$C acid (Aldrich PN 27,933-1) or bromoacetic-2-$^{13}$C acid (Aldrich PN 27,935-8) can be substituted for bromoacetic acid.

To convert the acetic acid derivatives to active esters, such as an N-hydroxysuccinimidyl ester, dry dimethylformamide (DMF, 1.75 g, 0.024M) can be dissolved in tetrahydrofuran. This solution can be added dropwise to a stirred solution of an equal molar amount of thionyl chloride (based upon the molar quantity of DMF) dissolved in tetrahydrofuran and cooled in an ice bath. After complete addition and 30 minutes on ice, the ice bath can be removed and solid N-hydroxysuccinimide added immediately followed by piperazine acetic acid (or -1-$^{13}$C or -2-$^{13}$C piperidine acetic acid). The reaction can be left vigorously stirring over night at room temperature. The product piperazine acetic acid N-hydroxysuccinimide ester can then be isolated from the reaction mixture possibly by mere filtration. Recrystallization or chromatography can then be used to purify the crude product.

Example 8

Exemplary Synthesis of N,N'-(2-methoxyethyl)-glycine Active Ester

To 1.1 mole of bis(2-methoxyethyl)amine (Aldrich Chemical) was added dropwise 500 mmol of tent-butyl chloroacetate (Aldrich Chemical). The reaction was allowed to stir for three days and was then worked up. To the final reaction contents was added 250 mL of dichloromethane (DCM) and 200 mL of water. To this stirring solution was added portionwise, 300 mmol of solid potassium carbonate ($K_2CO_3$). After complete mixing, the layers were separated. The DCM layer was washed once with a volume of water, dried ($Na_2SO_4$), filtered and evaporated to yield 66.3 g of a very thin yellow oil. This crude product was Kugelrohr distilled at 60° C. (200-500 µM Hg) to yield 58.9 g of a clear colorless oil (238 mmol; 95%).

To the purified (stirring) N,N'-(2-methoxyethyl)-glycine-tert-butyl ester was slowly added 12.1 mL of concentrated hydrochloric acid. The reaction was allowed to stir overnight and then the byproducts (e.g. water, HCl, isobutylene) were removed by vacuum evaporation. $^1$H-NMR analysis indicated the t-butyl ester was hydrolyzed but it appeared that there was water and HCl still present. The crude product was co-evaporated 2× from acetonitrile (ACN) but water and HCl were still present. To eliminate impurities, a 4.4 g aliquot was removed from the crude product and Kugelrohr distilled at 135-155° C. (100-200 µM Hg with rapidly dropping pressure after distillation began). Yield 4.2 g (18.4 mmol; 95% recovery of thick, clear, colorless oil). The distilled product did not contain any water or HCl.

The active ester (e.g. N-hydroxysuccinimidyl ester) of any suitable isotopically labelled substituted or unsubstituted N,N'-(2-methoxyethyl)-glycine can then be prepared by methods known in the art, such as those described herein.

Example 9

Exemplary Method for Preparing a Solid Support Comprising Labelling/Tagging Reagents A commercially available peptide synthesis resin comprising a "sterically hindered cleavable linker" is reacted with at least two-fold excess of an aminoalkyl piperazine (e.g. 1-(2-aminoethyl)piperazine, Aldrich P/N A5, 520-9; isomeric versions can be made by the process illustrated in FIG. 11 in combination with the description in the specification). By "sterically hindered cleavable linker" we mean that the linker comprises a secondary or tertiary atom that forms the covalent cleavable bond between the solid support and the atom or group reacted with the cleavable linker. Non-limiting examples of sterically hindered solid supports include: Trityl chloride resin (trityl-Cl, Novabiochem, P/N 01-64-0074), 2-Chlorotrityl chloride resin (Novabiochem, P/N 01-64-0021), DHPP (Sachem, P/N Q-1755), MBHA (Applied Biosystems P/N 400377), 4-methyltrityl chloride resin (Novabiochem, P/N 01-64-0075), 4-methoxytrityl chloride resin (Novabiochem, P/N 01-64-0076), Hydroxy-(2-chorophnyl) methyl-PS (Novabiochem, P/N 01-64-0345), Rink Acid Resin (Novabiochem P/Ns 01-64-0380, 01-64-0202), NovaSyn TGT alcohol resin (Novabiochem, P/N 01-64-0074). Excess reagents are then removed by washing the support. The secondary amine of the support bound piperazine is then reacted with an excess of bromoacetic acid in the presence of a tertiary amine such as triethylamine. Excess reagents are then removed by washing the support. Depending on the method to be used to make an active ester of the carboxylic acid (e.g. whether or not a salt of the carboxylic acid is required for the active ester synthesis), the wash can be selected to have a pH that is adjusted to protonate the support bound carboxylic acid group of the bis-alkylated piperazine. The carboxylic acid group of the support bound piperazine is then converted to an active ester (e.g. N-hydroxysuccinimidyl ester) using procedures known in the art for the production of acid esters of a carboxylic acid, such as those described above. The resulting solid support can thereafter be used to label/tag analytes of a sample (e.g. peptides) having nucleophilic functional groups. The labeled/tagged analytes can then be released from the support as described by the manufacturer's product instructions. The product of each cleavage reaction can then be combined to form a sample mixture.

B: Synthesis of N-Methyl Piperazine Derivatives:
General Synthetic Notes: Unless otherwise stated, chemicals were purchased from commercial sources and used as received. Unless otherwise stated, the following chemicals were purchased from Sigma-Aldrich. Trifluoroacetic anhydride (TFAA, P/N 106232), N-Hydroxysuccinimide (NHS, P/N 13067-2), tert-Butyl bromoacetate (P/N 124230), 4-Nitrophenyl (4-NP) trifluoroacetate (P/N N22657), Pentafluorophenyl (Pfp) trifluoroacetate (P/N 377074), tert-butyldimethylsilyl (TBDMS) cyanide (407852), 1-(Trimethylsilyl) imidazole (P/N 153583), Phenyl bromoacetate (P/N 404276), Pentachlorophenol (Pcp-OH, P/N P2604), 2,2,2-Trifluoroethanol (P/N 326747), 1,1,1,3,3,3-Hexafluoro-2-propanol (HFI—OH, P/N 105228), (3-Hydroxy-1,2,3-benzotriazin-4 (3H)-one (Dhbt-OH, P/N 327964), Oxalyl chloride (P/N 320420), 1-Methylpiperazine (P/N 130001), Tetrahydrofuran (THF dry, P/N 186562). Dichloromethane (DCM dry, P/N 270997), 4 M hydrochloric acid (HCl) solution in dioxane (P/N 345547), HCl (gas, P/N, 295426), 3-Nitrophenol (3-NP—OH, P/N 163031) 1,5,7-Triazabicyclo[4.4.0]dec-5-ene (TBD) bound to polystyrene crosslinked with 2% DVB, Capacity (base): ~2.6 mmol/g (ss-TBD, Fluka, P/N 90603), $H_2^{18}O$ (Isotec, 95 $^{18}O$ atom % (P/N 329878) or 99% $^{18}O$ atom % (P/N 487090)), $Br^{13}CH_2COOEt$ (Cambridge Isotope Laboratories (CIL), P/N CLM-1010-5), $Br^{13}CH_2^{13}COOEt$ (CIL, P/N CLM-1011-1), $BrCH_2C^{18}O^{18}OH$ (Isotec, P/N 597031). All moisture sensitive reactions were performed under nitrogen or argon atmosphere.

Isotopically enriched starting materials were generally obtained from either Isotec (a Sigma-Aldrich company) or Cambridge Isotope Laboratories (Andover, Mass.). Generally, the most highly enriched starting materials were obtained and used in the production of the isotopically enriched piperazine derivatives. However, the state of isotopic enrichment of starting materials is a choice which the ordinary practitioner will appreciate strikes a balance between the price of the starting materials (wherein the higher the state of isotopic enrichment, the higher the price) and requirement for purity of the enriched isotopes in the final product. Accordingly, the ordinary practitioner will appreciate that the most practical method of synthesis of isotopically enriched compounds may not always proceed through the most common synthetic routes. Indeed, there may be two or more different routes to the different isotopic variants of the same compound. Thus, for some reactions and/or compounds described herein, various synthetic routes have been undertaken and are therefore discussed below. Certain advantages and caveats pertaining to these routes are also discussed.

I. Synthesis of Isotopically Labeled N-Methyl Piperazines

Figure 1A:
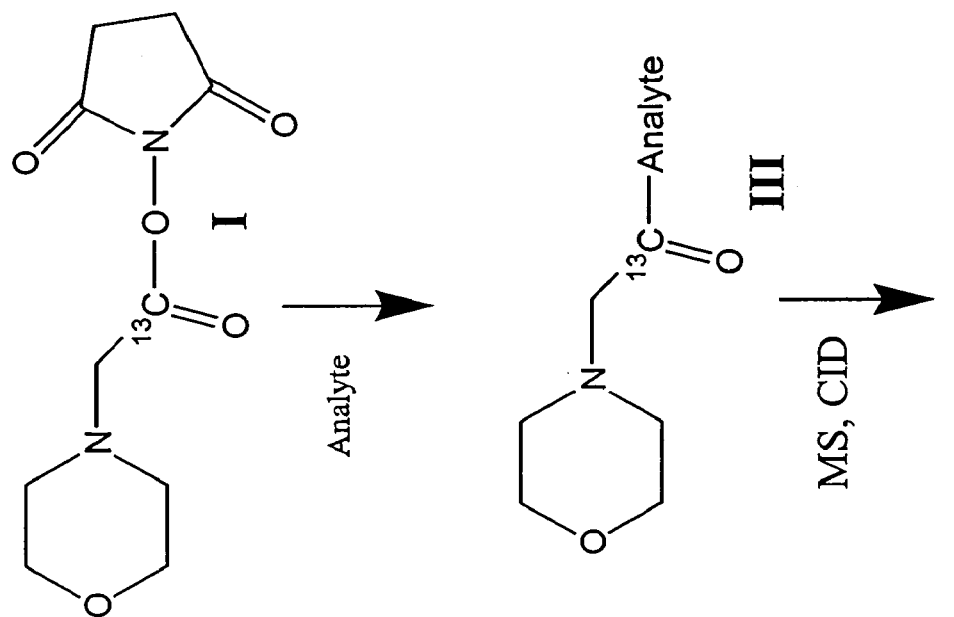
Figure 1B:
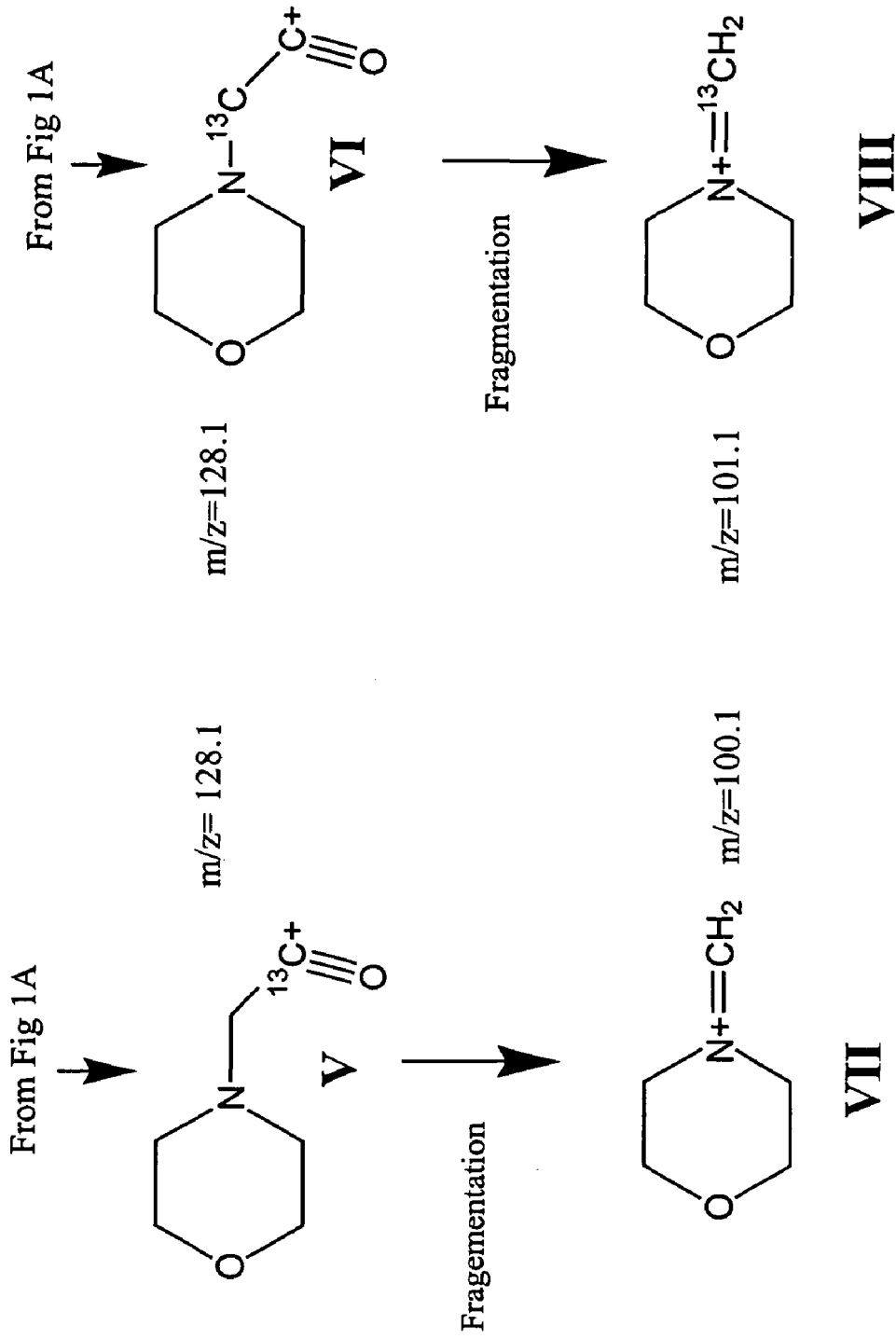
FIG. 1B illustrates the fragmentation of the labeled analyte illustrated in FIG. 1A to thereby produce reporter moieties (e.g. compounds VII and VIII as signature ions) of different masses from the isobarically labeled analytes.

Note: Unlabeled N-methyl piperazine (a.k.a: 1-methyl piperazine) is commercially available from a variety of sources. However, no source for any type of isotopically enriched N-methyl piperazine (as a stock item) could be found. It was determined however that suitably protected glycine and sarcosine could be condensed, cyclized and the product (a diketone) could be reduced to thereby produce N-methyl piperazine (See FIG. 1). Furthermore, it was determined that all possible permutations of $^{15}N$ and $^{13}C$ isotopically labeled glycine, as well as partially protected versions thereof (e.g. t-boc protected amino acids), were commercially available from sources such as Isotec or Cambridge Isotope Laboratory, Inc. Accordingly, this appeared to be a promising route to various N-methyl piperazine compounds comprising one or more heavy atoms. Because appropriately protected (t-boc) isotopically enriched glycines and suitably protected sarcosine can be purchased from commercial sources and because the protection of amino acids, such as glycine and sarcosine, are well-known, this discussion of the synthetic route to N-methyl piperazine begins with the suitably protected amino acids (FIG. 1).

Example 10

General Procedure for the Condensation of Sarcosine Ester and t-boc-Glycine (FIG. 13)

Note: Sarcosine is commercially available as either the methyl or the ethyl ester. Either can be used in the condensation reaction.

To a round bottom flask (RBF) was added 1.1 equivalent (eq.) of sarcosine ethyl ester (31) and 1 eq. of t-boc-glycine (30) (including isotopically labeled t-boc-glycines for the production of various isotopically labeled N-methyl piperazines). The solid was then dissolved with the addition of dichloromethane (DCM) (~20 mL/g of t-boc-glycine). To this stirring solution was added 1.1 eq. of N-methyl morpholine (NMM) then 1.1 eq. of dicyclohexylcarbodiimide (DCC) in DCM. A precipitate formed within minutes. The reaction was stirred overnight. The reaction was monitored by thin layer chromatography (TLC). If t-boc-glycine was still present, additional DCC in DCM was added. When the reaction was determined to be complete, the solids were filtered off and the cake was rinsed with DCM. The product containing solution was then evaporated to dryness.

The product was purified by silica gel chromatography using a column packed in 50% ethyl acetate (EtOAc)/hexane. A small amount of the 50% EtOAc/hexane solution was used to dissolve/suspend the dried down product (not all will dissolve). This solution/slurry was loaded onto the packed column. The column was eluted 50% EtOAc/hexane to obtain the minimally retained product. Product containing fractions were evaporated to provide an oil, speckled oil, or flaky solid (materials that are higher in heavy atom isotope content appeared to exhibit more characteristics of a solid).

TLC Conditions: EtOAc (Developed with Ninhydrin and Heat)

Product (32) Rf~0.85
t-boc-glycine (30) Rf~0.3 (broad tailing)
Sarcosine-OEt (31) Baseline
NMM Faintly visible just above sarcosine Example 11

General Procedure for the Synthesis of 1-Methyl-2,5-Diketopiperazine (FIG. 13)

A solution of 1:1 trifluoroactetic acid (TFA):DCM containing 0.5% water was prepared. This solution was added to the column purified product (32) of the condensation reaction (~10 mL/g starting material). The resulting solution was stirred for 30 minutes and then the solvents removed by rotoevaporator. Ethanol (~10 mL/g starting material) was then added to the reaction flask and this solution was again striped to dryness. The procedure was repeated with toluene. The product was again dissolved in ethanol in the reaction flask and anhydrous potassium carbonate (4 eq) was added. The solution bubbled vigorously for a short period following the addition of the potassium carbonate. A drop of the reaction mixture was removed, diluted with water, and the pH of the solution was determined. If the pH was below 8, more potassium carbonate was added. Once the pH was confirmed to be greater than 8, the reaction was allowed to reflux overnight. The warm reaction mixture was then passed through a plug of Celite to remove the excess salts. The cake was rinsed twice with anhydrous ethanol. The filtrate was transferred to a larger flask and stripped to dryness. The product foam was redissolved in 9:1 ethyl acetate-methanol and passed through a plug of silica-gel. The silica-gel was then washed with ~4 column volumes of 9:1 ethyl acetate-methanol. All fractions were evaporated to dryness.

Notes and alternative procedures: Deprotection of the t-boc group with the TFA/DCM/H$_2$O solution can be followed by TLC (ninhydrin/heat shows conversion of the spot at Rf 0.85 to a dark red-brown spot at origin). After deprotection, it is also acceptable to add methanol, concentrate and re-treat with methanol followed by a second concentration and drying in vacuo to remove excess TFA.

In some reactions, concentrated ammonium hydroxide (large excess ~60 mL per 16 mmol of starting material) was substituted for potassium carbonate. (When concentrated ammonium hydroxide was added to the reaction at room temperature, it generated a white insoluble material and a slightly milky reaction mixture.) After the addition of concentrated ammonium hydroxide, the flask was sealed with septum to prevent loss of ammonia. Cyclization appeared to be complete after overnight (12 hrs) reaction although in some cases heating to 60° C. over several hours was sufficient. The reaction was monitored by TLC (10% MeOH/DCM visualized with 10% phosphomolybdic acid (PMA) in MeOH with heat). The product appeared as a blue spot at Rf 0.54. Since the deblocked material (red-brown spot at origin) could not be visualized with PMA, another TLC was performed as a cross-reference using ninhydrin/heat.

When cyclization was deemed complete by TLC analysis, the mixture was filtered and the flask and solids were rinsed with DCM. The filtrate was concentrated and redissolved in 10% MeOH/DCM before chromatography. The white waxy solids were partially insoluble in the 10% MeOH/DCM so the material was sonicated. Sonification successfully dissolved the mixture that was then applied to the column. The first fraction eluted was mainly the white waxy solid. The major fraction (the dione product (33)) eluted next and was followed by another minor impurity (Rf 0.3). It was observed that in cases where incomplete TFA removal resulted in formation of ammonium triflate, this impurity co-eluted with the product and the secondary material. A second column could be used to completely purify the desired product.

The melting points of the dione (33): 116, 117: 138-139 for model compound: lit: 136-139 (J. Het. Chem. 18, 423, 1981); 142-143 (J. Biol. Chem. 61, 445, 1924).

TLC Condition: 9:1 Ethyl Acetate-Methanol (Develop with Phosphomolybdic Acid and Heat)

Product Rf~0.2

Alternative TLC Condition: 10% MeOH/DCM; Develop with Heat

Product (blue spot) Rf=0.54

1H-NMR Data

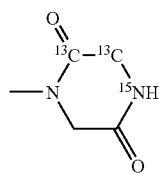

NMR (D$_6$ DMSO)—N1-CH$_3$, d 2.79, 2.80 3H; 3-CH$_2$ dd 3.94, 3.92, 3.59, 3.57 2H; 6-CH$_2$ d 3.87, 3.86 2H; 4-NH b 8.11H.

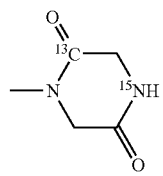

NMR (D$_2$O)—N1-CH$_3$, d 3.00, 2.99 3H; 3-CH$_2$ d 4.08, 4.08 2H, 6-CH$_2$ d 4.14, 4.14 2H.

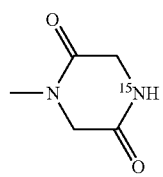

NMR (D$_6$ DMSO)—N1-CH$_3$, s 2.80 3H; 3-CH$_2$ s 3.76 2H; 6-CH$_2$ s 3.86 2H; 4-NH d 8.03, 8.26 1H.

Example 12

General Procedure for the Synthesis of N-Methyl Piperazine (Route A; FIG. 13)

A saturated solution of sodium sulfate was prepared. Tetrahydrofuran (THF) (4 mL per mmol starting material based upon the material used in Example 11) was added to the diketopiperazine formed using the procedure of Example 11. The reaction flask was fit with a reflux condenser and three equivalents of 1M LiAlH$_4$ in THF (LAH solution; it may be possible to substitute Red-Al or other reducing reagent for LAH but this has not been attempted) was added to the solution through a dropping funnel. There was vigorous hydrogen evolution at the initiation of the addition but this subsided as the addition continued. The reaction was heated to reflux for 4 hours. After the reaction was complete, the solution was cooled to room temperature and the remaining LAH was quenched with the very slow addition of saturated aqueous sodium sulfate (¼ the volume of the LAH solution added). The reaction appeared as a gray suspension.

DCM was added to this suspension (½ volume of the THF) and the gray gel-like solid was removed by filtration. The flask and filtered solids were then thoroughly washed 2× with DCM (¼ volume of the THF). The combined organic solution (DCM/THF) was then dried with Na$_2$SO$_4$ (solid-anhydrous) and filtered. (In some early experiments the N-methyl piperazine was isolated as an oil (free base and not as a TFA or HCl salt) but the product was determined to be a volatile oil and therefore not be isolated in high yield).

Di-tert-butyl-dicarbonate (3 equivalents) was added to this solution that was stirred and vented overnight. TLC was used to monitor the reaction. Once complete, the solvent was removed by rotary evaporation to yield a liquid. This liquid is slightly volatile, so low vacuum evaporation of solvent is recommended (high vacuum conditions should be avoided). The product was dissolved in DCM and loaded onto a silica-gel column packed with 8% methanol in ethyl acetate. Product was eluted with the 8% methanol in ethyl acetate solution. Product containing fractions were determined by TLC, pooled, and evaporated to a liquid. This liquid was taken directly to the deprotection reaction. Note: the t-boc deprotection was performed only as a means to isolate the crude N-methyl piperazine product but this requires subsequent deprotection.

TLC—N-Methyl Piperazine (Develop with Ninhydrin)
4:1:1 Ethanol:Water:Ammonium hydroxide
Product Rf=0.6
TLC—N1-t-Boc-N2-Methyl Piperazine (Develop with Ninhydrin)
4:1 DCM.MeOH
Product Rf=0.5

Deprotection:

A solution of 1:1 TFA, DCM with 0.5% water was prepared. This solution was added to the material isolated from the reduction, above (~10 mL/g starting material). The reaction was stirred for 30 minutes then the solvent was removed with a rotoevaporator. Solvent evaporation was terminated when no more solvent was observed to be collecting on the condenser. TFA was added to the product residue (~2 mL/g starting material) to form a free flowing solution. The TFA solution was transferred to a centrifuge tube and diethyl ether was added to precipitate the product salt. The solution was mixed using a vortex. The solution was then centrifuged and the supernatant decanted to collect the precipitate. The filtrate was then washed 1 time with ether by resuspending the product, vortexing, and re-centrifugation. Product was dried under low vacuum to remove residual ether.

1H-NMR data:

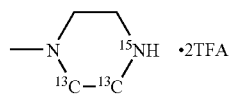

NMR (D$_2$O)—N1-CH$_3$, d 3.02, 3.03 3H; methylenes, broad triplet 3.3-3.9 8H

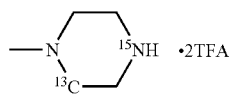

NMR (D$_2$O)—N1-CH$_3$, d 3.02, 3.03 3H; methylenes, broad 3.40-3.85 8H

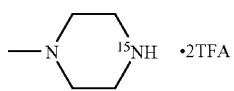

NMR (D$_2$O)—N1-CH$_3$, s 3.03 3H; methylenes, broad 3.50-3.75 8H

Example 13

General Procedure for the Synthesis of N-Methyl Piperazine (Route B; FIG. 13)

The product of the procedure of Example 11 was dissolved in anhydrous THF (5 mL per mmol SM) in a multi-neck RBF fitted with condenser, addition funnel and argon (Ar) inlet. To this solution was added 3 equivalent of the LAH solution slowly through a dropping funnel at RT under Ar. Vigorous hydrogen evolution was observed at the beginning. After addition, the cloudy solution was heated to reflux for 3 hours. TLC was used to determine when the reaction was complete (disappearance of starting material (SM), 10% MeOH/DCM TLC developing solvent, PMA as visualizer). After the reaction was complete, the solution was cooled to room temperature and quenched with the very slow addition of saturated aqueous sodium sulfate (¼ the volume of the LAH solution added). White gel-like solid solution was passed through a plug of Na$_2$SO$_4$ solid to remove H$_2$O. The filter cake was washed with THF several times (400 mL per gram SM) until TLC of the washing showed a little product. Then TFA (4 eq) was added to the THF solution (HCl in dioxane could also be added if the HCl salt was desired). The color of the solution changed to light brown from pale yellow. The solution was concentrated on a rotoevaporator under reduced pressure to yield brown oil. The light brown product was precipitated as bis-TFA salt by adding ether (42 mL per 1 gram SM) to yield of 80% N-methyl-piperazine. $^1$H NMR (D$_2$O) was used to confirm the desired product.

II. Alkylation of N-Methyl Piperazines to Form N-Methyl Piperazine Acetic Acids

Note: FIG. 17A illustrates the pathway for the synthetic incorporation of heavy atom isotopes into four isobaric labeling reagents referred to herein as 114, 115, 116 and 117. As can be seen from FIG. 17A, certain of the heavy atom isotopes can be incorporated by the choice of the commercially available isotopically labeled glycine used in the production of the N-methyl piperazine. Certain other heavy atoms can be incorporated during the alkylation reaction based upon the choice of the commercially available bromoacetic acid. In some cases, the $^{18}$O can be incorporated through an efficient exchange using $^{18}$O labeled water. The labeling reagents are designated 114, 115, 116 and 117 based upon the mass of the fragment that forms a signature ion in the mass spectrometer (see: FIG. 17A and FIG. 17B) once the reagent has been fragmented by the application of dissociative energy.

With reference to FIG. 14A, scheme A is useful for producing the N-methyl piperazine acetic acid as a zwitterion and not as a salt (e.g. mono or bis TFA or HCl salt). With reference to FIG. 14B, scheme B is useful since it requires the use of only one equivalent of N-methyl piperazine for the production of the N-methyl piperazine acetic acid thereby foreclosing the waste of the valuable isotopically labeled starting material. With reference to FIG. 2C, scheme C is useful for alkylations involving the isotopically labeled bromoacetic acid, particularly the $^{18}$O labeled bromoacetic acid as it was expected to reduce the occurrence of $^{18}$O scrambling (or exchange with $^{16}$O from residual water).

Example 14

Procedure for the Synthesis of Isotopically Labeled N-Methyl Piperazine Acetic Acids (Scheme A; FIG. 14A)

To a stirring solution of 1.18 g (11.83 mmol) N-methyl piperazine in 15 mL of toluene at room temperature was added 1 g (5.91 mmol) of ethylbromoacetate, 1,2-$^{13}$C dropwise, over a period of 15 minutes. Immediate formation of white solid was observed. The reaction mixture was then heated in an oil bath at 90° C. for 4 hr. After cooling the mixture to room temperature, the off-white solid was removed by filtration, and washed with 25 mL of toluene. The combined filtrate and washings was then concentrated in a rotoevaporator, and the residue was dried under high vacuum for 5 hours to yield 1.10 g (quantitative) of ethyl ester of N-methyl piperazine acetic add-1, 2-$^{13}$C (38) as an off-white oil. The crude product (38) was analyzed by MS and $^1$H-NMR, and was directly used for the next step without further purification. MS (ESI, m/z): 189.16 (M+1), $^1$H-NMR (DMSOd$_6$) δ 4.2 (m, 2H), 3.4 (d, 1H, J=7 Hz), 3.05 (d, 1H, J=7 Hz)), 2.4-2.7 (b, 8H), 2.3 (s, 3H), 1.25 (t, 3H).

A solution of ethyl ester of N-methyl piperazine acetic acid (38) (1.1 g, mmol), prepared as described above, in water (20 mL) was refluxed for 24 hr. The reaction was monitored by MS analysis. After 24 hr, the reaction mixture was concentrated in a rotoevaporator to afford white solid product, which was triturarted with acetone (10 mL) overnight. The product was then separated by filtration and dried under high vacuum overnight at 45° C. in a vacuum oven, to yield 780 mg of N-methyl piperazine acetic acid, 1, 2-$^{13}$C (39), as a white powdery solid. 300 mg of the product was further purified by sublimation (1 mm/Hg, 110-120° C.) to yield 270 mg of white solid. MS (ESI, m/z); 161 (M+1), $^1$H-NMR (DMSOd$_6$) δ 3.3 (d, 1H, J=7 Hz), 2.95(d, 1H, J=7 Hz), 2.55-2.75 (b, 4H), 2.3-2.45 (b, 4H), 2.18 (s, 3H)

Notes: This procedure utilizes unlabeled N-methyl piperazine. This procedure is useful for producing the zwitterion of N-methyl piperazine acetic acid.

The product can also be isolated as the mono or bis-HCl or mono or bis-TFA salt by treatment with the appropriate acid prior to or subsequent to its isolation as described above.

Example 15

Procedure for the Synthesis of Isotopically Labeled N-Methyl Piperazine Acetic Acids (Scheme B; FIG. 14B)

To a slurry of 200 mg (1.14 mmol) of N-methylpiperazine-$^{15}$N.2HCl (the 2TFA salt can also be used) in methanol (MeOH, 14 mL), was added 1.76 g (4.59 mmol) of ss-TBD, with a loading of 2.6 mmol/g, followed by CH$_2$Cl$_2$ (6 mL). The mixture was then sonicated for 15 minutes and was then cooled in an ice bath under an argon atmosphere. To this vigorously stirred slurry, a solution of 193 mg (1.14 mmol) of ethylbromoacetate-2-$^{13}$C in acetonitrile (3 mL) was added dropwise using a syringe pump (maintaining a rate of 2 mL/hr). After completion of the addition, the ice bath was removed and the mixture was continued stirring at room temperature overnight (18 hr). The mixture was then filtered through a sintered funnel, and the solid was washed several times with MeOH (4×10 mL). The combined filtrate and washings were then concentrated in a rotoevaporator, and the residue was kept under high vacuum to yield 111 mg (51%) of the ethyl ester of the N-methyl piperazine acetic acid (40) as an off white solid. This crude product was directly used for the next step without further purification. MS (ESI, m/z) 189 (M+1). $^1$H-NMR (DMSOd$_6$) δ 4.05 (q, 2H), 3.3(s, 1H), 3.0 (s, 1H), 2.4-2.5 (b, 4H), 2.2-2.4 (b, 4H), 2.1 (s, 3H), 1.15 (t, 3H).

The product was hydrolyzed in the manner described in Scheme A, above. The following analytical data was obtained for the product.

MS (ESI, m/z) 161 (M+1). $^1$H-NMR (DMSOd$_6$) δ 3.35(s, 1H), 3.05 (s, 1H), 2.65-2.8(b, 4H), 2.5-2.65(b, 4H), 2.35 (s, 3H),

Without substantial variation, above general procedure was applied to other isotopically labeled N-methyl piperazines to produce various isotopically labeled N-methyl piperazine acetic acid derivatives.

The product can also be isolated as the bis-HCl or bis-TFA salt by treatment with the appropriate acid prior to or subsequent to its isolation as described above.

Example 16

Figure 14C:
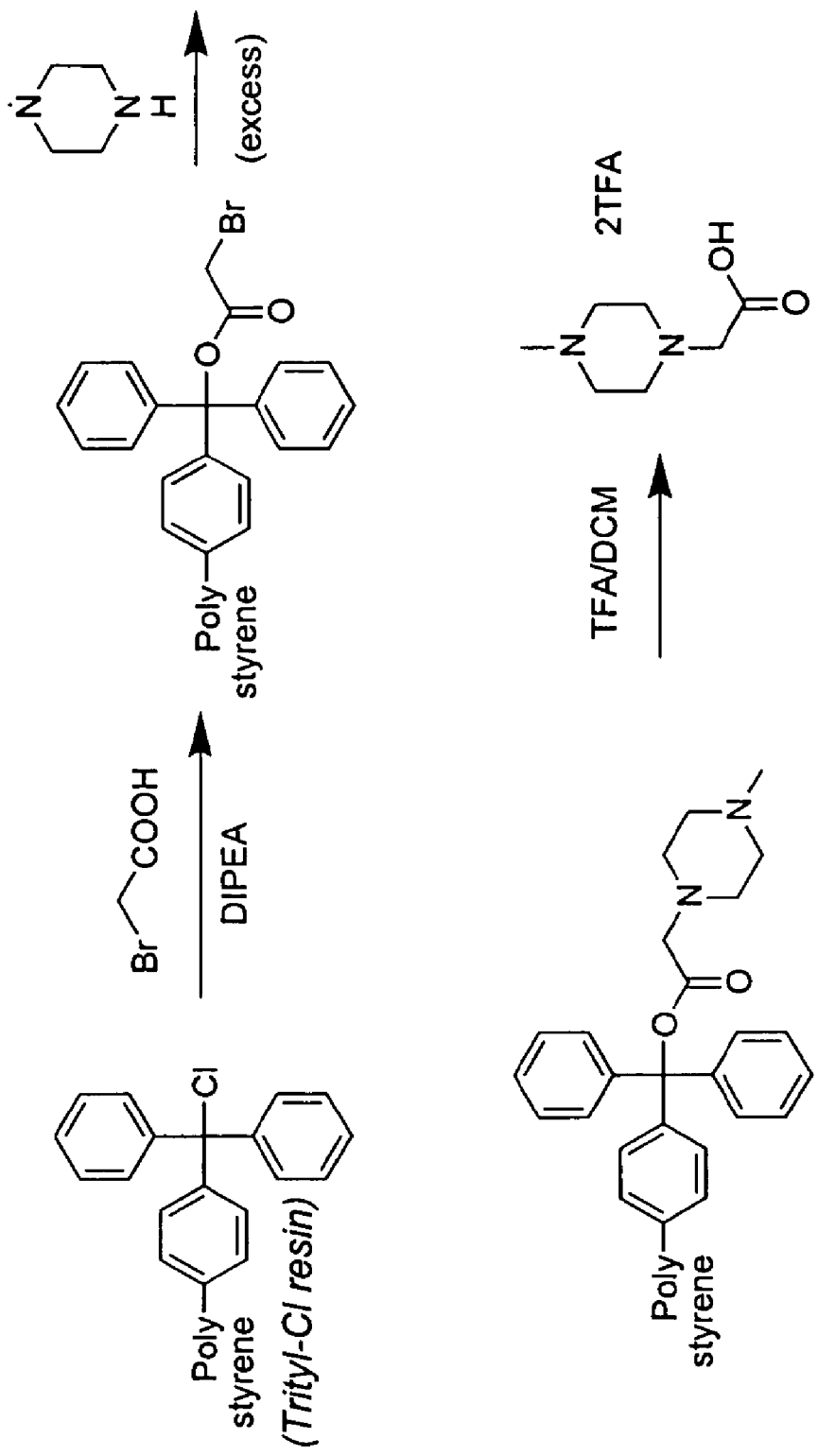
FIG. 14C is an illustration of yet another synthetic scheme for the synthesis of N-methyl piperazine acetic acids.

General Procedure for the Synthesis of Isotopically Labeled N-Methyl Piperazine Acetic Acids (Scheme C; FIG. 14C)

To a solution of bromoacetic acid (715 mg, 5 mmol) in DCM (15 mL) was added 700 mg of trityl-Cl resin (1 mmol, 1.45 mmol/g) followed by diisopropylethylamine (DIPEA) (1.79 mL, 10 mmol). This solution was mixed at room temperature for 1 hour. The resin was then filtered and washed with dichloromethane (3×4 mL) followed by a wash with a solution of dichloromethane-methanol-DIPEA (17:2:3, 5 mL) and finally a wash with dichloromethane (3×4 mL).

The resin was then treated with a solution of N-methyl piperazine (N-MP) (0.57 mL, 5 mmol) in DMF (5 mL) for 30 minutes and then washed with DMF and dichloromethane (3×4 mL each). The N-MPA so generated on resin was cleaved with a 25% solution of TFA in dichloromethane (10 mL for 5 min)) and resin was washed with the same solution (2×5 mL). After evaporation of TFA, the product was precipitated and washed with ether (388 mg, 99% yield, bis TFA salt). The product was identified by NMR (matched with literature) and with ES-MS (Calculated MH$^+$=159.11, found 159.14).

Without substantial variation, the above general procedure was applied to other isotopically labeled N-methyl piperazines to produce various isotopically labeled N-methyl piperazine acetic acid derivatives.

The product could also be isolated as its bis-HCl salt if HCl was used to cleave the product from the support rather than TFA. Other acids could also be used for the cleavage reaction and product would be the salt of the acid used.

III. Methods for the Incorporation of $^{18}$O into N-Methyl Piperazine Acetic Acids Note: In the initial experiments, incorporation of $^{18}$O into the N-methyl piperazine acetic acid was attempted as illustrated in FIG. 15A using $^{18}$O labeled bromoacetic acid (custom synthesized by CIL). Caveats to this approach include the possibility that in subsequent reactions, the $^{18}$O can exchange with $^{16}$O from residual water or can otherwise exchange with $^{16}$O from other reagents during the esterification process. The more recently applied synthetic procedure is illustrated in FIG. 15B and capitalizes on the $^{16}$O$\leftrightarrow^{18}$O exchange reaction, using H$_2$$^{18}$O to drive the equilibrium reaction to formation of the desired heavy version of the N-methyl piperazine acetic acid. Though both schemes have been shown to work, Scheme B currently supports the production of the most highly $^{18}$O enriched products.

Example 17

General Procedure for the Synthesis of $^{18}$O Isotopically Labeled N-Methyl Piperazine Acetic Acids, Including Conversion to the Active Ester (Scheme A; FIG. 15A)

To a solution of TBDMS-CN (172 mg, 1.190 mmol)) in DCM (0.575 mL) was added $^{18}$O labeled bromoacetic acid (42) (170 mg, 1.189 mmol) under an argon atmosphere and the solution was heated to 80° C. for 20 minutes and then cooled to room temperature. The product (43) was isolated as an oil (254 mg, 85% yield). $^1$H NMR (CDCl$_3$) δ 3.58 (2H, —CH$_2$—), 0.955 (9H, (CH$_3$)$_3$—Si), 0.30 (6H, CH$_3$Si).

A solution of BrCH$_2$C$^{18}$O$_2$-TBDMS (43) (254 mg, 1 mmol) in DCM (2.5 mL) was added (34 μL/min) to an argon flushed flask containing N-MP (110 μL, 1 mmol), TBD resin (576 mg, 1.5 mmol, 2.6 mmol/g) and DCM at 0° C. After the addition was complete the reaction continued for 1 h at RT and then the resin was filtered and washed with DCM. Combined filtrate was concentrated by rotary evaporation to obtain 118 mg (42% yield) of an oil (44a & 44b or 44c).

Note: Because of the potential for $^{18}O \rightleftarrows ^{16}O$ exchange during the esterification, the N-methyl piperazine acetic acid prepared by this route was not converted to the active ester using the trifluoroacetate procedure described in Section VI, below. Instead it was converted using oxalyl chloride and NHS as described below.

To a solution of $^{18}O$ containing TBDMS ester of N-MPAA (44a & 44b or 44c) as obtained above (118 mg, 0.427 mmol) in DCM (5 mL) was added a solution of oxalyl chloride (0.427 mL, 0.854 mmol, 2 M solution in dichloromethane) at room temperature. The reaction allowed to continued for 1 hour when an off white slurry formed. Solvent and excess reagent were removed from the reaction mixture. A solution of NHS (50 mg, 0.427 mmol) in dry THF (1.4 mL) was added to the resulting solid followed by 5 mL of dichloromethane, 4 mL of THF and 246 mg of ss-TBD resin (0.640 mmol, 2.6 mmol/g). The mixture was sonicated and mixed for 20 minutes, after which the resin was filtered and washed with 5 mL of dry dichloromethane. To the filtrate so obtained was added 2 mL of 4.0 M solution of HCl in dioxane and the precipitate (45a & 45 b) was washed with dry THF (5 mL×2) and hexanes (5 mL) and dried under vacuum (10 mg, 7% yield). ES-MS (direct infusion in i-propanol) shows isotopic purity to be around 74% at this stage.

Example 18

General Procedure for the Synthesis of $^{18}O$ Isotopically Labeled N-Methyl Piperazine Acetic Acids (Scheme B; FIG. 15B)

200 mg (1.24 mmol) of N-methyl piperazine acetic acid 1, 2-$^{13}C$ (46) was weighed out in a 5 mL plastic vial flushed with argon. The vial was then transferred into a glove box and 2.5 mL of $^{18}O$-water (>99% $^{18}O$) was added. The vial was then fitted with a silicone septum, and a low stream of HCl gas was then passed through the solution using a long needle after venting the septum with an open needle. When the solution had warmed (~2 min), the HCl passage was stopped, and the septum was replaced with a screw-cap. The vial was then heated at 80° C. in a heating block for 18 hr. An aliquot was analyzed by MS and $^{18}O$ purity was calculated as 93%. The reaction mixture was then concentrated to dryness in a speedvac, and the residue was subjected to a second cycle of $^{18}O$-exchange as described above. By MS analysis the $^{18}O$ purity after the second cycle was determined as 96%. The mixture was then evaporated to dryness in a speedvac, and traces of water were removed by co-evaporation with toluene (1 mL×2). 220 mg of N-methyl piperazine acetic acid-1, 2-$^{13}C$-$^{18}O_2$.2HCl (47a) was obtained with impurity (47b). MS (ESI, m/z), 165 (M+1)

Note: The product was used without further purification in the production of active ester of the N-methyl piperazine acetic acid. The bis-TFA salt was also produced using the above-described procedure wherein TFA was substituted for HCl.

IV. Preparation of the Active Esters of the N-Methyl Piperazine Acetic Acids

Note: Several methods were employed for the production of active esters of N-methyl piperazine acetic acid. The procedure illustrated by Scheme A (FIG. 16A) worked well for the production of the fluoroalcohol esters of N-methyl piperazine (See: FIGS. 16C and 16D). The procedure illustrated by Scheme B (FIG. 16B) produced various active esters of N-methyl piperazine but unless the solid phase base was used (e.g. ss-TBD), the hydrochloride salt of solution phase base was difficult to remove. The procedure illustrated by Scheme C (FIGS. 16C and 16D) proved to be the most generally applicable route to the production of active esters of N-methyl piperazine.

Example 19

Synthesis of Active Esters of N-Methyl Piperazine Acetic Acid Via Imidazolide Formation (Scheme A, FIG. 16A)

To a solution of N-methyl piperazine phenyl ester (48) (100 mg, 0.426 mmol) and sodium phenoxide (1 mg, 9 μmol) in THF (5 mL) was added TMS-imidazole (69 μL, 0.468 mmol). The solution was mixed for 20 minutes to generate the imidazolide (49). $CF_3CH_2OH$ (80 μL, 0.213 mmol) was then added to the light yellow solution so obtained. The solution was mixed for another 30 minutes when TLC indicated clean formation of product ($R_f$=0.6, 4:1 DCM-MeOH). The reaction was then diluted to 15 mL with EtOAc and the product (50) was precipitated by addition of HCl solution in dioxane (4 M, 2 mL). After washing with THF (2×15 mL) product was isolated as white solid. NMR of the solid indicated a 1:1 mixture of product and imidazole (as HCl salt). Calculated $MH^+$=241.13, found=241.12.

1,1,1,3,3,3-Hexafluoro-2-propanol ester (51) was isolated using the general procedure set forth above provided however that $(CF_3)_2CHOH$ was substituted for $CF_3CH_2OH$. The following analytical data was obtained for this product. ($R_f$=0.37, 9:1 DCM-MeOH). Calculated $MH^+$=309.11, found=309.11.

Note: N-methyl piperazine phenyl ester was prepared by the alkylation procedures described above (See FIGS. 14A and 14B) wherein phenyl bromoacetate is substituted for ethyl bromoacetate.

Example 20

Synthesis of Active Esters of N-Methyl Piperazine Acetic Acid Via Oxalyl Chloride (Scheme B, FIG. 16B)

To a suspension of N-methyl piperazine acetic acid (N-MPAA) (79 mg, 0.5 mmol) in DCM (25 mL) was added a solution of oxalyl chloride (4 mL, 0.8 mmol, 2.0 M solution in DCM) over 10 minute at room temperature. After another 30 minutes of reaction, solvent and excess reagent were removed under reduced pressure to give a white solid (52). A solution of NHS (57 mg, 0.5 mmol) in DCM (25 mL) was added to the solid followed by ss-TBD (390 mg, 1 mmol, 2.6 mmol/g). The resulting solution was sonicated for 5 minute when all solid dissolved. The ss-TBD resin was removed by filtration and solvent was evaporated to yield a white foam (97% yield). Product was characterized by ES-MS as before.

Synthesis of Active Esters of N-Methyl Piperazine Acetic Acid Via Trifluoroacetate Esters (Scheme C, FIGS. 16C and 16D)

Note: Conversion of the N-methyl piperazine acetic acids (N-MPAAs) to their active esters via the trifluoracetate ester is typically a two-step process. Except for the rare case where the reagent is commercially available (See: Table 2), the first step involves the preparation of a reagent for esterifying the acetic acid. The second step involves reacting the esterifying reagent with the N-methyl piperazine acetic acid to produce the active ester. Various active esters were produced and tested for the aqueous labeling of peptides. Though the NHS ester proved to be quite useful for this application, other esters may prove useful in other applications. Nevertheless, this method of producing the active esters proved to be quite robust and generally applicable across a wide variety of compounds. FIG. 16D illustrates 7 different active esters that were produced using the same generic procedure.

Example 21

Synthesis of N-Hydroxysuccinimide Trifluoroacetate[10,11] and Other Trifluoroacetate Esters Trifluoroacetic anhydride (4.9 mL, 4×8.68 mmol (2.5-4 equivalents is typically used) was added to N-hydroxysuccinimide (NHS) (1 g, 8.69 mmol) and stirred under argon for 1-2 h to produce a homogeneous reaction mixture. Excess reagent and by-product $CF_3COOH$ were removed under reduced pressure (rotary evaporation). The product was obtained as white solid in quantitative yield. The solid was dried under high vacuum for 3-4 h and stored under argon (Ar) or nitrogen ($N_2$) gas.

With reference to FIG. 16D and Table 2, the trifluoroacetate ester of pentafluorophenol (Pfp) and 4-nitrophenol (4-NP) were commercially available. The remaining trifluoroacetate esters were synthesized using the above-described generic procedure provided however that the reaction time and temperature were varied. Furthermore, in some cases the products were isolated by distillation. Yields of the trifluoroacetate esters were good and in some cases near quantitative. The specific conditions used are set forth in Table 2, below.

TABLE 2

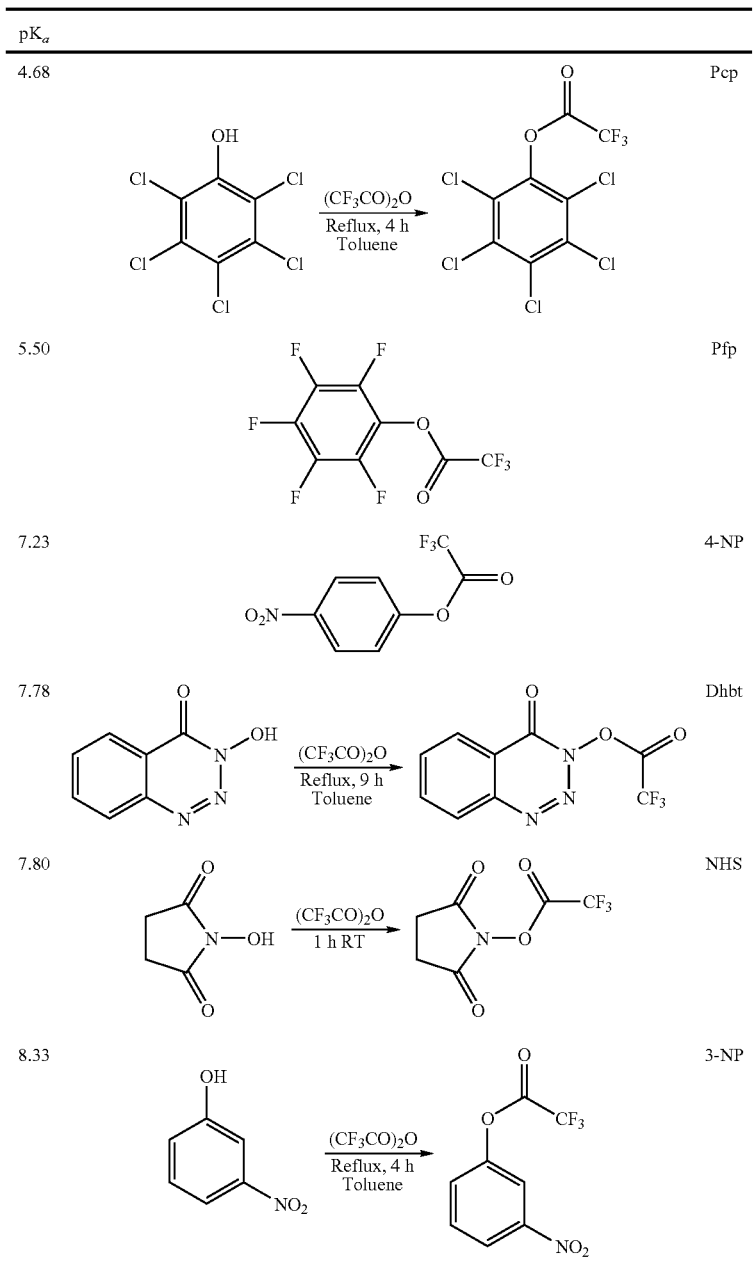

Example 22

General Method for the Preparation of Active Esters of N-Substituted Piperazine Acetic Acid from Trifluoroacetate Esters A solution of the trifluoroacetate in THF (0.58 M, 1.2 equiv) was added to a solid sample of N-methyl piperazine acetic acid and mixed in a vortex or shaker until a homogeneous solution was obtained. The reaction of the carboxylic acid with the trifluoroacetate ester was generally complete within 30 min for all cases except N-hydroypyrrolidinone (NHP, 18 h). The progress of conversion to the active ester was monitored by ES-MS. The amount of product and any starting material (N-MPAA) could be determined by direct infusion of a sample of the reaction (in ethanol) into the ES-MS. In some cases the active ester product was precipitated as dihydrochloride salt by the addition of a solution by addition of HCl solution in dioxane (4 M, 50% volume of the reaction) followed by washing with THF, ethyl acetate and hexanes. In other cases the product was isolated from the reaction as the mono TFA salt. Addition of TFA could be performed if the bis-TFA salt was desired.

| | |
|---|---|
| Dhbt ester, Calculated MH$^+$ = 304.14 | Found = 304.20 |
| NHP ester, Calculated MH$^+$ = 242.15 | Found = 242.20 |
| 4-NP ester, Calculated MH$^+$ = 280.13 | Found = 280.20 |

$^1$H NMR (400 MHz, CDCl$_3$) d 8.20 (d, 2H, J=9.2 Hz, aromatic protons), 7.25 (d, 2H, J=9.2 Hz, aromatic protons), 3.69-3.40 (broad, 2H, ring protons), 3.57 (s, 2H, —CH$_2$—CO—), 3.15-2.90 (broad, 6H, ring protons), 2.78 (s, 3H, —CH$_3$).

| | |
|---|---|
| Pfp ester, Calculated MH$^+$ = 325.10 | Found = 325.10 |
| Pcp ester, Calculated MH$^+$ = 404.95 | Found = 405.90 |
| 3-NP ester, Calculated MH$^+$ = 280.13 | Found = 280.20 |
| NHS ester, Calculated MH$^+$ = 256.13 | Found = 256.10 |

Example 23

Synthesis of the NHS-Ester of N-Methyl Piperazine Acetic Acid-1,2-$^{13}$C—$^{18}$O$_2$, 2.HCl (the 114 Labeling Reagent)

To a slurry of N-methyl piperazine acetic acid -1, 2-$^{13}$C, $^{18}$O, 2.HCl (56) (60 mg, 0.25 mmol) in THF (1.8 mL), was added DIPEA (98 mg, 0.76 mmol) under argon. The mixture was vortexed for 5 min, and the trifluoroacetate of N-hydroxysuccimide (160 mg, 0.76 mmol) was added. After sonicating for 10 minutes, the reaction mixture was stirred at room temperature for 4 hours, followed by a centrifugation to remove any undissolved material. The supernatant was decanted then diluted with THF (3 mL) and added slowly to a 4M solution of HCl in dioxane (1.8 mL). The precipitated HCl salt of the NHS-ester was separated by centrifugation, and washed with THF (3 mL×4), dried under high vacuum to yield 62 mg (74%) of the NHS ester (58) as an off-white solid. MS (ESI, m/z) 261 (M+1), $^1$H-NMR (DMSOd$_6$) δ 4.05 (d, 1H, J=7 Hz), 3.7 (d, 1H, J=7 Hz), 3.3-3.45 (b, 2H), 2.95-3.1 (b, 2H), 2.85(s, 3H), 2.75 (m, 4H).

With the exception of using a different isotopically enriched N-methyl piperazine acetic acid, the above describe procedure was followed for the production of the 115 labeling reagent (59). The analytical data for the product (59) is as follows.

MS (ESI, m/z) 261 (M+1). $^1$H-NMR (DMSOd$_6$) δ 4.05(s, 1H), 3.7 (s, 1H), 3.3-3.4 (b, 2H), 3.1-2.95(b, 4H), 2.85 (s, 3H), 2.75-2.80 (b, 1H), 2.7 (m, 4H).

Notes: The trifluoroacetate ester reagent can be reacted with the zwitterion of N-methyl piperazine acetic acid and well as with a mono salt or bis salt (e.g. mono-HCl salt, mono-TFA salt, bis-HCl salt or bis-TFA salt) of the N-methyl piperazine acetic acid. When the bis-HCl salt was used a base such as diisoproplyethylamine (DIPEA) was added to neutralize the acid. The transesterification reaction did however apparently proceed with the bis-TFA salt of N-methyl piperazine acetic acid without the addition of base.

V. Labeling and Analysis Using a Set of Isobaric Labeling Reagents

Example 24

General Procedure for the Labeling of Peptide Mixtures (from Protein Digestion) with the NHS-Ester of N-Methyl Piperazine Acetic Acid (NMPAA-NHS) Reagents of an Isobaric Set Buffer and Reagent Compositions

| Reagent | Composition |
|---|---|
| Dissolution Buffer | 0.5M triethylammonium bicarbonate (TEAmB), pH 8.5 |
| Denaturing Reagent | 2% sodium dodecyl sulfate (SDS) in water |
| Reducing Reagent | 50 mM neutralized tris[2-carboxyethyl] phosphine (TCEP) in water |
| Cysteine Blocking Reagent | 200 mM methyl methanethiosulfonate (MMTS) in 2-propanol |
| Trypsin | 25 µg TPCK-treated trypsin, 222 µg calcium chloride |
| NMPAA-NHS | Approximately 1 mg active reagent/tube |

Reducing the Proteins and Blocking Cysteine
 Note: If necessary add up to 100 µL Dissolution Buffer to dissolve the sample in steps 1 and 2 below. Dry down the excess buffer before labeling (see step 6 in "Digesting with Trypsin.")

1. Add 20 µL of the Dissolution Buffer to a tube containing 100 µg of the Control sample. (If working with a concentrated sample solution, add Denaturing Buffer to bring the volume up to 20 µL.)
2. Add 20 µL of the Dissolution Buffer to a tube containing 100 µg of the Test sample. (If working with a concentrated sample solution, add Denaturing Buffer to bring the volume up to 20 µL.)
3. Add 1 µL of the Denaturing Reagent to both the Control and Test sample tubes.
4. Add 2 µL of the Reducing Reagent to both the Control and Test sample tubes.
5. Vortex to mix, then spin.
6. Incubate Control and Test tubes at 60° C. for 1 hour.
7. Vortex to mix, then spin.
8. Add 1 µL Cysteine Blocking Reagent to each tube.
9. Vortex to mix, then spin.
10. Incubate at room temperature for 10 minutes.
11. Vortex to mix, then spin the Control and Test tubes.

Digesting with Trypsin
1. Reconstitute a vial of trypsin with calcium chloride with 25 µL of Milli-Q® water or equivalent.
2. Vortex to mix, then spin.
3. Add 10 µL of the trypsin solution to each of the protein solutions.
4. Vortex to mix, then spin.
5. Incubate 12 to 16 hours at 37° C.
6. Vortex to mix, then spin.

Note: If you increased the denaturing buffer in steps 1 and 2 of "Reducing the Proteins and Blocking Cysteine," dry the samples in a centrifugal vacuum concentrator. To the dried sample, add 30 µL of Denaturing Buffer, vortex to mix, then spin.

Labeling with the NHS Esters of NMPAA (NMPAA-NHS)
Note: Bring a vial of NMPAA-NHS Reagent 114 and a vial of NMPAA-NHS Reagent 117 to room temperature (the vial should contain approximately 1 mg of active reagent).
1. Add 70 µL of absolute ethanol to each reagent vial.
2. Vortex for 1 minute to dissolve, then spin.
3. Transfer the solution of NMPAA-NHS Reagent 114 to the Control sample solution.
4. Transfer the solution of NMPAA-NHS Reagent 117 to the Test sample solution.
5. Vortex each vial to mix, then spin.
6. Incubate for 1 hour at room temperature.
7. Vortex each vial to mix, then spin.
8. Combine the contents of the NMPAA-NHS Reagent 114 vial and the NMPAA-NHS Reagent 117 vial in one tube.

Note: If a greater number of samples or controls is desired, the NMPAA-NHS Reagent 115 and NMPAA-NHS Reagent 116 can also be used.

Final Concentration of Components in Labeling Solution (104 µL Total Volume):
96 mM triethylammonium bicarbonate
0.019% SDS
0.96 mM TCEP
1.9 mM MMTS
10 µg trypsin
89 µg calcium chloride
1 mg NMPAA-NHS Reagent
1 µL 2-propanol
70 µL ethanol (67%)
100 µg sample Example 25

Preparation and Analysis of a Protein Mixture (a.k.a. 6 Protein Mix)

A protein mix consisting of equimolar amounts of bovine serum albumin, alpha casein, alcohol dehydrogenase, alpha-lactalbumin, beta galactosidase, serotransferrin and myoglobin (all from Sigma, Milwaukee Wis.) was reduced (2 mM TCEP, Pierce, Rockford Ill.), alkylated (5 mM Iodoacetamide, Sigma) and trypsin digested (1:20, Promega, Madison Wis.). Four equal aliquots were treated each with one of the four enriched N-methyl piperazine acetic acid (NMPAA) NHS ester reagents (114, 115, 116 and 117) by adding 0.5 mg of reagent to 50 µL of peptide solution and allowing to react for 30 minutes at room temperature. The four reactions were combined, evaporated to dryness, and quantities representing 500 fmol of each component were analyzed by LC-MS/MS as described below in Example 26 under the heading "LC-MS analysis".

Example 26

Multiplex Protein Quantitation in *Saccaromyces Cerevisiae*

Yeast Protein Extraction And Labeling. Log phase cells (75% log) were harvested, frozen and mechanically lysed by grinding over dry ice. Crude cell lysate was prepared by suspending frozen cellular material (100 mg wet weight) in 1 ml lysis buffer (0.1 M TEAmB, 0.1% v/v Triton X-100, 6M Guanidine), vortexing (1 min), sonicating (5×30 sec) and pelleting insoluble debris by centrifugation at 13000 g for 5 min. Final measured protein concentrations were 3-3.4 mg/mL. Protein was reduced (2 mM TCEP, 37° C., 1 hr), alkylated (5 mM iodoacetamide, 37° C., 2 hours) and precipitated by the addition of 6 volumes of cold acetone (dry ice 20 min). Protein was collected by centrifugation (13000 g, 5 min), dried in air and frozen at −80° C. For digestion, protein was resuspended in Digestion Buffer (100 mM TEAmB, 0.05% w/v SDS) to a final concentration of 1 mg/mL (total protein measured by BCA assay (Sigma, St. Louis, Mo.)). Equal aliquots (500 µg) from each lysate were then digested with trypsin overnight at 37° C. (Sigma, 1:40 w/w added at 0 and 2 hr) and lyophilized. Labeling with multiplex reagents. For each yeast strain, 150 µg of total protein was resuspended in 100 µL of labeling buffer (0.25 M TEAmB, 75% Ethanol), after which 1 mg of each isotopically enriched N-methyl piperazine acetic acid NHS ester was added (1% w/v final) and allowed to react at room temperature for 30 min. Residual reagent was quenched by adding 300 µL of water and allowing excess reagent to completely hydrolyze over an additional 30 minutes, then the 3 labeled samples mixed and lyophilized.

Cation Exchange Chromatography. The combined peptide mixture was separated by strong cation exchange (SCX) chromatography on an Agilent 1100 HPLC system using a PolySulfoethyl A column (4.6×100 mm, 5 µm 300A). Sample was dissolved in 4 ml SCX loading buffer (25% v/v ACN, 10 mM KH$_2$PO$_4$, pH3 with phosphoric acid) and loaded and washed isocratically for 20 min at 0.5 mL/min to remove excess reagent. Peptides were eluted with a linear gradient of 0-500 mM KCl (25% v/v ACN, 10 mM KH$_2$PO$_4$, pH3) at 1 mL/min, with fractions collected at 1 minute intervals.

LC-MS analysis. Peptide separation was performed on an Ultimate™ chromatography system (Dionex-LC Packings, Hercules, Calif.) equipped with a Probot MALDI spotting device. Individual SCX fraction containing ~10 µg of protein material were injected and captured onto a 0.3×5 mm trap column (3μ $C_{18}$ (Dionex-LC Packings, Hercules, Calif.)) and then eluted onto a 0.1×150 mm analytical column (3μ $C_{18}$ (Dionex-LC Packings, Hercules, Calif.)) using an automated binary gradient (800 nL/min.) from 95% buffer A (2% Acetonitrile, 0.1% TFA) to 45% buffer B (85% Acetonitrile, 5% isopropanol, 0.1% TFA) over 35 min, then 45-90% B in 5 minutes. For matrix assisted laser desorption ionization mass spec/mass spec (MALDI MS/MS) analysis, column effluent was mixed in a 1:2 ratio with matrix assisted laser desorption ionization (MALDI) matrix (7 mg/mL-α-cyano-4-hydroxycinnamic acid) through a 25 mL mixing tee (Upchurch, Wash.) and spotted in 16×16 spot arrays. MALDI plates were analyzed on an ABI 4700 (Applied Biosystems, Framingham, Mass.) proteomics analyzer. For electrospray analysis, an Ultimate LC system interfaced to a Qstar Pulsar™ (Applied Biosystems-MDS Sciex) mass spectrometer was used. The liquid chromatography (LC) conditions were similar to those used for LC-MALDI, with peptides separated at a flow rate of 300 nl/min over a 75 μm×150 mm $C_{18}$ column (Pepmap, Dionex) using a 2 hour gradient of 5%-35% B (A: 2% acetonitrile/0.1% formic acid; B=98% acetonitrile/0.1% formic acid). Survey scans were acquired from m/z 300-1500 with up to 3 precursors selected for MS/MS from 90-2000 m/z using dynamic exclusion. A rolling collision energy was used to promote fragmentation, typical average values for doubly charged ions were 41 V and 56 V for 600 and 900 m/z respectively, and for triply charged ions typical average values were 29 V and 43 V for m/z 600 and m/z 900 respectively. The collision energy range was approximately 20% higher than that used for unlabelled peptides to overcome the stabilizing effect of the basic N-terminal derivative and achieve equivalent fragmentation efficiency.

Data analysis and interpretation. Peptide and protein identification was performed using the Mascot search engine (Ver 1.9, Matrix Science, London UK)[14]. Database searching was restricted to tryptic peptides of yeast (Swissprot version 42.5; 4924 S. cerevisiae sequences; 138922 total sequences). S-acetamido, N-terminal and Lysine modifications were selected as fixed, Met oxidation as variable, 1 missed cleavage allowed and precursor error tolerance at <50 ppm. Signature-ion peak areas from the isobaric tags were extracted from the 4700 or QSTAR raw data and matched to identified peptides using prototype software tools. The complete list of identified peptides was then housed in an Access (Microsoft, WA) database for grouping of results into proteins and calculation of ratios and standard deviation. Abundance ratio calculations included corrections for overlapping isotopic contributions (both natural and enriched $^{13}C$ components).

Example 27

Generic Workflow for Labeling Protein Containing Samples Prior to Digestion

Although the following example is discussed with respect to a prepared 6 Protein Mixture, the workflow discussed can be applied generally, including application to unknown samples of interest. The protocol set forth below describes denaturing and reduction of the protein before labeling. It is also possible to perform the denaturing and reduction after the labeling reaction is performed.
A. Reducing the Proteins and Blocking Cysteine
  1. Add 20 μL of the Dissolution Buffer to a tube containing 100 μg of 6 Protein Mixture (3.7 nmol total)
  2. Add 2 μL of the Reducing Reagent (TCEP) and 1 μl of the Denaturing Reagent provided to the sample tube (optional or performed after step B10).
  3. Vortex to mix, then spin.
  4. Incubate the tube at 60° C. for 1 hour (dissolve the proteins).
  5. Spin to bring the solution to the bottom of the tube.
  6. Add 1 μL Cysteine Blocking Reagents (MMTS) to each tube.
  7. Vortex to mix, then spin.
  8. Incubate at room temperature for 10 minutes.
B. Labeling the Protein Mixture with the Labeling Reagent Reagents
  1. Bring each vial of 1 mg of NMPAA-NHS to room temperature.
  2. Spin the reagent to bring all powder to the bottom of the vial.
  3. Add 70 μL ethanol to the reagent vial.
  4. Vortex the vial for 1 minute to dissolve the reagent, then spin.
  5. Transfer one prepared vial of labeling reagent to one protein mixture sample tube.
  6. Vortex each vial to mix, then spin.
  7. Incubate at room temperature.
  8. Add 30 μL 1M NH4HCO3 to the sample vial, vortex to mix, and then spin.
  9. Incubate 20 minutes to completely quench the reagent.
  10. Combine the contents of each labeling reaction in one tube.
  11. Acetone precipitation: add 1 mL cold Acetone to the sample vial, vortex to mix, and then spin.
  12. Incubate 2 hours at −20° C.
  13. Spin the vial for 15 minutes at 14 setting.
  14. Decant the supernatant.
  15. Speed-vac 2 minutes to remove residual acetone.
  16. Re-suspend the sample tube with 175 μL 25 mM NH4HCO3; incubate at 60° C. for 1 hour.
Digest the Labeled Proteins with Trypsin
  1. Reconstitute a vial of trypsin (25 mg with CaCl) with 25 μL Milli-Q water.
  2. Vortex to mix, then spin.
  3. Add 25 μL of trypsin solution to the protein solution.
  4. Vortex to mix, then spin.
  5. Incubate at 37° C. overnight.
  6. Spin to bring the solution to the bottom of the tube.

Example 28

Generic Procedure for Labeling Protein Containing Samples Prior to Digestion (Prophetic)

Samples:
1) Laminin 50 mmol, TPI1 (a known protein) 25 μmol (20 μL 1.2 mmol/mL) and TPI2 (a known protein) 20 μmol (25 μL 0.79 mmol/mL) in 50 mM tris-(hydroxymethyl)aminomethane (Tris) and 0.1% SDS pH 8.5 (ICAT Dissolution Buffer) 4 Total volume was 250 μL
2) TPI protein digest (100 μg TPI/2004)
Procedure:
Samples 1 and 2 are reduced and denatured by adding 2 μL 50 mM TCEP, heat block for 10 minutes. Blocking step can be eliminated.
  1. Dissolve protein mixture (50-100 μg) in 50 μL of denaturing buffer.
  2. Add 1 μl of Reducing Reagent to the protein solution to achieve 2 mM final concentration.
  3. Incubate the protein solution at 37° C. for 1 hour.

4. Add 1 µl of MMTS to the denatured and reduced protein solution and vortex it for 10 minutes.
5. Dilute the protein solution 1:1 with Dilution Buffer (0.1 M $NH_4HCO_3$).
6. Add 2 µl of LysC to the protein solution and digest it at 37° C. for 2 hours.
7. Dilute the protein solution 1:1 with water.
8. Add 10 µl of trypsin (~5 µg) and continue digestion at 37° C. for 5-10 hours.
9. Add 2 µl of the Reducing Reagent to the digest and reduce the cysteine containing peptides at 37 degree for 1 hour.

Capturing of Cys-Peptides with the Support Illustrated in FIG. 21C ($CCS^2$)
1. Wash the $CCS^2$ resin in the NANOSEP™ tube three times with MilliQ H20 (collected washes for analysis. (3×100 µL, 5 min).
2. Condition the resin with 50 mM Tris containing, pH 8.5 (200 µl, 5 min)
3. Transfer each digestion mixture (200 µl) into NANOSEP™ tube containing 7 mg of the $CCS^2$.
4. Set the tubes into a tube holder on a vortex platform and vortex at a low speed for 60 minutes.
5. Spin the NANOSEP sample tubes in an Eppendorf centrifuge to remove the unbound peptides and analyze the filtrate by HPLC (FT, Flow through).
6. Wash additional unbound sample off the resin with 100 µL MilliQ $H_2O$, 5 min and add wash to flow through sample for analysis.

Quenching of the $CCS^2$ Resin with N-Acetylcysteamine
1. Add 200 µl of 1.0% of N-acetylcysteamine solution (i.e. 2 µL in 200 µl of 50 mM Tris, pH 8.5) into the resin tube and vortex the tube for 30 min at room temperature (RT).
2. Spin the tube in the Eppendorf centrifuge to remove the reagents.
3. Wash the quenched resin with 10 mM TEAmB (3×100 µl), the washing solvent was collected and analyzed (HPLC).
4. Dry the resin on speed vac.

Tagging of Cys-Peptides Using NMPAA-NHS Labeling Reagent
1. Weight 5 mg of labeling reagent in an Eppendorf tube. (enough for 5 reactions)
2. Mix the following Tagging buffers and solvents in a separate tube:
50 µl of 1.0 M TEAmB (Triethylammonium bicarbonate)
250 µl of $H_2O$
700 µl of ethanol (EtOH)
3. Transfer the above solution (4×125 µL) into the labeling reagent tube, vortex the mixture (~20 sec) and immediately transfer 100 µL into each of the 4 sample tubes.
4. Vortex the tube for 1 hr at room temperature (RT).
5. Spin down the reaction (Collect for analysis)
6. Wash the resin with 3 times of 0.1% TFA in $H_2O$ (3×100 µl) and one more time of 100 µl of 25% acetonitrile containing 0.1% TFA. Optionally, add these washes to the initial labeling solution for analysis)
7. Completely dry the resin in a speedvac before the cleavage steps.

Cleavage of the Tagged Peptides from the Resin
Acid Cleavage:
1. Add 200 µl of cocktail containing 95% TFA, 5% TIPS to the dried sample tube and vortex at a low speed for 1 hr at RT.
2. Spin down the tube and keep the filtrate in the tube.
3. Add 100 µl of 95% TFA, 5% TIPS to the resin tube and spin down again.
4. Dry down the pooled filtrate and redissolve all samples in 50 µL MilliQ $H_2O$.

Redissolve all other samples in 50 µL MilliQ $H_2O$.

HPLC analysis: 5 µL in 95 µL $H_2O$, inject 80 µL

MALDI-MS final cleaved product 1:10 in α-cyano-4-hydroxy cinnamic acid (ACHCA).

The examples set forth above are for illustrative purposes only and should not be viewed as a limitation on the scope of the invention.

We claim:

1. A method for proteomic analysis of polypeptides, comprising:
a) reacting each of two or more polypeptide samples, each sample comprising a reactive polypeptide analyte, with a different isobaric and/or isomeric labeling reagent of a set of isobaric and/or isomeric labeling reagents to thereby produce two or more differentially labeled polypeptide analytes having the same mass, wherein each labeling reagent is a 6 membered heterocyclic ring comprising a ring nitrogen atom that is N-alkylated with a substituted or unsubstituted acetic acid moiety to which the polypeptide analyte is linked through a carbonyl carbon of the N-alkyl acetic acid moiety
b) mixing two or more of the differentially labeled polypeptide samples, or a portion thereof, and optionally one or more calibration standards to thereby produce a sample mixture comprising the same reactive polypeptide analyte labeled with two or more different labels having the same mass;
c) digesting each differentially labeled polypeptide sample with at least one enzyme to degrade components of the sample, to form degraded samples, after performing step (a); and
d) performing a mass analysis of the components of the degraded samples.

2. The method of claim 1, wherein the polypeptide analyte is a protein.

3. The method of claim 1, wherein the sample mixture comprises the same polypeptide analyte labeled with two or more different labels having the same mass, wherein at least two of the labeled polypeptide analytes are compounds of the formula selected from the group consisting of:

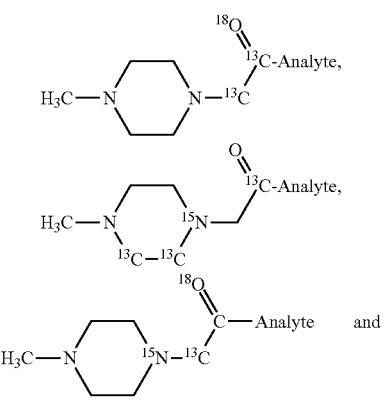

-continued

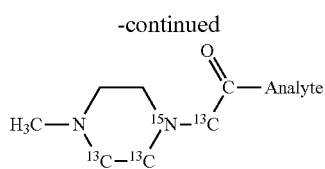

or a salt form and/or hydrate form thereof.

4. The method of claim 3, wherein the polypeptide analyte is a full-length protein.

5. The method of claim 3, wherein the fragmentation and further analysis produces at least two signature ions of the molecular formula selected from the group consisting of: $^{13}CC_5H_{13}N_2^+$, $^{13}CC_5H_{13}{}^{15}NN^+$, $^{13}C_2C_4H_{13}{}^{15}NN^+$ and $^{13}C_3C_3H_{13}{}^{15}NN^+$.

6. The method of claim 1, wherein the polypeptide label comprises one or more heavy atom isotopes.

7. The method of claim 1, further comprising the step of quantifying the concentration of the reactive polypeptide analyte present in the two or more samples.

* * * * *